(12) United States Patent
Ahrens et al.

(10) Patent No.: US 8,337,850 B2
(45) Date of Patent: Dec. 25, 2012

(54) 4-1BB BINDING MOLECULES

(75) Inventors: Bianca Ahrens, München (DE); Sangita M. Baxi, San Diego, CA (US); Timothy Scott Fisher, San Diego, CA (US); Richard Michael Jerome, East Hampstead, NH (US); Kathrin Ladetzki-Baehs, Planegg (DE); Theodore Oliphant, Galesburg, MI (US); Leslie Lynne Sharp, San Diego, CA (US); Michael Tesar, Augsberg (DE); Libbey Anne Yates, Dardenne Prairie, MO (US); Moritz Zulley, München (DE)

(73) Assignee: Pfizer Inc., San Diego, CA (US)

( * ) Notice: Subject to any disclaimer, the term of this patent is extended or adjusted under 35 U.S.C. 154(b) by 0 days.

(21) Appl. No.: 13/228,532

(22) Filed: Sep. 9, 2011

(65) Prior Publication Data

US 2012/0237498 A1   Sep. 20, 2012

Related U.S. Application Data

(60) Provisional application No. 61/381,210, filed on Sep. 9, 2010.

(51) Int. Cl.
  *A61K 39/395* (2006.01)
  *C07K 16/28* (2006.01)
  *C12P 21/02* (2006.01)

(52) U.S. Cl. ............. 424/143.1; 530/387.1; 530/388.23; 530/389.2; 530/391.3; 424/139.1; 435/69.1; 536/23.5

(58) Field of Classification Search .................. None
  See application file for complete search history.

(56) References Cited

U.S. PATENT DOCUMENTS

| | | | |
|---|---|---|---|
| 4,399,216 A | 8/1983 | Axel | |
| 4,634,665 A | 1/1987 | Axel | |
| 4,816,567 A | 3/1989 | Cabilly | |
| 5,179,017 A | 1/1993 | Axel | |
| 5,677,425 A | 10/1997 | Bodmer | |
| 5,994,619 A | 11/1999 | Stice | |
| 6,172,197 B1 | 1/2001 | McCafferty | |
| 6,291,158 B1 | 9/2001 | Winter | |
| 6,582,915 B1 | 6/2003 | Griffiths | |
| 6,593,081 B1 | 7/2003 | Grigg | |
| 6,696,245 B2 | 2/2004 | Winter | |
| 6,765,087 B1 | 7/2004 | Costerman | |
| 6,838,254 B1 | 1/2005 | Hamers | |
| 2006/0153808 A1 | 7/2006 | Cristofanilli | |
| 2007/0117809 A1 | 5/2007 | Fridman | |

FOREIGN PATENT DOCUMENTS

| | | |
|---|---|---|
| EP | 338841 A1 | 10/1999 |
| EP | 0368684 | 9/2004 |
| EP | 0616640 | 9/2004 |
| WO | WO/87/04462 | 7/1987 |
| WO | WO/89/01036 | 2/1989 |
| WO | WO/9629348 | 9/1996 |
| WO | WO/9816249 | 4/1998 |
| WO | WO/01/05950 | 1/2001 |
| WO | WO/02/053596 | 7/2002 |
| WO | WO/02/055106 | 7/2002 |
| WO | WO/03/002609 | 1/2003 |
| WO | WO/03/015711 | 2/2003 |
| WO | WO/03/040170 | 5/2003 |
| WO | WO/03/048731 | 6/2003 |
| WO | WO/03084999 | 10/2003 |
| WO | WO/2004/003019 | 1/2004 |
| WO | WO/2004/010947 | 2/2004 |
| WO | WO/2004/016805 | 2/2004 |
| WO | WO/2004/055513 | 7/2004 |
| WO | WO/2004/058821 | 7/2004 |
| WO | WO/2004/081026 | 9/2004 |
| WO | WO/2004/101790 | 11/2004 |
| WO | WO/2005/035572 | 4/2005 |
| WO | WO/2005/035584 | 4/2005 |
| WO | WO/2006/079372 | 8/2006 |
| WO | WO/2006/129163 | 12/2006 |
| WO | WO/2007/059782 | 5/2007 |
| WO | WO/2009/022215 | 2/2009 |
| WO | WO/2009/079335 | 6/2009 |

OTHER PUBLICATIONS

Abraham, R., et al., "Determination of Binding Constants of Diabodies Directed against Prostate-specific Antigen using Electrochemiluminescence-based Immunoassays," *Journal of Molecular Recognition*, 1996, vol. 9, pp. 456-461.

Allen, T., "Ligand-targeted therapeutics in anticancer therapy," *Nature Reviews Cancer*, 2002, vol. 2 pp. 750-763.

Altschul, S., et al., "Basic local alignment search tool," Journal of Molecular Biology, 1990, vol. 215, pp. 403-410.

Altschul, S. et al., "Gapped BLAST and PSI-BLAST: a new generation of protein database search programs," *Nucleic Acids Research*, 1997, vol. 25, pp. 3389-3401.

Bird, R., et al."Single-chain antigen-binding proteins," Science, 1988, vol. 242, pp. 423-426.

Broll,K., et al., "CD137 expression in tumor vessel walls. High correlation with malignant tumors," *American Journal of clinical pathology*, 2001, vol. 115(4), pp. 543-549.

Cheuk, A., et al. "Role of 4-1BB:4-1BB ligand in cancer immunotherapy," *Cancer Gene Therapy*, 2004, vol. 11, pp. 215-226.

(Continued)

*Primary Examiner* — Bridget E Bunner
*Assistant Examiner* — Fozia Hamud
(74) *Attorney, Agent, or Firm* — Lynn B. Apelgren

(57) ABSTRACT

The present disclosure provides isolated binding molecules that bind to human 4-1BB, nucleic acid molecules encoding an amino acid sequence of the binding molecules, vectors comprising the nucleic acid molecules, host cells containing the vectors, methods of making the binding molecules, pharmaceutical compositions containing the binding molecules, and methods of using the binding molecules or compositions.

7 Claims, 8 Drawing Sheets

OTHER PUBLICATIONS

Clackson, T., et al., "Making antibody fragments using phage display libraries" *Nature*, 1991, vol. 352, pp. 624-628.

Cox, J. et al., "A Directory of human germ-line V kappa segments reveals a strong bias in their usage," *European Journal of Immunology*. 1994, vol. 24, pp. 827-836.

Croft, M., "The role of TNF superfamily members in T-cell function and diseases," Nature Reviews Immunology, 2009, vol. 9, pp. 271-285.

Drenkard,D., et al., "CD137 is expressed on blood vessel walls at sites of inflammation and enhances monocyte migratory activity," *FASEB Journal*, 2007, vol. 21, pp. 456-463.

Friquet, B., "Measurements of the ture affinity constant in solution of antigen-antibody complexes by enzyme-linked immunosorbent assay," *Journal of Immunology Methods*, 1985, vol. 77, pp. 305.

Green, L., et al., Antigen-specific human monoclonal antibodies from mice engineered with human Ig heavy and light chain YACs, *Nature*, 1994, vol. 7. pp. 13-21.

Haenel, C., et al., "Characterization of high-affinity antibodies by electrochemiluminescence-based equilibrium titration," *Analytical Biochemistry*, 2005, vol. 339, pp. 182-184.

Holliger, P., et al., ""Diabodies": small bivalent and bispecific antibody fragments," *Proceedings of the National Academy of Sciences of the Unites States of America*, 1993, vol. 90, pp. 6444-6448.

Huston, J., et al., "Protein engineering of antibody binding sites: recovery of specific activity in an anti-digoxin single-chain Fv analogue produced in *Escherichia coli*," *Proceedings of the National Academy of Sciences of the Unites States of America*, 1988, vol. 85, pp. 5879-5883.

International Search Report mailed Nov. 20, 2011 for PCT/IB2011/052425 filed Jun. 1, 2011,19 pages.

Kaufman, R., et al., "Amplification and expression of sequences cotransfected with a modular dihydrofolate reductase complementary dna gene" *Journal of Molecular Biology*, 1982, vol. 159, pp. 601-621.

Knappik, A., et al., "Fully Synthetic Human Combinatorial Antibody Libraries (HuCAL) Based on Modular Consensus Framworks and CDRs Randomized with Trinucleotides." J. Mol. Biol. 2000, vol. 296, pp. 57-86.

Kohler, G., et al., "Continuous cultures of fused cells secreting antibody of predefined specificity," *Nature*, 1975, vol. 256 pp. 495-497.

Logan, T., et al., "Phase I study of BMS-663513, a fully human anti-CD137 agonist monoclonal antibody, in patients (Pts) with advanced cancer (CA)," *Journal of Immunotherapy*, 2008, vol. 31, No. 9, p. 956.

Loo, D., et al., "Analysis of 4-1BBL and laminin binding to murine 4-1BB, a member of the tumor necrosis factor receptor superfamily, and comparison with human 4-1BB," The Journal of Biological Chemistry, 1997, vol. 272, No. 10, pp. 6448-6456.

Lynch, D., "The promise of 4-1BB (CD137)-mediated immunomodulation and the immunotherapy of cancer," *Immunological Reviews*, 2008, vol. 22, pp. 227-286.

Marks, J. et al., "By-passing immunization. Human antibodies from V-gene libraries displayed on phage," *Journal of Molecular Biology*, 1991, vol. 222, pp. 581-597.

McCafferty, J., et al., "Phage antibodies: filamentous phage displaying antibody variable domains," *Nature*, 1990, vol. 348, pp. 552-554.

NIH Publication No. 91-3242 (1991).

Olofsson, P., et al., "CD137 is Expressed in Human Atherosclerosis and Promotes Development of Plaque Inflammation in Hypercholesterolemic Mice," *Circulation*, 2008, vol. 117: 1292-1301.

Pastan, I., et al., "Immunotoxins in cancer therapy" *Current Opinion in Investigational Drugs*, 2002, vol. 3, pp. 1089-1091.

Payne,G., "Progress in immunoconjugate cancer therapeutics," *Cancer Cell*, 2003, vol. 3, pp. 207-212.

Pearson, WR, "Rapid and Sensitive Sequence Comparison with FASTP and FASTA," *Methods Enzymology*, 1990, 183:63-98.

Pearson, WR, "Flexible sequence similarity searching with the FASTA3 Program Package," *Methods in Molecular Biology*. 2000, 132:185-219.

Poljak, R., et al., "Production and structure of diabodies," *Structure*, 1994, vol. 2, pp. 1121-1123.

Rothe, C., et al., "The Human Combinatorial Antibody Library HuCAL GOLD combines Diversification of All Six CDRs According to the Natural Immune System with a Novel Display Method for Efficient Selection of High-Affinity Antibodies," *Journal of Molecular Biology* 2008, vol. 376, pp. 1182-1200.

Saito, G., et al., "*Drug delivery strategy utilizing conjugation via reversible disulfide linkages: role and site of cellular reducing activities*,"Advanced Drug Delivery Reviews, 2003, vol. 55, pp. 199-215.

Seaman, S., et al., "Genes that Distinguish Physiological and Pathological Angiogenesis," *Cancer Cell*, 2007, vol. 11, pp. 539-554.

Senter, P., et al., "Selective activation of anticancer prodrugs by monoclonal antibody-enzyme conjugates," *Advanced Drug Delivey Reviews*, 2001, vol. 53, pp. 247-264.

Takebe, Y.,et al., "SR alpha promoter: and efficient and versatile mammalian cDNA expression system composed of the simian virus 40 early promoter and the R-U5 segment of human T-cell leukemia virus type 1 long terminal repeat," *Molecular and cellular biology*, 1988, vol. 8, pp. 466-472.

Tomlinson, I. M., et al., "The repertoire of human germline VH sequences reveals about fifty groups of VH segments with different hypervariable loops," *Journal of Molecular Biology*,vol. 227, pp. 776-798, 1992.

Trail, P., et al., "Monoclonal antibody drug immunoconjugates for targeted treatment of cancer" *Cancer Immunology, Immunotherapy*, 2003, vol. 52, pp. 328-337.

Urlaub, G., et al., Isolation of Chinese hamster cell mutants deficient in dihydrofolate reductase activity, *Proceedings of the National Academy of Sciences of the United States of America*, 1980, vol. 77, pp. 4216-4220.

Vinay, D., et al., "Dual immunoregulatory pathways of 4-1BB signaling," *Journal of Molecular Medicine*, 2006, vol. 84, pp. 726-736.

Wang,C., et al., "Immune regulation by 4-1BB and 4-1BBL: complexities and challenges" *Immunological Reviews*, 2009, vol. 229: 192-215.

Ward, E., et al., "Binding activities of a repertoire of single immunoglobulin variable domains secreted from *Escherichia coli*," *Nature*, 1989, vol. 341, pp. 544-546.

Ye, Z., et al., "Gene therapy for cancer using single-chain Fv fragments specific for 4-1BB" Nature Medicine, 2002, vol. 8, No. 4, pp. 343-348.

FIG. 8

Figure 8 (illegible sequence alignment of heavy chain variable region and light chain variable region, CDRs are underlined)

SEQUENCE LISTING

```
<160> NUMBER OF SEQ ID NOS: 74

<210> SEQ ID NO 1
<211> LENGTH: 6
<212> TYPE: PRT
<213> ORGANISM: Homo sapien

<400> SEQUENCE: 1

Asn Ser Tyr Ala Ile Ser
1               5

<210> SEQ ID NO 2
<211> LENGTH: 17
<212> TYPE: PRT
<213> ORGANISM: Homo sapien

<400> SEQUENCE: 2

Gly Ile Ile Pro Gly Phe Gly Thr Ala Asn Tyr Ala Gln Lys Phe Gln
1               5                   10                  15

Gly

<210> SEQ ID NO 3
<211> LENGTH: 11
<212> TYPE: PRT
<213> ORGANISM: Homo sapien

<400> SEQUENCE: 3

Arg Lys Asn Glu Glu Asp Gly Gly Phe Asp His
1               5                   10

<210> SEQ ID NO 4
```

```
<211> LENGTH: 119
<212> TYPE: PRT
<213> ORGANISM: Homo sapien

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Asn Glu Glu Asp Gly Gly Phe Asp His Trp Gly Gln Gly
            100                 105                 110

Thr Leu Val Thr Val Ser Ser
            115

<210> SEQ ID NO 5
<211> LENGTH: 445
<212> TYPE: PRT
<213> ORGANISM: Homo sapien

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Asn Glu Glu Asp Gly Gly Phe Asp His Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220
```

-continued

```
Cys Pro Pro Cys Pro Ala Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
        260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 6
<211> LENGTH: 11
<212> TYPE: PRT
<213> ORGANISM: Homo sapien

<400> SEQUENCE: 6

Ser Gly Asp Asn Leu Gly Asp Tyr Tyr Ala Ser
1               5                   10

<210> SEQ ID NO 7
<211> LENGTH: 7
<212> TYPE: PRT
<213> ORGANISM: Homo sapien

<400> SEQUENCE: 7

Asp Asp Ser Asn Arg Pro Ser
1               5

<210> SEQ ID NO 8
<211> LENGTH: 10
<212> TYPE: PRT
<213> ORGANISM: Homo sapien

<400> SEQUENCE: 8

Gln Thr Trp Asp Gly Thr Leu His Phe Val
1               5                   10

<210> SEQ ID NO 9
<211> LENGTH: 107
<212> TYPE: PRT
<213> ORGANISM: Homo sapien
```

<400> SEQUENCE: 9

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Asp Tyr Tyr Ala
            20                  25                  30

Ser Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Gly Thr Leu His Phe
                85                  90                  95

Val Phe Gly Gly Gly Thr Lys Leu Thr Val Leu
            100                 105

<210> SEQ ID NO 10
<211> LENGTH: 213
<212> TYPE: PRT
<213> ORGANISM: Homo sapien

<400> SEQUENCE: 10

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Asp Tyr Tyr Ala
            20                  25                  30

Ser Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Gly Thr Leu His Phe
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 11
<211> LENGTH: 357
<212> TYPE: DNA
<213> ORGANISM: Homo sapien

<400> SEQUENCE: 11

```
caggtgcaat tggttcagtc tggcgcggaa gtgaaaaaac cgggcagcag cgtgaaagtg    60
agctgcaaag cctccggagg cactttaat tcttatgcta tttcttgggt gcgccaagcc    120
cctgggcagg gtctcgagtg gatgggcggt atcattccgg ttttggcac tgcgaattac    180
gcgcagaagt ttcagggccg ggtgaccatt accgcggatg aaagcaccag caccgcgtat    240
atggaactga gcagcctgcg tagcgaagat acggccgtgt attattgcgc gcgtaagaat    300
gaggaggatg gtggttttga tcattggggc caaggcaccc tggtgacggt tagctca       357
```

<210> SEQ ID NO 12
<211> LENGTH: 321
<212> TYPE: DNA
<213> ORGANISM: Homo sapien

<400> SEQUENCE: 12

```
gatatcgaac tgacccagcc gccttcagtg agcgttgcac caggtcagac cgcgcgtatc    60
tcgtgtagcg gcgataatct tggtgattat tatgcttctt ggtaccagca gaaacccggg    120
caggcgccag ttcttgtgat ttatgatgat tctaatcgtc cctcaggcat cccgaacgc    180
tttagcggat ccaacagcgg caacaccgcg accctgacca ttagcggcac tcaggcggaa    240
gacgaagcgg attattattg ccagacttgg gatggtactc ttcatttgt gttggcggc    300
ggcacgaagt taaccgttct t                                              321
```

<210> SEQ ID NO 13
<211> LENGTH: 1335
<212> TYPE: DNA
<213> ORGANISM: Homo sapien

<400> SEQUENCE: 13

```
caggtgcaat tggttcagtc tggcgcggaa gtgaaaaaac cgggcagcag cgtgaaagtg    60
agctgcaaag cctccggagg cactttaat tcttatgcta tttcttgggt gcgccaagcc    120
cctgggcagg gtctcgagtg gatgggcggt atcattccgg ttttggcac tgcgaattac    180
gcgcagaagt ttcagggccg ggtgaccatt accgcggatg aaagcaccag caccgcgtat    240
atggaactga gcagcctgcg tagcgaagat acggccgtgt attattgcgc gcgtaagaat    300
gaggaggatg gtggttttga tcattggggc caaggcaccc tggtgacggt tagctcagcc    360
tccaccaagg gcccatcggt cttccccctg gcgccctgct ccaggagcac ctccgagagc    420
acagcggccc tgggctgcct ggtcaaggac tacttcccg aaccggtgac ggtgtcgtgg    480
aactcaggcg ctctgaccag cggcgtgcac accttcccgg ctgtcctaca gtcctcagga    540
ctctactccc tcagcagcgt agtgaccgtg ccctccagca cttcggcac ccagacctac    600
acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttccccccaa aacccaagga caccctcatg atctcccgga cccctgaggt cacgtgcgtg    780
gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgtcgt gcaccaggac tggctgaacg gcaaggagta caagtgcaag    960
gtctccaaca aaggcctccc agcccccatc gagaaaacca tctccaaaac caaagggcag    1020
ccccgagaac acaggtgta caccctgccc ccatcccggg aggagatgac caagaaccag    1080
gtcagcctga cctgcctggt caaaggcttc taccccagcg acatcgccgt ggagtgggag    1140
```

```
agcaatgggc agccggagaa caactacaag accacacctc ccatgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacacagaa gagcctctcc    1320
ctgtctccgg gtaaa                                                    1335

<210> SEQ ID NO 14
<211> LENGTH: 639
<212> TYPE: DNA
<213> ORGANISM: Homo sapien

<400> SEQUENCE: 14
gatatcgaac tgacccagcc gccttcagtg agcgttgcac caggtcagac cgcgcgtatc     60
tcgtgtagcg gcgataatct tggtgattat tatgcttctt ggtaccagca gaaacccggg    120
caggcgccag ttcttgtgat ttatgatgat tctaatcgtc cctcaggcat cccggaacgc    180
tttagcggat ccaacagcgg caacaccgcg accctgacca ttagcggcac tcaggcggaa    240
gacgaagcgg attattattg ccagacttgg gatggtactc ttcattttgt gtttggcggc    300
ggcacgaagt taaccgttct tggtcagccc aaggctgccc cctcggtcac tctgttccca    360
cccctcctct gaggagcttca agccaacaag gccacactgg tgtgtctcat aagtgacttc    420
tacccgggag ccgtgacagt ggcctggaag gcagatagca gccccgtcaa ggcgggagtg    480
gagaccacca caccctccaa acaaagcaac aacaagtacg cggccagcag ctacctgagc    540
ctgacgcctg agcagtggaa gtccacagaa agctacagct gccaggtcac gcatgaaggg    600
agcaccgtgg agaagacagt ggcccctaca gaatgttca                          639

<210> SEQ ID NO 15
<211> LENGTH: 6
<212> TYPE: PRT
<213> ORGANISM: Homo sapien

<400> SEQUENCE: 15

Ser Asp Tyr Tyr Met His
1               5

<210> SEQ ID NO 16
<211> LENGTH: 17
<212> TYPE: PRT
<213> ORGANISM: Homo sapien

<400> SEQUENCE: 16

Val Ile Ser Gly Ser Gly Ser Asn Thr Tyr Tyr Ala Asp Ser Val Lys
1               5                   10                  15
Gly

<210> SEQ ID NO 17
<211> LENGTH: 10
<212> TYPE: PRT
<213> ORGANISM: Homo sapien

<400> SEQUENCE: 17

Arg Leu Tyr Ala Gln Phe Glu Gly Asp Phe
1               5                   10

<210> SEQ ID NO 18
<211> LENGTH: 118
<212> TYPE: PRT
<213> ORGANISM: Homo sapien

<400> SEQUENCE: 18
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met His Trp Val Arg Gln Ala Pro Gly Lys Gly Leu Glu Trp Val
        35                  40                  45

Ser Val Ile Ser Gly Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Ala Gln Phe Glu Gly Asp Phe Trp Gly Gln Gly Thr
            100                 105                 110

Leu Val Thr Val Ser Ser
        115

<210> SEQ ID NO 19
<211> LENGTH: 444
<212> TYPE: PRT
<213> ORGANISM: Homo sapien

<400> SEQUENCE: 19

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met His Trp Val Arg Gln Ala Pro Gly Lys Gly Leu Glu Trp Val
        35                  40                  45

Ser Val Ile Ser Gly Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Ala Gln Phe Glu Gly Asp Phe Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

```
Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 20
<211> LENGTH: 11
<212> TYPE: PRT
<213> ORGANISM: Homo sapien

<400> SEQUENCE: 20

Ser Gly Asp Asn Ile Gly Ser Lys Tyr Val Ser
1               5                   10

<210> SEQ ID NO 21
<211> LENGTH: 7
<212> TYPE: PRT
<213> ORGANISM: Homo sapien

<400> SEQUENCE: 21

Ser Asp Ser Glu Arg Pro Ser
1               5

<210> SEQ ID NO 22
<211> LENGTH: 10
<212> TYPE: PRT
<213> ORGANISM: Homo sapien

<400> SEQUENCE: 22

Gln Ser Trp Asp Gly Ser Ile Ser Arg Val
1               5                   10

<210> SEQ ID NO 23
<211> LENGTH: 107
<212> TYPE: PRT
<213> ORGANISM: Homo sapien

<400> SEQUENCE: 23

Asp Ile Glu Leu Thr Gln Pro Pro Ser Val Ser Val Ala Pro Gly Gln
1               5                   10                  15
```

Thr Ala Arg Ile Ser Cys Ser Gly Asp Asn Ile Gly Ser Lys Tyr Val
        20                  25                  30

Ser Trp Tyr Gln Gln Lys Pro Gly Gln Ala Pro Val Leu Val Ile Tyr
        35                  40                  45

Ser Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Gly Ser Ile Ser Arg
                85                  90                  95

Val Phe Gly Gly Gly Thr Lys Leu Thr Val Leu
                100                 105

<210> SEQ ID NO 24
<211> LENGTH: 213
<212> TYPE: PRT
<213> ORGANISM: Homo sapien

<400> SEQUENCE: 24

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Lys Tyr Val
            20                  25                  30

Ser Trp Tyr Gln Gln Lys Pro Gly Gln Ala Pro Val Leu Val Ile Tyr
        35                  40                  45

Ser Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Gly Ser Ile Ser Arg
                85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
                180                 185                 190

Ser Cys Gln Val Thr His Glu Gly Ser Thr Val Glu Lys Thr Val Ala
            195                 200                 205

Pro Thr Glu Cys Ser
        210

<210> SEQ ID NO 25
<211> LENGTH: 354
<212> TYPE: DNA
<213> ORGANISM: Homo sapien

<400> SEQUENCE: 25
caggtgcaat tggtggaaag cggcggcggc ctggtgcaac cgggcggcag cctgcgtctg    60
agctgcgcgg cctccggatt taccttttct gattattata tgcattgggt gcgccaagcc   120

```
cctgggaagg gtctcgagtg ggtgagcgtt atctctggtt ctggtagcaa tacctattat    180
gcggatagcg tgaaaggccg ttttaccatt tcacgtgata attcgaaaaa cacctgtat    240 ctgcaaatga acagcctgcg tgcggaagat acggccgtgt attattgcgc gcgtctttat    300
gctcagtttg agggtgattt ttggggccaa ggcaccctgg tgacggttag ctca         354

<210> SEQ ID NO 26
<211> LENGTH: 327
<212> TYPE: DNA
<213> ORGANISM: Homo sapien

<400> SEQUENCE: 26
gatatcgaac tgacccagcc gccttcagtg agcgttgcac caggtcagac cgcgcgtatc    60
tcgtgtagcg gcgataatat tggttctaag tatgtttctt ggtaccagca gaaacccggg   120
caggcgccag ttcttgtgat ttattctgat tctgagcgtc cctcaggcat cccggaacgc   180
tttagcggat ccaacagcgg caacaccgcg accctgacca ttagcggcac tcaggcggaa   240
gacgaagcgg attattattg ccagtcttgg gatggttcta tttctcgtgt gtttggcggc   300
ggcacgaagt taaccgtcct aggtcag                                       327

<210> SEQ ID NO 27
<211> LENGTH: 1332
<212> TYPE: DNA
<213> ORGANISM: Homo sapien

<400> SEQUENCE: 27
caggtgcaat tggtggaaag cggcggcggc ctggtgcaac cgggcggcag cctgcgtctg    60
agctgcgcgg cctccggatt tacctttct gattattata tgcattgggt gcgccaagcc   120
cctgggaagg gtctcgagtg ggtgagcgtt atctctggtt ctggtagcaa tacctattat   180
gcggatagcg tgaaaggccg ttttaccatt tcacgtgata attcgaaaaa cacctgtat   240 ctgcaaatga acagcctgcg tgcggaagat acggccgtgt attattgcgc gcgtctttat   300
gctcagtttg agggtgattt ttggggccaa ggcaccctgg tgacggttag ctcagcctcc   360
accaagggcc catcggtctt ccccctggcg ccctgctcca ggagcacctc cgagagcaca   420
gcggccctgg gctgcctggt caaggactac ttccccgaac cggtgacggt gtcgtggaac   480
tcaggcgctc tgaccagcgg cgtgcacacc ttcccggctg tcctacagtc ctcaggactc   540
tactccctca gcagcgtagt gaccgtgccc tccagcaact tcggcaccca gacctacacc   600
tgcaacgtag atcacaagcc cagcaacacc aaggtggaca gacagttgag cgcaaatgt   660 tgtgtcgagt gcccaccgtg cccagcacca cctgtggcag gaccgtcagt cttcctcttc   720 ccccaaaac ccaaggacac cctcatgatc tcccggaccc ctgaggtcac gtgcgtggtg    780
gtggacgtga gccacgaaga ccccgaggtc cagttcaact ggtacgtgga cggcgtggag   840
gtgcataatg ccaagacaaa gccacgggag gagcagttca cagcacgtt ccgtgtggtc    900 agcgtcctca ccgtcgtgca ccaggactgg ctgaacggca aggagtacaa gtgcaaggtc    960
tccaacaaag gctccccagc ccccatcgag aaaaccatct ccaaaaccaa agggcagccc   1020
cgagaaccac aggtgtacac cctgccccca tcccgggagg agatgaccaa gaaccaggtc   1080
agcctgacct gcctggtcaa aggcttctac cccagcgaca tcgccgtgga gtgggagagc   1140
aatgggcagc cggagaacaa ctacaagacc acacctccca tgctggactc cgacggctcc   1200
ttcttcctct acagcaagct caccgtggac aagagcaggt ggcagcaggg gaacgtcttc   1260
tcatgctccg tgatgcatga ggctctgcac aaccactaca cacagaagag cctctccctg   1320
```

```
tctccgggta aa                                                        1332

<210> SEQ ID NO 28
<211> LENGTH: 327
<212> TYPE: DNA
<213> ORGANISM: Homo sapien

<400> SEQUENCE: 28
gatatcgaac tgacccagcc gccttcagtg agcgttgcac caggtcagac cgcgcgtatc      60
tcgtgtagcg gcgataatat tggttctaag tatgtttctt ggtaccagca gaaacccggg     120
caggcgccag ttcttgtgat ttattctgat tctgagcgtc cctcaggcat cccggaacgc     180
tttagcggat ccaacagcgg caacaccgcg accctgacca ttagcggcac tcaggcggaa     240
gacgaagcgg attattattg ccagtcttgg gatggttcta tttctcgtgt gtttggcggc     300
ggcacgaagt taaccgtcct aggtcag                                         327

<210> SEQ ID NO 29
<211> LENGTH: 6
<212> TYPE: PRT
<213> ORGANISM: Homo sapien

<400> SEQUENCE: 29

Ser Thr Tyr Trp Ile Ser
1               5

<210> SEQ ID NO 30
<211> LENGTH: 17
<212> TYPE: PRT
<213> ORGANISM: Homo sapien

<400> SEQUENCE: 30

Lys Ile Tyr Pro Gly Asp Ser Tyr Thr Asn Tyr Ser Pro Ser Phe Gln
1               5                   10                  15

Gly

<210> SEQ ID NO 31
<211> LENGTH: 8
<212> TYPE: PRT
<213> ORGANISM: Homo sapien

<400> SEQUENCE: 31

Arg Gly Tyr Gly Ile Phe Asp Tyr
1               5

<210> SEQ ID NO 32
<211> LENGTH: 116
<212> TYPE: PRT
<213> ORGANISM: Homo sapien

<400> SEQUENCE: 32

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 33
<211> LENGTH: 442
<212> TYPE: PRT
<213> ORGANISM: Homo sapien

<400> SEQUENCE: 33

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335
```

```
Gln Pro Arg Glu Pro Gln Val Tyr Thr Leu Pro Pro Ser Arg Glu Glu
                340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
                420                 425                 430

Gln Lys Ser Leu Ser Leu Ser Pro Gly Lys
            435                 440

<210> SEQ ID NO 34
<211> LENGTH: 11
<212> TYPE: PRT
<213> ORGANISM: Homo sapien

<400> SEQUENCE: 34

Ser Gly Asp Asn Ile Gly Asp Gln Tyr Ala His
1               5                   10

<210> SEQ ID NO 35
<211> LENGTH: 7
<212> TYPE: PRT
<213> ORGANISM: Homo sapien

<400> SEQUENCE: 35

Gln Asp Lys Asn Arg Pro Ser
1               5

<210> SEQ ID NO 36
<211> LENGTH: 11
<212> TYPE: PRT
<213> ORGANISM: Homo sapien

<400> SEQUENCE: 36

Ala Thr Tyr Thr Gly Phe Gly Ser Leu Ala Val
1               5                   10

<210> SEQ ID NO 37
<211> LENGTH: 108
<212> TYPE: PRT
<213> ORGANISM: Homo sapien

<400> SEQUENCE: 37

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asp Gln Tyr Ala
            20                  25                  30

His Trp Tyr Gln Gln Lys Pro Gly Gln Ala Pro Val Val Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Thr Tyr Thr Gly Phe Gly Ser Leu
                85                  90                  95
```

Ala Val Phe Gly Gly Gly Thr Lys Leu Thr Val Leu
            100                 105

<210> SEQ ID NO 38
<211> LENGTH: 214
<212> TYPE: PRT
<213> ORGANISM: Homo sapien

<400> SEQUENCE: 38

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asp Gln Tyr Ala
            20                  25                  30

His Trp Tyr Gln Gln Lys Pro Gly Gln Ala Pro Val Val Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 39
<211> LENGTH: 348
<212> TYPE: DNA
<213> ORGANISM: Homo sapien

<400> SEQUENCE: 39
caggtgcaat tggttcagag cggcgcggaa gtgaaaaaac cgggcgaaag cctgaaaatt      60
agctgcaaag gttccggata ttcctttttct acttattgga tttcttgggt gcgccagatg    120
cctgggaagg gtctcgagtg gatgggcaag atctatccgg gtgatagcta taccaattat    180
tctccgagct ttcagggcca ggtgactatt agcgcggata aaagcattag caccgcgtat    240
cttcaatgga gcagcctgaa agcgagcgat acggccatgt attattgtgc gcgtggttat    300
ggtatttttg attattgggg ccaaggcacc ctggtcaccg tctcctca                  348

<210> SEQ ID NO 40
<211> LENGTH: 324
<212> TYPE: DNA
<213> ORGANISM: Homo sapien

```
<400> SEQUENCE: 40
gatatcgaac tgacccagcc gccttcagtg agcgttgcac caggtcagac cgcgcgtatc      60
tcgtgtagcg gcgataatat tggtgatcag tatgctcatt ggtaccagca gaaacccggg     120
caggcgccag ttgttgtgat ttatcaggat aagaatcgtc cctcaggcat cccggaacgc     180
tttagcggat ccaacagcgg caacaccgcg accctgacca ttagcggcac tcaggcggaa     240
gacgaagcgg attattattg cgctacttat actggttttg gttctcttgc tgtgtttggc     300
ggcggcacga agttaaccgt ccta                                            324

<210> SEQ ID NO 41
<211> LENGTH: 1326
<212> TYPE: DNA
<213> ORGANISM: Homo sapien

<400> SEQUENCE: 41
caggtgcaat tggttcagag cggcgcggaa gtgaaaaaac cgggcgaaag cctgaaaatt      60
agctgcaaag gttccggata ttcctttttct acttattgga tttcttgggt gcgccagatg    120
cctgggaagg gtctcgagtg gatgggcaag atctatccgg gtgatagcta taccaattat     180
tctccgagct ttcagggcca ggtgactatt agcgcggata aaagcattag caccgcgtat     240
cttcaatgga gcagcctgaa agcgagcgat acggccatgt attattgtgc gcgtggttat     300
ggtatttttg attattgggg ccaaggcacc ctggtcaccg tctcctcagc tccaccaag     360 ggcccatcgg tcttccccct ggcgccctgc tccaggagca cctccgagag cacagcggcc     420
ctgggctgcc tggtcaagga ctacttcccc gaaccggtga cggtgtcgtg aactcaggc     480 gctctgacca gcggcgtgca caccttcccg gctgtcctac agtcctcagg actctactcc     540
ctcagcagcg tagtgaccgt gccctccagc aacttcggca cccagaccta cacctgcaac     600
gtagatcaca gcccagcaa caccaaggtg gacaagacag ttgagcgcaa atgttgtgtc     660
gagtgcccac cgtgcccagc accacctgtg gcaggaccgt cagtcttcct cttcccccca     720
aaacccaagg acaccctcat gatctcccgg accctgagg tcacgtgcgt ggtggtggac     780
gtgagccacg aagaccccga ggtccagttc aactggtacg tggacggcgt ggaggtgcat     840
aatgccaaga caaagccacg ggaggagcag ttcaacagca cgttccgtgt ggtcagcgtc     900
ctcaccgtcg tgcaccagga ctggctgaac ggcaaggagt acaagtgcaa ggtctccaac     960
aaaggcctcc cagcccccat cgagaaaacc atctccaaaa ccaaagggca gccccgagaa    1020
ccacaggtgt acaccctgcc cccatcccgg gaggagatga ccaagaacca ggtcagcctg    1080
acctgcctgg tcaaaggctt ctaccccagc gacatcgccg tggagtggga gagcaatggg    1140
cagccggaga caactacaa gaccacacct cccatgctgg actccgacgg ctccttcttc     1200
ctctacagca agctcaccgt ggacaagagc aggtggcagc aggggaacgt cttctcatgc    1260
tccgtgatgc atgaggctct gcacaaccac tacacacaga gagcctctc cctgtctccg    1320 ggtaaa                                                               1326

<210> SEQ ID NO 42
<211> LENGTH: 324
<212> TYPE: DNA
<213> ORGANISM: Homo sapien

<400> SEQUENCE: 42
gatatcgaac tgacccagcc gccttcagtg agcgttgcac caggtcagac cgcgcgtatc      60
tcgtgtagcg gcgataatat tggtgatcag tatgctcatt ggtaccagca gaaacccggg     120
```

```
caggcgccag ttgttgtgat ttatcaggat aagaatcgtc cctcaggcat cccggaacgc      180
tttagcggat ccaacagcgg caacaccgcg accctgacca ttagcggcac tcaggcggaa      240
gacgaagcgg attattattg cgctacttat actggttttg gttctcttgc tgtgtttggc      300
ggcggcacga agttaaccgt ccta                                              324
```

<210> SEQ ID NO 43
<211> LENGTH: 116
<212> TYPE: PRT
<213> ORGANISM: Homo sapien

<400> SEQUENCE: 43

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115
```

<210> SEQ ID NO 44
<211> LENGTH: 442
<212> TYPE: PRT
<213> ORGANISM: Homo sapien

<400> SEQUENCE: 44

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
            195                 200                 205

Lys Val Asp Lys Thr Val Glu Arg Lys Cys Cys Val Glu Cys Pro Pro
            210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Phe Arg Val Val Ser Val Leu Thr Val Val
            290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
            325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440

<210> SEQ ID NO 45
<211> LENGTH: 108
<212> TYPE: PRT
<213> ORGANISM: Homo sapien

<400> SEQUENCE: 45

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
            35                  40                  45

Gln Asp Lys Asn Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
            85                  90                  95

Ala Val Phe Gly Gly Gly Thr Lys Leu Thr Val Leu
            100                 105
```

```
<210> SEQ ID NO 46
<211> LENGTH: 214
<212> TYPE: PRT
<213> ORGANISM: Homo sapien

<400> SEQUENCE: 46

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 47
<211> LENGTH: 348
<212> TYPE: DNA
<213> ORGANISM: Homo sapien

<400> SEQUENCE: 47
gaggtgcaat tggttcagag cggcgcggaa gtgaaaaaac cgggcgaaag cctgaggatt     60
agctgcaaag gttccggata ttcctttttct acttattgga tttcttgggt gcgccagatg   120
cctgggaagg gtctcgagtg gatgggcaag atctatccgg gtgatagcta taccaattat   180
tctccgagct ttcagggcca ggtgactatt agcgcggata aaagcattag caccgcgtat   240
cttcaatgga gcagcctgaa agcgagcgat acggccatgt attattgtgc gcgtggttat   300
ggtatttttg attattgggg ccaaggcacc ctggtcaccg tctcctca              348

<210> SEQ ID NO 48
<211> LENGTH: 324
<212> TYPE: DNA
<213> ORGANISM: Homo sapien

<400> SEQUENCE: 48
agctacgagc tgacccagcc ccccagcgtg tccgtgagcc ctggccagac cgccagcatc     60
```

```
acctgcagcg gcgacaacat cggcgaccag tacgcccact ggtatcagca gaagcccggc    120
cagagccccg tgctggtgat ctaccaggac aagaaccggc ccagcggcat ccccgagcgg    180
ttcagcggca gcaacagcgg caacaccgcc accctgacca tcagcggcac ccaggccatg    240
gacgaggccg actactactg cgccacctac accggcttcg gcagcctggc cgtgttcggc    300
ggagggacca agctgaccgt ccta                                           324

<210> SEQ ID NO 49
<211> LENGTH: 1326
<212> TYPE: DNA
<213> ORGANISM: Homo sapien

<400> SEQUENCE: 49
gaggtgcaat tggttcagag cggcgcggaa gtgaaaaaac cgggcgaaag cctgaggatt     60
agctgcaaag gttccggata ttccttttct acttattgga tttcttgggt gcgccagatg    120
cctgggaagg gtctcgagtg gatgggcaag atctatccgg gtgatagcta taccaattat    180
tctccgagct ttcagggcca ggtgactatt agcgcggata aaagcattag caccgcgtat    240
cttcaatgga gcagcctgaa agcgagcgat acggccatgt attattgtgc gcgtggttat    300 ggtattttg attattgggg ccaaggcacc ctggtcaccg tctcctcagc ctccaccaag    360
ggcccatcgg tcttccccct ggcgccctgc tccaggagca cctccgagag cacagcggcc    420
ctgggctgcc tggtcaagga ctacttcccc gaaccggtga cggtgtcgtg gaactcaggc    480
gctctgacca gcggcgtgca caccttcccg gctgtcctac agtcctcagg actctactcc    540
ctcagcagcg tagtgaccgt gccctccagc aacttcggca cccagaccta cacctgcaac    600
gtagatcaca gcccagcaa caccaaggtg gacaagacag ttgagcgcaa atgttgtgtc    660
gagtgcccac cgtgcccagc accacctgtg gcaggaccgt cagtcttcct cttcccccca    720
aaacccaagg acaccctcat gatctcccgg acccctgagg tcacgtgcgt ggtggtggac    780
gtgagccacg aagaccccga ggtccagttc aactggtacg tggacggcgt ggaggtgcat    840
aatgccaaga caaagccacg ggaggagcag ttcaacagca cgttccgtgt ggtcagcgtc    900
ctcaccgtcg tgcaccagga ctggctgaac ggcaaggagt acaagtgcaa ggtctccaac    960
aaaggcctcc cagcccccat cgagaaaacc atctccaaaa ccaaagggca gccccgagaa   1020
ccacaggtgt acaccctgcc cccatcccgg gaggagatga ccaagaacca ggtcagcctg   1080
acctgcctgg tcaaaggctt ctaccccagc gacatcgccg tggagtggga gagcaatggg   1140
cagccggaga acaactacaa gaccacacct cccatgctgg actccgacgg ctccttcttc   1200
ctctacagca agctcaccgt ggacaagagc aggtggcagc aggggaacgt cttctcatgc   1260
tccgtgatgc atgaggctct gcacaaccac tacacacaga gagcctctc cctgtctccg   1320 ggtaaa                                                              1326

<210> SEQ ID NO 50
<211> LENGTH: 642
<212> TYPE: DNA
<213> ORGANISM: Homo sapien

<400> SEQUENCE: 50
agctacgagc tgacccagcc ccccagcgtg tccgtgagcc ctggccagac cgccagcatc     60
acctgcagcg gcgacaacat cggcgaccag tacgcccact ggtatcagca gaagcccggc    120
cagagccccg tgctggtgat ctaccaggac aagaaccggc ccagcggcat ccccgagcgg    180
ttcagcggca gcaacagcgg caacaccgcc accctgacca tcagcggcac ccaggccatg    240
```

```
gacgaggccg actactactg cgccacctac accggcttcg gcagcctggc cgtgttcggc    300
ggagggacca agctgaccgt cctaggtcag cccaaggctg ccccctcggt cactctgttc    360
ccacccctcc ctgaggagct tcaagccaac aaggccacac tggtgtgtct cataagtgac    420
ttctacccgg gagccgtgac agtggcctgg aaggcagata gcagcccgt caaggcggga     480 gtggagacca ccacaccctc caaacaaagc aacaacaagt acgcggccag cagctacctg    540
agcctgacgc tgagcagtg gaagtcccac agaagctaca gctgccaggt cacgcatgaa     600
gggagcaccg tggagaagac agtggcccct acagaatgtt ca                      642
```

```
<210> SEQ ID NO 51
<211> LENGTH: 108
<212> TYPE: PRT
<213> ORGANISM: Homo sapien

<400> SEQUENCE: 51

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Val Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 52
<211> LENGTH: 214
<212> TYPE: PRT
<213> ORGANISM: Homo sapien

<400> SEQUENCE: 52

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Val Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
```

```
                      145                 150                 155                 160
Val Glu Thr Thr Thr Pro Ser Lys Gln Ser Asn Asn Lys Tyr Ala Ala
                165                 170                 175
Ser Ser Tyr Leu Ser Leu Thr Pro Glu Gln Trp Lys Ser His Arg Ser
            180                 185                 190
Tyr Ser Cys Gln Val Thr His Glu Gly Ser Thr Val Glu Lys Thr Val
        195                 200                 205
Ala Pro Thr Glu Cys Ser
    210

<210> SEQ ID NO 53
<211> LENGTH: 324
<212> TYPE: DNA
<213> ORGANISM: Homo sapien

<400> SEQUENCE: 53
agctacgagc tgacccagcc ccccagcgtg tccgtgagcc ctggccagac cgccagcatc      60
acctgcagcg gcgacaacat cggcgaccag tacgcccact ggtatcagca gaagcccggc     120
cagagccccg tggtggtgat ctaccaggac aagaaccggc ccagcggcat ccccgagcgg     180
ttcagcggca gcaacagcgg caacaccgcc accctgacca tcagcggcac ccaggccatg     240
gacgaggccg actactactg cgccacctac accggcttcg gcagcctggc cgtgttcggc     300
ggagggacca agctgaccgt ccta                                             324

<210> SEQ ID NO 54
<211> LENGTH: 642
<212> TYPE: DNA
<213> ORGANISM: Homo sapien

<400> SEQUENCE: 54
agctacgagc tgacccagcc ccccagcgtg tccgtgagcc ctggccagac cgccagcatc      60
acctgcagcg gcgacaacat cggcgaccag tacgcccact ggtatcagca gaagcccggc     120
cagagccccg tggtggtgat ctaccaggac aagaaccggc ccagcggcat ccccgagcgg     180
ttcagcggca gcaacagcgg caacaccgcc accctgacca tcagcggcac ccaggccatg     240
gacgaggccg actactactg cgccacctac accggcttcg gcagcctggc cgtgttcggc     300
ggagggacca agctgaccgt cctaggtcag cccaaggctg ccccctcggt cactctgttc     360
ccaccctcct ctgaggagct tcaagccaac aaggccacac tggtgtgtct cataagtgac     420
ttctacccgg gagccgtgac agtggcctgg aaggcagata gcagccccgt caaggcggga     480
gtggagacca ccacaccctc aaacaaagc aacaacaagt acgcggccag cagctacctg     540
agcctgacgc ctgagcagtg gaagtcccac agaagctaca gctgccaggt cacgcatgaa     600
gggagcaccg tggagaagac agtggcccct acagaatgtt ca                        642

<210> SEQ ID NO 55
<211> LENGTH: 11
<212> TYPE: PRT
<213> ORGANISM: Homo sapien

<400> SEQUENCE: 55

Ser Thr Tyr Thr Phe Val Gly Phe Thr Thr Val
1               5                   10

<210> SEQ ID NO 56
<211> LENGTH: 108
<212> TYPE: PRT
<213> ORGANISM: Homo sapien
```

<400> SEQUENCE: 56

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asp Gln Tyr Ala
            20                  25                  30

His Trp Tyr Gln Gln Lys Pro Gly Gln Ala Pro Val Val Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Thr Tyr Thr Phe Val Gly Phe Thr
                85                  90                  95

Thr Val Phe Gly Gly Gly Thr Lys Leu Thr Val Leu
            100                 105

<210> SEQ ID NO 57
<211> LENGTH: 214
<212> TYPE: PRT
<213> ORGANISM: Homo sapien

<400> SEQUENCE: 57

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asp Gln Tyr Ala
            20                  25                  30

His Trp Tyr Gln Gln Lys Pro Gly Gln Ala Pro Val Val Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Thr Tyr Thr Phe Val Gly Phe Thr
                85                  90                  95

Thr Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 58
<211> LENGTH: 324
<212> TYPE: DNA
<213> ORGANISM: Homo sapien

<400> SEQUENCE: 58

```
gatatcgaac tgacccagcc gccttcagtg agcgttgcac caggtcagac cgcgcgtatc    60
tcgtgtagcg gcgataatat tggtgatcag tatgctcatt ggtaccagca gaaacccggg   120
caggcgccag ttgttgtgat ttatcaggat aagaatcgtc cctcaggcat cccggaacgc   180
tttagcggat ccaacagcgg caacaccgcg accctgacca ttagcggcac tcaggcggaa   240
gacgaagcgg attattattg ctctacttat acttttgttg gttttactac tgtgtttggc   300
ggcggcacga agttaaccgt ccta                                          324
```

<210> SEQ ID NO 59
<211> LENGTH: 642
<212> TYPE: DNA
<213> ORGANISM: Homo sapien

<400> SEQUENCE: 59

```
gatatcgaac tgacccagcc gccttcagtg agcgttgcac caggtcagac cgcgcgtatc    60
tcgtgtagcg gcgataatat tggtgatcag tatgctcatt ggtaccagca gaaacccggg   120
caggcgccag ttgttgtgat ttatcaggat aagaatcgtc cctcaggcat cccggaacgc   180
tttagcggat ccaacagcgg caacaccgcg accctgacca ttagcggcac tcaggcggaa   240
gacgaagcgg attattattg ctctacttat acttttgttg gttttactac tgtgtttggc   300
ggcggcacga agttaaccgt cctaggtcag cccaaggctg cccctcggt cactctgttc    360
ccacccctcct ctgaggagct tcaagccaac aaggccacac tggtgtgtct cataagtgac   420
ttctacccgg gagccgtgac agtggcctgg aaggcagata gcagcccgt caaggcggga    480
gtggagacca ccacccctc caaacaaagc aacaacaagt acgcggccag cagctacctg    540
agcctgacgc ctgagcagtg gaagtcccac agaagctaca gctgccaggt cacgcatgaa    600
gggagcaccg tggagaagac agtggcccct acagaatgtt ca                      642
```

<210> SEQ ID NO 60
<211> LENGTH: 108
<212> TYPE: PRT
<213> ORGANISM: Homo sapien

<400> SEQUENCE: 60

```
Ser Tyr Glu Leu Thr Gln Pro Pro Ser Val Ser Val Ser Pro Gly Gln
  1               5                  10                  15

Thr Ala Ser Ile Thr Cys Ser Gly Asp Asn Ile Gly Asp Gln Tyr Ala
             20                  25                  30

His Trp Tyr Gln Gln Lys Pro Gly Gln Ser Pro Val Leu Val Ile Tyr
         35                  40                  45

Gln Asp Lys Asn Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Ser Thr Tyr Thr Phe Val Gly Phe Thr
                 85                  90                  95

Thr Val Phe Gly Gly Gly Thr Lys Leu Thr Val Leu
            100                 105
```

<210> SEQ ID NO 61
<211> LENGTH: 214
<212> TYPE: PRT
<213> ORGANISM: Homo sapien

<400> SEQUENCE: 61

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Thr Tyr Thr Phe Val Gly Phe Thr
                85                  90                  95

Thr Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 62
<211> LENGTH: 324
<212> TYPE: DNA
<213> ORGANISM: Homo sapien

<400> SEQUENCE: 62
agctacgagc tgacccagcc ccccagcgtg tccgtgagcc ctggccagac cgccagcatc        60
acctgcagcg gcgacaacat cggcgaccag tacgcccact ggtatcagca gaagcccggc       120
cagagccccg tgctggtgat ctaccaggac aagaaccggc ccagcggcat ccccgagcgg       180
ttcagcggca gcaacagcgg caacaccgcc accctgacca tcagcggcac ccaggccatg       240
gacgaggccg actactactg ctctacttat acttttgttg gttttactac tgtgttcggc       300
ggagggacca agctgaccgt ccta                                              324

<210> SEQ ID NO 63
<211> LENGTH: 642
<212> TYPE: DNA
<213> ORGANISM: Homo sapien

<400> SEQUENCE: 63
agctacgagc tgacccagcc ccccagcgtg tccgtgagcc ctggccagac cgccagcatc        60
acctgcagcg gcgacaacat cggcgaccag tacgcccact ggtatcagca gaagcccggc       120
cagagccccg tgctggtgat ctaccaggac aagaaccggc ccagcggcat ccccgagcgg       180
ttcagcggca gcaacagcgg caacaccgcc accctgacca tcagcggcac ccaggccatg       240
gacgaggccg actactactg ctctacttat acttttgttg gttttactac tgtgttcggc       300

```
ggagggacca agctgaccgt cctaggtcag cccaaggctg cccctcggt cactctgttc    360 ccaccctcct ctgaggagct tcaagccaac aaggccacac tggtgtgtct cataagtgac    420
ttctacccgg gagccgtgac agtggcctgg aaggcagata gcagcccgt caaggcggga    480 gtggagacca ccacaccctc caaacaaagc aacaacaagt acgcggccag cagctacctg    540
agcctgacgc ctgagcagtg gaagtcccac agaagctaca gctgccaggt cacgcatgaa    600
gggagcaccg tggagaagac agtggcccct acagaatgtt ca                      642
```

<210> SEQ ID NO 64
<211> LENGTH: 108
<212> TYPE: PRT
<213> ORGANISM: Homo sapien

<400> SEQUENCE: 64

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Val Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Thr Tyr Thr Phe Val Gly Phe Thr
                85                  90                  95

Thr Val Phe Gly Gly Gly Thr Lys Leu Thr Val Leu
            100                 105

<210> SEQ ID NO 65
<211> LENGTH: 214
<212> TYPE: PRT
<213> ORGANISM: Homo sapien

<400> SEQUENCE: 65

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Val Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Thr Tyr Thr Phe Val Gly Phe Thr
                85                  90                  95

Thr Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

```
Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210
```

```
<210> SEQ ID NO 66
<211> LENGTH: 324
<212> TYPE: DNA
<213> ORGANISM: Homo sapien

<400> SEQUENCE: 66
```

```
agctacgagc tgacccagcc ccccagcgtg tccgtgagcc ctggccagac cgccagcatc      60
acctgcagcg gcgacaacat cggcgaccag tacgcccact ggtatcagca gaagcccggc     120
cagagccccg tggtggtgat ctaccaggac aagaaccggc ccagcggcat ccccgagcgg     180
ttcagcggca gcaacagcgg caacaccgcc accctgacca tcagcggcac ccaggccatg     240
gacgaggccg actactactg ctctacttat acttttgttg gttttactac tgtgttcggc     300
ggagggacca agctgaccgt ccta                                            324
```

```
<210> SEQ ID NO 67
<211> LENGTH: 642
<212> TYPE: DNA
<213> ORGANISM: Homo sapien

<400> SEQUENCE: 67
```

```
agctacgagc tgacccagcc ccccagcgtg tccgtgagcc ctggccagac cgccagcatc      60
acctgcagcg gcgacaacat cggcgaccag tacgcccact ggtatcagca gaagcccggc     120
cagagccccg tggtggtgat ctaccaggac aagaaccggc ccagcggcat ccccgagcgg     180
ttcagcggca gcaacagcgg caacaccgcc accctgacca tcagcggcac ccaggccatg     240
gacgaggccg actactactg ctctacttat acttttgttg gttttactac tgtgttcggc     300
ggagggacca agctgaccgt cctaggtcag cccaaggctg cccccctcgg tcactctgttc     360
ccaccctcct ctgaggagct tcaagccaac aaggccacac tggtgtgtct cataagtgac     420
ttctacccgg gagccgtgac agtggcctgg aaggcagata gcagccccgt caaggcggga     480
gtggagacca ccacaccctc caaacaaagc aacaacaagt acgcggccag cagctacctg     540
agcctgacgc ctgagcagtg gaagtcccac agaagctaca gctgccaggt cacgcatgaa     600
gggagcaccg tggagaagac agtggcccct acagaatgtt ca                        642
```

```
<210> SEQ ID NO 68
<211> LENGTH: 255
<212> TYPE: PRT
<213> ORGANISM: Homo sapien

<400> SEQUENCE: 68
```

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
```

```
                 50                  55                  60
Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                 85                  90                  95

Ala Gly Cys Ser Met Cys Glu Gln Asp Cys Lys Gln Gly Gln Glu Leu
                100                 105                 110

Thr Lys Lys Gly Cys Lys Asp Cys Cys Phe Gly Thr Phe Asn Asp Gln
                115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
                180                 185                 190

Ala Leu Thr Ser Thr Ala Leu Leu Phe Leu Leu Phe Phe Leu Thr Leu
                195                 200                 205

Arg Phe Ser Val Val Lys Arg Gly Arg Lys Lys Leu Leu Tyr Ile Phe
                210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 69
<211> LENGTH: 330
<212> TYPE: PRT
<213> ORGANISM: Homo sapien

<400> SEQUENCE: 69

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                 70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

His Gln Asp Trp Leu Asn Gly Lys Glu Tyr Lys Cys Lys Val Ser Asn
        180                 185                 190
Lys Ala Leu Pro Ala Pro Ile Glu Lys Thr Ile Ser Lys Ala Lys Gly
    195                 200                 205
Gln Pro Arg Glu Pro Gln Val Tyr Thr Leu Pro Pro Ser Arg Glu Glu
210                 215                 220
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 70
<211> LENGTH: 990
<212> TYPE: DNA
<213> ORGANISM: Homo sapien

<400> SEQUENCE: 70
gcctccacca agggcccatc ggtcttcccc ctggcaccct cctccaagag cacctctggg        60
ggcacagcgg ccctgggctg cctggtcaag gactacttcc ccgaaccggt gacggtgtcg       120
tggaactcag gcgccctgac cagcggcgtg cacaccttcc cggctgtcct acagtcctca       180
ggactctact ccctcagcag cgtagtgacc gtgccctcca gcagcttggg cacccagacc       240
tacatctgca acgtgaatca caagcccagc aacaccaagg tggacaagaa agttgagccc       300
aaatcttgtg acaaaactca cacatgccca ccgtgcccag cacctgaact cctgggggga       360
ccgtcagtct tcctcttccc cccaaaaccc aaggacaccc tcatgatctc ccggacccct       420
gaggtcacat gcgtggtggt ggacgtgagc cacgaagacc ctgaggtcaa gttcaactgg       480
tacgtggacg gcgtggaggt gcataatgcc aagacaaagc cgcgggagga gcagtacaac       540
agcacgtacc gtgtggtcag cgtcctcacc gtcctgcacc aggactggct gaatggcaag       600
gagtacaagt gcaaggtctc caacaaagcc ctcccagccc catcgagaa accatctcc       660
aaagccaaag gcagccccg agaaccacag gtgtacaccc tgcccccatc ccggaggag       720
atgaccaaga accaggtcag cctgacctgc ctggtcaaag gcttctatcc cagcgacatc       780
gccgtggagt gggagagcaa tgggcagccg gagaacaact acaagaccac gcctcccgtg       840
ctggactccg acggctcctt cttcctctat agcaagctca ccgtggacaa gagcaggtgg       900
cagcagggga acgtcttctc atgctccgtg atgcatgagg ctctgcacaa ccactacacg       960
cagaagagcc tctccctgtc tccgggtaaa                                       990

<210> SEQ ID NO 71
<211> LENGTH: 326
<212> TYPE: PRT
<213> ORGANISM: Homo sapien

<400> SEQUENCE: 71

Ala Ser Thr Lys Gly Pro Ser Val Phe Pro Leu Ala Pro Cys Ser Arg

```
               1               5                  10                 15
            Ser Thr Ser Glu Ser Thr Ala Ala Leu Gly Cys Leu Val Lys Asp Tyr
                             20                  25                  30

Phe Pro Glu Pro Val Thr Val Ser Trp Asn Ser Gly Ala Leu Thr Ser
                         35                  40                  45

Gly Val His Thr Phe Pro Ala Val Leu Gln Ser Ser Gly Leu Tyr Ser
                         50                  55                  60

Leu Ser Ser Val Val Thr Val Pro Ser Ser Asn Phe Gly Thr Gln Thr
             65                  70                  75                  80

Tyr Thr Cys Asn Val Asp His Lys Pro Ser Asn Thr Lys Val Asp Lys
                             85                  90                  95

Thr Val Glu Arg Lys Cys Cys Val Glu Cys Pro Pro Cys Pro Ala Pro
                            100                 105                 110

Pro Val Ala Gly Pro Ser Val Phe Leu Phe Pro Pro Lys Pro Lys Asp
                        115                 120                 125

Thr Leu Met Ile Ser Arg Thr Pro Glu Val Thr Cys Val Val Val Asp
                        130                 135                 140

Val Ser His Glu Asp Pro Glu Val Gln Phe Asn Trp Tyr Val Asp Gly
            145                 150                 155                 160

Val Glu Val His Asn Ala Lys Thr Lys Pro Arg Glu Glu Gln Phe Asn
                            165                 170                 175

Ser Thr Phe Arg Val Val Ser Val Leu Thr Val Val His Gln Asp Trp
                        180                 185                 190

Leu Asn Gly Lys Glu Tyr Lys Cys Lys Val Ser Asn Lys Gly Leu Pro
                        195                 200                 205

Ala Pro Ile Glu Lys Thr Ile Ser Lys Thr Lys Gly Gln Pro Arg Glu
                210                 215                 220

Pro Gln Val Tyr Thr Leu Pro Pro Ser Arg Glu Glu Met Thr Lys Asn
            225                 230                 235                 240

Gln Val Ser Leu Thr Cys Leu Val Lys Gly Phe Tyr Pro Ser Asp Ile
                            245                 250                 255

Ala Val Glu Trp Glu Ser Asn Gly Gln Pro Glu Asn Asn Tyr Lys Thr
                        260                 265                 270

Thr Pro Pro Met Leu Asp Ser Asp Gly Ser Phe Phe Leu Tyr Ser Lys
                        275                 280                 285

Leu Thr Val Asp Lys Ser Arg Trp Gln Gln Gly Asn Val Phe Ser Cys
                        290                 295                 300

Ser Val Met His Glu Ala Leu His Asn His Tyr Thr Gln Lys Ser Leu
            305                 310                 315                 320

Ser Leu Ser Pro Gly Lys
                        325

<210> SEQ ID NO 72
<211> LENGTH: 978
<212> TYPE: DNA
<213> ORGANISM: Homo sapien

<400> SEQUENCE: 72
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cggctgtcct acagtcctca     180
ggactctact ccctcagcag cgtagtgacc gtgccctcca gcaacttcgg cacccagacc     240
tacacctgca acgtagatca caagcccagc aacaccaagg tggacaagac agttgagcgc     300
```

```
aaatgttgtg tcgagtgccc accgtgccca gcaccacctg tggcaggacc gtcagtcttc      360
ctcttccccc caaaacccaa ggacaccctc atgatctccc ggaccctga ggtcacgtgc       420 gtggtggtgg acgtgagcca cgaagacccc gaggtccagt tcaactggta cgtggacggc      480
gtggaggtgc ataatgccaa gacaaagcca cgggaggagc agttcaacag cacgttccgt      540
gtggtcagcg tcctcaccgt cgtgcaccag gactggctga acggcaagga gtacaagtgc      600
aaggtctcca caaaggcct cccagccccc atcgagaaaa ccatctccaa aaccaaaggg       660
cagccccgag aaccacaggt gtacaccctg cccccatccc gggaggagat gaccaagaac      720
caggtcagcc tgacctgcct ggtcaaaggc ttctacccca gcgacatcgc cgtggagtgg      780
gagagcaatg ggcagccgga gaacaactac aagaccacac ctcccatgct ggactccgac      840
ggctccttct cctctacag caagctcacc gtggacaaga gcaggtggca gcaggggaac      900
gtcttctcat gctccgtgat gcatgaggct ctgcacaacc actacacaca gaagagcctc      960
tccctgtctc cgggtaaa                                                    978

<210> SEQ ID NO 73
<211> LENGTH: 106
<212> TYPE: PRT
<213> ORGANISM: Homo sapien

<400> SEQUENCE: 73

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 74
<211> LENGTH: 318
<212> TYPE: DNA
<213> ORGANISM: Homo sapien

<400> SEQUENCE: 74
ggtcagccca aggctgcccc ctcggtcact ctgttcccac cctcctctga ggagcttcaa       60
gccaacaagg ccacactggt gtgtctcata agtgacttct acccgggagc cgtgacagtg      120
gcctggaagg cagatagcag ccccgtcaag gcggagtgg agaccaccac acctccaaa       180 caaagcaaca caagtacgc ggccagcagc tacctgagcc tgacgcctga gcagtggaag      240
tcccacagaa gctacagctg ccaggtcacg catgaaggga gcaccgtgga aaagacagtg      300
gcccctacag aatgttca                                                    318
```

4-1BB BINDING MOLECULES

CROSS-REFERENCE TO RELATED APPLICATIONS

This application claims priority to U.S. Provisional Application No. 61/381,210 filed on Sep. 9, 2010, which is incorporated herein by reference in its entirety.

REFERENCE TO SEQUENCE LISTING

This application is being filed electronically via EFS-Web and includes an electronically submitted sequence listing in .txt format. The .txt file contains a sequence listing entitled "PC33845AUSSequenceListing_ST25.txt" created on Sep. 9, 2011 and having a size of 77 KB. The sequence listing contained in the .txt file is part of the specification and is herein incorporated by reference in its entirety.

FIELD OF THE INVENTION

The present disclosure relates to antibodies, and particularly antibodies that bind to human 4-1BB.

BACKGROUND 4-1BB (also referred to as CD137, TNFRSF9, etc) is a transmembrane protein of the Tumor Necrosis Factor receptor superfamily (TNFRS). Current understanding of 4-1BB indicates that expression is generally activation dependent and is present in a broad subset of immune cells including activated NK and NKT cells, regulatory T cells, dendritic cells (DC), stimulated mast cells, differentiating myeloid cells, monocytes, neutrophils, and eosinophils (Wang, 2009, Immunological Reviews 229: 192-215). 4-1BB expression has also been demonstrated on tumor vasculature (Broll, 2001, Amer. J. Clin. Pathol. 115(4):543-549; Seaman, 2007, Cancer Cell 11: 539-554) and at sites of inflamed or atherosclerotic endothelium (Drenkard, 2007 FASEB J. 21: 456-463; Olofsson, 2008, Circulation 117: 1292-1301). The ligand that stimulates 4-1BB, i.e., 4-1BB Ligand (4-1BBL), is expressed on activated antigen-presenting cells (APCs), myeloid progenitor cells, and hematopoietic stem cells.

Human 4-1BB is a 255 amino acid protein (Accession No. NM_001561; NP_001552). The complete human 4-1BB amino acid sequence is provided in SEQ ID NO:68. The protein comprises a signal sequence (amino acid residues 1-17), followed by an extracellular domain (169 amino acids), a transmembrane region (27 amino acids), and an intracellular domain (42 amino acids) (Cheuk ATC et al. 2004 Cancer Gene Therapy 11: 215-226). The receptor is expressed on the cell surface in monomer and dimer forms and likely trimerizes with 4-1BB ligand to signal.

Numerous studies of murine and human T cells indicate that 4-1BB promotes enhanced cellular proliferation, survival, and cytokine production (Croft, 2009, Nat Rev Immunol 9:271-285). Studies have indicated that some 4-1BB agonist mAbs increase costimulatory molecule expression and markedly enhance cytolytic T lymphocyte responses, resulting in anti-tumor efficacy in various models. 4-1BB agonist mAbs have demonstrated efficacy in prophylactic and therapeutic settings. Further, 4-1BB monotherapy and combination therapy tumor models have established durable anti-tumor protective T cell memory responses (Lynch, 2008, Immunol Rev. 22: 277-286). 4-1BB agonists also have been shown to inhibit autoimmune reactions in a variety of art-recognized autoimmunity models (Vinay, 2006, J Mol Med 84:726-736). This dual activity of 4-1BB offers the potential to provide anti-tumor activity while dampening autoimmune side effects that can be associated with immunotherapy approaches that break immune tolerance.

There is a long-felt unmet need for antibodies that bind human 4-1BB, increase a 4-1BB-mediated response, and thereby provide a potential therapeutic for treatment of various diseases and conditions, including cancer.

SUMMARY

It is an object of the disclosure to provide an isolated binding molecule that binds to human 4-1BB, such as an antibody or a binding fragment thereof, or derivative thereof. It is another object of the disclosure to provide a composition comprising a binding molecule that binds to 4-1BB. It is also an object of the present disclosure to provide methods for treating a disease and/or condition associated with or mediated by 4-1BB signaling by using one or more binding molecules of the disclosure. These and other objects of the disclosure are more fully described herein.

In some aspects, the disclosure provides isolated antibodies that bind to human 4-1BB.

In one particular aspect, the isolated antibody binds human 4-1BB at an epitope comprising amino acid residues 115-156 of SEQ ID NO: 68. In some particular embodiments, the antibody comprises the H-CDR1 amino acid sequence of SEQ ID NO: 29, H-CDR2 amino acid sequence of SEQ ID NO: 30, and H-CDR3 amino acid sequence of SEQ ID NO: 31. In other particular embodiments, the antibody comprises the L-CDR1 amino acid sequence of SEQ ID NO: 34, L-CDR2 amino acid sequence of SEQ ID NO: 35, and L-CDR3 amino acid sequence of SEQ ID NO: 36.

In another particular aspect, the isolated antibody binds human 4-1BB with a $K_D$ of 600 nM or less, 100 nM or less, 50 nM or less, 10 nM or less, 5 nM or less, or 1 nM or less, for the human 4-1BB extracellular domain as measured with the BIACore assay described in this disclosure.

In another particular aspect, the isolated antibody comprises: (a) an H-CDR1 as set forth in SEQ ID NO:1, SEQ ID NO:15, or SEQ ID NO:29; (b) an H-CDR2 as set forth in SEQ ID NO:2, SEQ ID NO:16, or SEQ ID NO:30; and (c) an H-CDR3 as set forth in SEQ ID NO:3, SEQ ID NO: 17, or SEQ ID NO:31.

In another particular aspect, the isolated antibody comprises: (a) an L-CDR1 as set forth in SEQ ID NO:6, SEQ ID NO: 20, or SEQ ID NO:34; (b) an L-CDR2 as set forth in SEQ ID NO:7, SEQ ID NO:21, or SEQ ID NO:35; and (c) an L-CDR3 as set forth in SEQ ID NO:8, SEQ ID NO:22, SEQ ID NO:36, or SEQ ID NO: 55.

In a further aspect, the isolated antibody comprises: (a) an H-CDR1 as set forth in SEQ ID NO:1, SEQ ID NO:15, or SEQ ID NO:29; (b) an H-CDR2 as set forth in SEQ ID NO:2, SEQ ID NO:16, or SEQ ID NO:30; and (c) an H-CDR3 as set forth in SEQ ID NO:3, SEQ ID NO: 17, or SEQ ID NO:31; and further comprises: (d) an L-CDR1 as set forth in SEQ ID NO:6, SEQ ID NO: 20, or SEQ ID NO:34; (e) an L-CDR2 as set forth in SEQ ID NO:7, SEQ ID NO:21, or SEQ ID NO:35; and (f) an L-CDR3 as set forth in SEQ ID NO:8, SEQ ID NO:22, SEQ ID NO:36, or SEQ ID NO: 55.

In some further particular aspects, the isolated antibody, is selected from the group consisting of:

(a) an antibody or antigen-binding portion thereof, comprising: an H-CDR1 as set forth in SEQ ID NO:1, an H-CDR2 as set forth in SEQ ID NO:2, and an H-CDR3 as set forth in SEQ ID NO:3;

(b) an antibody or antigen-binding portion thereof, comprising an H-CDR1 as set forth in SEQ ID NO:15, an H-CDR2 as set forth in SEQ ID NO:16, and an H-CDR3 as set forth in SEQ ID NO:17, and (c) an antibody or antigen-binding portion thereof, comprising an H-CDR1 as set forth in SEQ ID NO:29, an H-CDR2 as set forth in SEQ ID NO:30, and an H-CDR3 as set forth in SEQ ID NO:31.

In some further aspects, the disclosure provides an isolated antibody, or antigen-binding portion thereof, that specifically binds human 4-1BB, wherein said antibody or antigen-binding portion is selected from the group consisting of:

(a) an antibody or antigen-binding portion thereof, comprising an L-CDR1 as set forth in SEQ ID NO:6, an L-CDR2 as set forth in SEQ ID NO:7, and an L-CDR3 as set forth in SEQ ID NO:8.

(b) an antibody or antigen-binding portion thereof, comprising an L-CDR1 as set forth in SEQ ID NO:20, an L-CDR2 as set forth in SEQ ID NO:21, and an L-CDR3 as set forth in SEQ ID NO:22.

(c) an antibody or antigen-binding portion thereof, comprising an L-CDR1 as set forth in SEQ ID NO:34, an L-CDR2 as set forth in SEQ ID NO:35, and an L-CDR3 as set forth in SEQ ID NO:36; and (d) an antibody or antigen-binding portion thereof, comprising an L-CDR1 as set forth in SEQ ID NO:34, an L-CDR2 as set forth in SEQ ID NO:35, and an L-CDR3 as set forth in SEQ ID NO:55.

In some further particular aspects, the isolated antibody is selected from the group consisting of:

(a) an antibody or antigen-binding portion thereof, comprising: an H-CDR1 as set forth in SEQ ID NO:1, an H-CDR2 as set forth in SEQ ID NO:2, an H-CDR3 as set forth in SEQ ID NO:3; an L-CDR1 as set forth in SEQ ID NO:6, an L-CDR2 as set forth in SEQ ID NO:7, and an L-CDR3 as set forth in SEQ ID NO:8;

(b) an antibody or antigen-binding portion thereof, comprising an H-CDR1 as set forth in SEQ ID NO:15, an H-CDR2 as set forth in SEQ ID NO:16, an H-CDR3 as set forth in SEQ ID NO:17; an L-CDR1 as set forth in SEQ ID NO:20, an L-CDR2 as set forth in SEQ ID NO:21, and an L-CDR3 as set forth in SEQ ID NO:22.

(c) an antibody or antigen-binding portion thereof, comprising an H-CDR1 as set forth in SEQ ID NO:29, an H-CDR2 as set forth in SEQ ID NO:30, an H-CDR3 as set forth in SEQ ID NO:31; an L-CDR1 as set forth in SEQ ID NO:34, an L-CDR2 as set forth in SEQ ID NO:35, and an L-CDR3 as set forth in SEQ ID NO:36; and (d) an antibody or antigen-binding portion thereof, comprising an H-CDR1 as set forth in SEQ ID NO:29, an H-CDR2 as set forth in SEQ ID NO:30, an H-CDR3 as set forth in SEQ ID NO:31; an L-CDR1 as set forth in SEQ ID NO:34, an L-CDR2 as set forth in SEQ ID NO:35, and an L-CDR3 as set forth in SEQ ID NO:55.

In a further particular aspect, the isolated antibody comprises a $V_H$ chain amino acid sequence as set forth in SEQ ID NO:4, SEQ ID NO:18, SEQ ID NO:32, and SEQ ID NO:43.

In a further particular aspect, the isolated antibody comprises a $V_L$ chain amino acid sequence as set forth in SEQ ID NO:9, SEQ ID NO:23, SEQ ID NO:37, SEQ ID NO:45, SEQ ID NO:51, SEQ ID NO:56, SEQ ID NO:60, or SEQ ID NO:64.

In a further particular aspect, the isolated antibody comprises a $V_H$ domain amino acid sequence as set forth in any one of SEQ ID NOs:4, 18, 32, and :43, and further comprises a $V_L$ domain amino acid sequence as set forth in any one of SEQ ID NOs:9, SEQ ID NO: 23, SEQ ID NO: 37, SEQ ID NO: 45, SEQ ID NO: 51, SEQ ID NO: 56, SEQ ID NO: 60, and SEQ ID NO: 64.

In a further particular aspect, the isolated antibody is selected from the group consisting of:

(a) an antibody comprising a $V_H$ chain amino acid sequence as set forth in SEQ ID NO:4 and a $V_L$ chain amino acid sequence as set forth in SEQ ID NO:9;

(b) an antibody comprising a $V_H$ chain amino acid sequence as set forth in SEQ ID NO:18 and a $V_L$ chain amino acid sequence as set forth in SEQ ID NO:23;

(c) an antibody comprising a $V_H$ chain amino acid sequence as set forth in SEQ ID NO:32 and a $V_L$ chain amino acid sequence as set forth in SEQ ID NO:37 or SEQ ID NO 56; and (d) an antibody comprising a $V_H$ chain amino acid sequence as set forth in SEQ ID NO:43 and a $V_L$ chain amino acid sequence as set forth in SEQ ID NO:45, SEQ ID NO:51, SEQ ID NO: 60, or SEQ ID NO: 64.

In a still further particular aspect, the isolated antibody provided by the present disclosure comprises a $V_H$ chain that is encoded by (i) a nucleic acid sequence comprising SEQ ID NO:11, SEQ ID NO:25, SEQ ID NO:39, SEQ ID NO:47, or (ii) a nucleic acid sequences that hybridizes under high stringency conditions to the complementary strand of SEQ ID NO:11, SEQ ID NO:25, SEQ ID NO:39, or SEQ ID NO:47.

In a still further particular aspect, the isolated antibody comprises a $V_L$ chain that is encoded by (i) a nucleic acid sequence comprising SEQ ID NO:12, SEQ ID NO:26, SEQ ID NO:40, SEQ ID NO:48, SEQ ID NO:53, SEQ ID NO:58, SEQ ID NO:62, or SEQ ID NO:66, or (ii) a nucleic acid sequences that hybridizes under high stringency conditions to the complementary strand of SEQ ID NO:12, SEQ ID NO:26, SEQ ID NO:40, SEQ ID NO:48, SEQ ID NO:53, SEQ ID NO:58, SEQ ID NO:62, or SEQ ID NO:66.

In a further particular aspect, there is provided an isolated antibody that competes, and/or cross-competes for binding to human 4-1BB with an illustrative antibody selected from MOR-6032, MOR-7361, MOR-7480, MOR-7480.1, MOR-7480.2, MOR 7483, MOR-7483.1, or MOR-7483.2.

In a further particular aspect, there is provided an isolated antibody that binds to the same epitope on human 4-1BB as any of the antibodies disclosed herein. In some embodiments, the disclosure provides an isolated antibody that binds to the same epitope on human 4-1BB as an illustrative antibody selected from MOR-6032, MOR-7361, MOR-7480, MOR-7480.1, MOR-7480.2, MOR 7483, MOR-7483.1, or MOR-7483.2.

In a further particular aspect, the present disclosure provides an isolated antibody that binds human 4-1BB, comprising a heavy chain variable region that is the product of, or derived from, a human $V_H$ 3-23 gene, $V_H$ 1-69 gene, or $V_H$ 5. In another particular aspect the present disclosure provides an isolated antibody that binds human 4-1BB, comprising a light chain variable region that is the product of, or derived from, a human $V_L$ λ3 or λ1-13 gene.

In some embodiments, the isolated antibodies described herein have one or more of the following properties or characteristics:

a) specifically bind to human 4-1BB;
b) bind to human and cynomolgus 4-1BB;
c) bind to human 4-1BB or cynomolgus 4-1BB but not rat, or mouse 4-1BB;
d) are an IgG, such as IgG1, IgG2, IgG3, or IgG4; and
e) are human antibodies, or humanized antibodies.

In some other aspects, the present disclosure provides an antigen-binding portion of any of the antibody provided by the present disclosure. In some embodiments, the antigen-binding portion is Fab or scFv fragment.

In some further aspects, the present disclosure provides a derivative of any of the antibodies provided by the present disclosure.

In some other aspects, the disclosure provides an isolated nucleic acid that encodes a $V_H$ chain of an antibody or antigen-binding portion thereof that bind human 4-1BB, which is selected from the group consisting of:

(i) a nucleic acid sequence that encodes a $V_H$ chain amino acid sequence as set forth in SEQ ID NO:4, SEQ ID NO:18, SEQ ID NO:32, or SEQ ID NO:43;

(ii) a nucleic acid sequence as set forth in SEQ ID NO:11, SEQ ID NO:25, SEQ ID NO:39, or SEQ ID NO:47; or (iii) a nucleic acid sequence that hybridizes under high stringency conditions to the complementary strand of a nucleic acid sequence as set forth in SEQ ID NO:11, SEQ ID NO:25, SEQ ID NO:39, or SEQ ID NO:47.

In some other aspects, the disclosure provides an isolated nucleic acid that encodes a $V_L$ chain of an antibody or antigen-binding portion thereof that binds human 4-1BB, which is selected from the group consisting of:

(i) a nucleic acid sequence that encodes a $V_L$ chain amino acid sequence as set forth in SEQ ID NO:9, SEQ ID NO:23, SEQ ID NO:37, SEQ ID NO:45, SEQ ID NO:51, SEQ ID NO:56, SEQ ID NO:60, or SEQ ID NO:64;

(ii) a nucleic acid sequence as set forth in SEQ ID NO:12, SEQ ID NO:26, SEQ ID NO:40, SEQ ID NO:48, SEQ ID NO:53, SEQ ID NO:58, SEQ ID NO: 62, or SEQ ID NO:66; or (ii) a nucleic acid sequences that hybridizes under high stringency conditions to the complementary strand of a nucleic acid sequence as set forth in SEQ ID NO:12, SEQ ID NO:26, SEQ ID NO:40, SEQ ID NO:48, SEQ ID NO:53, SEQ ID NO:58, SEQ ID NO: 62, or SEQ ID NO:66.

In some further aspects, the disclosure provides a vector comprising any of the nucleic acids described herein. In a still further aspect, the disclosure provides a host cell comprising any of the vectors described herein. Such host cells can be bacterial or mammalian.

In some further aspects, the disclosure provides a pharmaceutical composition comprising any of the antibodies, an antigen-binding portions thereof, or a derivative thereof, and a pharmaceutically acceptable carrier.

The disclosure further provides methods for treating abnormal cell growth in a subject in need thereof, comprising administering to the subject an effective amount of a binding molecule of the disclosure or pharmaceutical composition described herein. The disclosure further provides methods of reducing tumor cell metastasis in a subject, comprising administering to said subject an effective amount of a binding molecule, or pharmaceutical compositions described herein.

In a further aspect, the disclosure provides a use of any of the binding molecules, or a pharmaceutical composition described herein, for the manufacture of a medicament for the treatment of abnormal cell growth in a subject in need thereof. In a further aspect, the disclosure provides a binding molecule, or a pharmaceutical composition, as described herein, for use in the treatment of abnormal cell growth in a subject in need thereof. In a yet further aspect, the disclosure provides a binding molecule, or a pharmaceutical composition, as described herein, for use in the treatment of tumor cell metastasis in a subject in need thereof. In a still further aspect, the disclosure provides a use of any of the binding molecules, or a pharmaceutical composition described herein, for the manufacture of a medicament for the treatment of tumor cell metastasis in a subject in need thereof.

BRIEF DESCRIPTION OF THE DRAWINGS

FIG. 8 shows alignments of Amino Acid Sequences of the heavy Chain Variable Regions and Light Chain Variable Regions (with CDRs underlined) with Relevant Germline Sequences.

Figure 1:
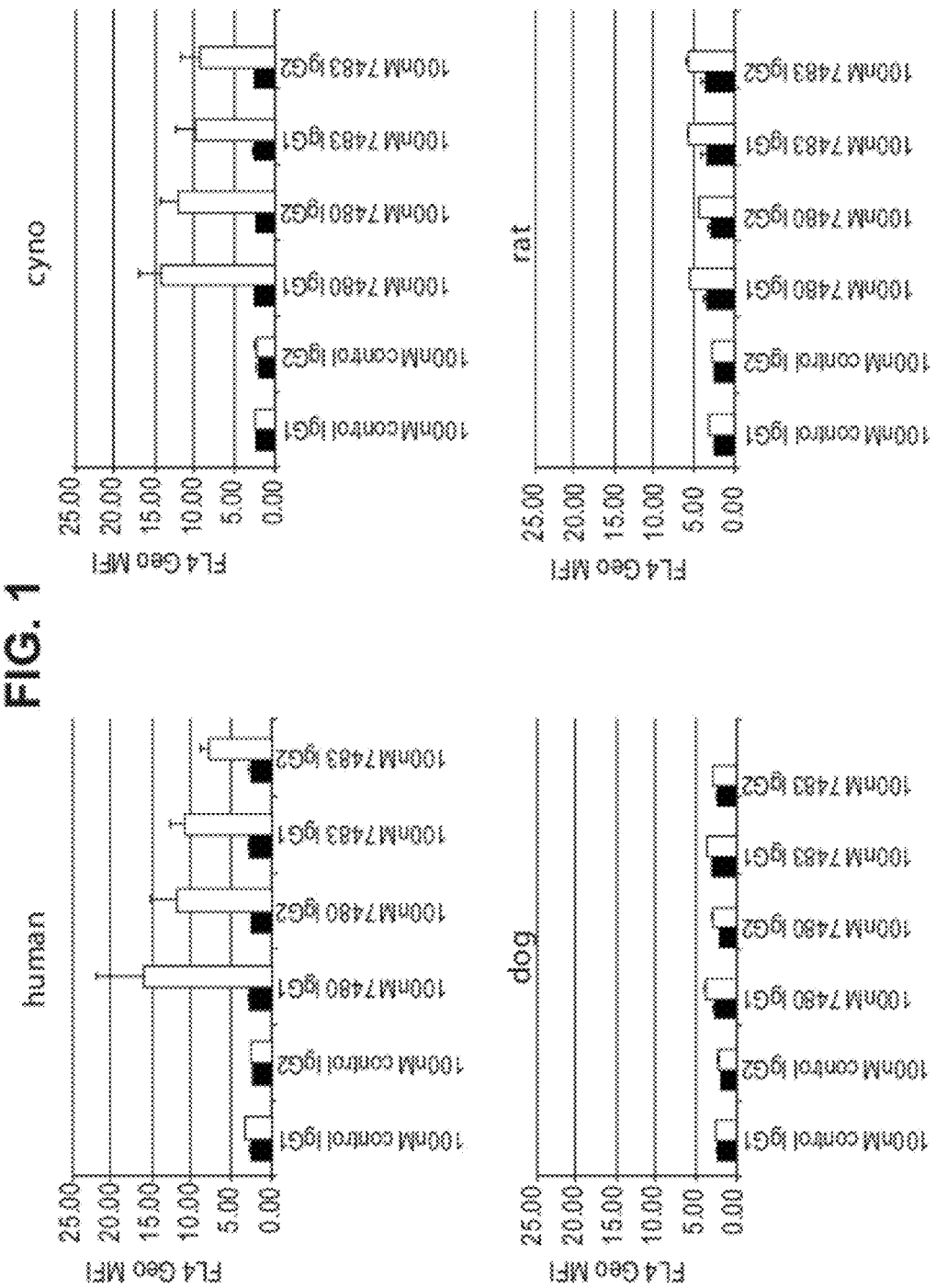
FIG. 1 is four column graphs showing the mean fluorescence intensity of unstimulated (black) and PHA stimulated (light grey) primary PBMC from human (upper left), cynomolgus (upper right), dog (lower left), and rat (lower right) incubated with the indicated 4-1BB antibody or control antibody conjugated to Alexafluor 647. The panel demonstrates binding to human and cynomolgus PBMC stimulated with PHA.

The heavy chain variable region amino acid sequences are identified as follows: GERMLINE VH1-69 (GenBank Accession No. AAC18244.1); MOR6032 VH (SEQ ID NO: 4); GERMLINE VH3-23 (GenBank Accession No. AAC51014.1); MOR7361 VH (SEQ ID NO: 18); GERMLINE VH5 (GenBank Accession No. AAB36776.1); MOR7480 VH (SEQ ID NO: 32); MOR7480.1 VH (SEQ ID NO: 43); MOR7480.2 VH (SEQ ID NO: 43); MOR7483 VH (SEQ ID NO: 32); MOR7483.1 VH (SEQ ID NO: 43); and, MOR7483.2 VH (SEQ ID NO: 43).

The light chain variable region amino acid sequences are identified as follows: GERMLINE VL3-r (GenBank Accession No. AAF20506.1); MOR6032 VL (SEQ ID NO: 9); MOR7361 VL (SEQ ID NO: 23); MOR7480 VL (SEQ ID NO: 37); MOR7480.1 VL (SEQ ID NO: 45); MOR7480.2 VL (SEQ ID NO: 51); MOR7483 VL (SEQ ID NO: 56); MOR7483.1 VL (SEQ ID NO: 60); and, MOR7483.2 (SEQ ID NO: 64).

DETAILED DESCRIPTION

A. Definitions

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

As used herein, each of the following terms has the meaning associated with it in this section.

The term "4-1BB antibody" refers to an antibody, as defined herein, capable of binding to human 4-1BB receptor.

The terms "4-1BB" and "4-1BB receptor" are used interchangeably in the present application, and include the human 4-1BB receptor, as well as variants, isoforms, and species homologs thereof. Accordingly, a binding molecule, as defined and disclosed herein, may also bind 4-1BB from species other than human. In other cases, a binding molecule may be completely specific for the human 4-1BB and may not exhibit species or other types of cross-reactivity.

The articles "a" and "an" refer to one or to more than one (i.e., to at least one) of the grammatical object of the article. By way of example, "an element" means one element or more than one element.

The term "agonist" refers to a binding molecule, as defined herein, which upon binding to 4-1BB, (1) stimulates or activates 4-1BB, (2) enhances, increases, promotes, induces, or prolongs an activity, function, or presence of 4-1BB, or (3) enhances, increases, promotes, or induces the expression of 4-1BB.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. The term "amino acid analogs" refers to compounds that have the same basic chemical structure as a naturally occurring amino acid but the C-terminal carboxy group, the N-terminal amino group, or side chain functional group has been chemically modified to another functional group. The term "amino acid mimetics" refers to chemical compounds that have a structure that is different from the general chemical structure of an amino acid, but that functions similarly to a naturally occurring amino acid.

The term "antibody" is an art-recognized term and refers to an antigen-binding protein (i.e, immunoglobulin) having a basic four-polypeptide chain structure consisting of two identical heavy (H) chains and two identical light (L) chains. Each L chain is linked to an H chain by one covalent disulfide bond, while the two H chains are linked to each other by one or more disulfide bonds depending on the H chain isotype. Each heavy chain has, at the N-terminus, a variable region (abbreviated herein as $V_H$) followed by a constant region. The heavy chain constant region is comprised of three domains, $C_{H1}$, $C_{H2}$ and $C_{H3}$. Each light chain has, at the N-terminus, a variable region (abbreviated herein as $V_L$) followed by a constant region at its other end. The light chain constant region is comprised of one domain, $C_L$. The $V_L$ is aligned with the $V_H$ and the $C_L$ is aligned with the first constant domain of the heavy chain (CH1). The pairing of a $V_H$ and $V_L$ together forms a single antigen-binding site. An IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain.

The $V_H$ and $V_L$ regions can be further subdivided into regions of hypervariability, termed complementarity determining regions (CDR), interspersed with regions that are more conserved, termed framework regions (FR). The CDR regions can be determined using the Kabat or Chothia numbering systems, both of which are well known to those of skill in the art. See, e.g. Kabat, E. A., et al. (1991) Sequences of Proteins of Immunological Interest, Fifth Edition, U.S. Department of Health and Human Services, NIH Publication No. 91-3242; Chothia and Lesk, J. Mol. Biol. 196:901-917 (1987). Each $V_H$ and $V_L$ is composed of three CDRs and four FRs, arranged from amino-terminus to carboxy-terminus in the following order: FR1, CDR1, FR2, CDR2, FR3, CDR3, FR4. Throughout the present disclosure, the three CDRs of the heavy chain are referred to as H-CDR1, H-CDR2, and H-CDR3. Similarly, the three CDRs of the light chain are referred to as L-CDR1, L-CDR2, and L-CDR3. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Within light and heavy chains, the variable and constant regions are joined by a "J" region of about 12 or more amino acids, with the heavy chain also including a "D" region of about 10 or more amino acids. See generally, Fundamental Immunology Ch. 7 (Paul, W., ed., $2^{nd}$ ed. Raven Press, N.Y. (1989)).

The L chain from any vertebrate species can be assigned to one of two clearly distinct types, called kappa and lambda, based on the amino acid sequences of their constant domains. Depending on the amino acid sequence of the constant domain of their heavy chains (CH), antibodies can be assigned to different classes or isotypes. There are five classes of antibodies: IgA, IgD, IgE, IgG, and IgM, having heavy chains designated α (alpha), δ (delta), ε (epsilon), γ (gamma), and μ (mu), respectively. The IgG class of antibody can be further classified into four subclasses IgG1, IgG2, IgG3, and IgG4 by the gamma heavy chains, Y1-Y4, respectively.

The term "antibody derivative" or "derivative" of an antibody refers to a molecule that is capable of binding to the same antigen (e.g., 4-1BB) that the antibody binds to and comprises an amino acid sequence of the antibody linked to an additional molecular entity. The amino acid sequence of the antibody that is contained in the antibody derivative may be a full-length heavy chain, a full-length light chain, any portion or portions of a full-length heavy chain, any portion or portions of the full-length light chain of the antibody, any other fragment(s) of an antibody, or the complete antibody. The additional molecular entity may be a chemical or biological molecule. Examples of additional molecular entities include chemical groups, amino acids, peptides, proteins (such as enzymes, antibodies), and chemical compounds. The additional molecular entity may have any utility, such as for use as a detection agent, label, marker, pharmaceutical or therapeutic agent. The amino acid sequence of an antibody may be attached or linked to the additional molecular entity by chemical coupling, genetic fusion, noncovalent association, or otherwise. The term "antibody derivative" also encompasses chimeric antibodies, humanized antibodies, and molecules that are derived from modifications of the amino acid sequences of a 4-1BB antibody, such as conservation amino acid substitutions, additions, and insertions.

The term "antigen-binding fragment" or "antigen binding portion" of an antibody refers to one or more portions of an antibody that retain the ability to bind to the antigen that the antibody bonds to (e.g., 4-1BB). Examples of "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., Nature 341:544-546 (1989)), which consists of a $V_H$ domain; and (vi) an isolated complementarity determining region (CDR).

The term "binding molecule" encompasses (1) antibody, (2) antigen-binding fragment of an antibody, and (3) derivative of an antibody, each as defined herein.

The term "binding 4-1BB," "binds 4-1BB," "binding to 4-1BB," or "binds to 4-1BB" refers to the binding of a binding molecule, as defined herein, to the human 4-1BB in an in vitro assay, such as a BIAcore assay as described in Example 6, with an affinity ($K_D$) of 500 nM or less.

The term "chimeric antibody" refers to an antibody that comprises amino acid sequences derived from different animal species, such as those having a variable region derived from a human antibody and a murine immunoglobulin constant region.

The term "compete for binding" refers to the interaction of two antibodies in their binding to a binding target. A first antibody competes for binding with a second antibody if binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not, be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "cross-compete" with each other for binding of their respective epitope(s).

The term "epitope" refers to a part of an antigen to which an antibody (or antigen-binding fragment thereof) binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope can include various numbers of amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, G. E. Morris, Ed. (1996). Once a desired epitope on an antigen is determined, antibodies to that epitope can be generated, e.g., using the techniques described herein. The generation and characterization of antibodies may also elucidate information about desirable epitopes. From this information, it is then possible to competitively screen antibodies for binding to the same epitope. An approach to achieve this is to conduct cross-competition studies to find antibodies that competitively bind with one another, i.e., the antibodies compete for binding to the antigen. A high throughput process for "binning" antibodies based upon their cross-competition is described in PCT Publication No. WO 03/48731.

The term "germline" refers to the nucleotide sequences of the antibody genes and gene segments as they are passed from parents to offspring via the germ cells. The germline sequence is distinguished from the nucleotide sequences encoding antibodies in mature B cells which have been altered by recombination and hypermutation events during the course of B cell maturation.

The term "glycosylation sites" refers to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. The specific site of attachment is typically signaled by a sequence of amino acids, referred to herein as a "glycosylation site sequence". The glycosylation site sequence for N-linked glycosylation is: -Asn-X-Ser- or -Asn-X-Thr-, where X may be any of the conventional amino acids, other than proline. The terms "N-linked" and "O-linked" refer to the chemical group that serves as the attachment site between the sugar molecule and the amino acid residue. N-linked sugars are attached through an amino group; O-linked sugars are attached through a hydroxyl group. The term "glycan occupancy" refers to the existence of a carbohydrate moiety linked to a glycosylation site (i.e., the glycan site is occupied). Where there are at least two potential glycosylation sites on a polypeptide, either none (0-glycan site occupancy), one (1-glycan site occupancy) or both (2-glycan site occupancy) sites can be occupied by a carbohydrate moiety.

The term "host cell" refers to a cellular system which can be engineered to generate proteins, protein fragments, or peptides of interest. Host cells include, without limitation, cultured cells, e.g., mammalian cultured cells derived from rodents (rats, mice, guinea pigs, or hamsters) such as CHO, BHK, NSO, SP2/0, YB2/0; or human tissues or hybridoma cells, yeast cells, and insect cells, and cells comprised within a transgenic animal or cultured tissue. The term encompasses not only the particular subject cell but also the progeny of such a cell. Because certain modifications may occur in succeeding generations due to either mutation or environmental influences, such progeny may not be identical to the parent cell, but are still included within the scope of the term "host cell."

The term "human antibody" refers to an antibody in which the entire amino acid sequences of the light chains and heavy chains are from the human immunoglobulin genes. A human antibody may contain murine carbohydrate chains if produced in a mouse, in a mouse cell or in a hybridoma derived from a mouse cell. Human antibodies may be prepared in a variety of ways known in the art.

The term "humanized antibody" refers to a chimeric antibody that contains amino acid residues derived from human antibody sequences. A humanized antibody may contain some or all of the CDRs from a non-human animal antibody while the framework and constant regions of the antibody contain amino acid residues derived from human antibody sequences.

The term "illustrative antibody" refers to any one of the antibodies described in the disclosure and designated as MOR-6032, MOR-7361, MOR-7480, MOR-7480.1, MOR-7480.2, MOR-7483, MOR-7483.1, and MOR-7483.2. These antibodies may be in any class (e.g., IgA, IgD, IgE, IgG, and IgM). Thus, each antibody identified above encompasses antibodies in all five classes that have the same amino acid sequences for the $V_L$ and $V_H$ regions. Further, the antibodies in the IgG class may be in any subclass (e.g., IgG1 IgG2, IgG3, and IgG4). Thus, each antibody identified above in the IgG subclass encompasses antibodies in all four subclasses that have the same amino acid sequences for the $V_L$ and $V_H$ regions. The amino acid sequences of the heavy chain constant regions of human antibodies in the five classes, as well as in the four IgG subclasses, are known in the art. As examples, the amino acid sequences of the human IgG1 and IgG2 constant regions are provided in SEQ ID NOs: 69 and 71, respectively. The amino acid sequence of the full length heavy chain for the IgG2 subclass of each of the illustrative antibodies is provided in the disclosure.

The term "isolated antibody" or "isolated binding molecule" refers to an antibody or a binding molecule, as defined herein, that: (1) is not associated with naturally associated components that accompany it in its native state; (2) is free of other proteins from the same species; (3) is expressed by a cell from a different species; or (4) does not occur in nature. Examples of isolated antibodies include a 4-1BB antibody that has been affinity purified using 4-1BB, a 4-1BB antibody that has been generated by hybridomas or other cell line in vitro, and a 4-1BB antibody derived from a transgenic animal.

The term "isolated nucleic acid" refers to a nucleic acid molecule of genomic, cDNA, or synthetic origin, or a combination thereof, which is separated from other nucleic acid molecules present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid of interest.

The term "$k_a$" refers to the association rate constant of a particular antibody-antigen interaction, whereas the term "$k_d$" refers to the dissociation rate constant of a particular antibody-antigen interaction.

The term "$K_D$" refers to the equilibrium dissociation constant of a particular antibody-antigen interaction. It is obtained from the ratio of $k_d$ to $k_a$ (i.e., $k_d/k_a$) and is expressed as a molar concentration (M). $K_D$ is used as a measure for the affinity of an antibody's binding to its binding partner. The smaller the $K_D$, the more tightly bound the antibody is, or the higher the affinity between antibody and the antigen. For example, an antibody with a nanomolar (nM) dissociation constant binds more tightly to a particular antigen than an antibody with a micromolar (μM) dissociation constant. $K_D$ values for antibodies can be determined using methods well established in the art. One method for determining the $K_D$ of an antibody is by using surface plasmon resonance, typically using a biosensor system such as a Biacore® system. An assay procedure using the BIACORE™ system (BIAcore assay) is described in the Examples section of this disclosure.

The term "mammal" refers to any animal species of the Mammalia class. Examples of mammals include: humans; laboratory animals such as rats, mice, simians and guinea pigs; domestic animals such as cats, dogs, rabbits, cattle, sheep, goats, horses, and pigs; and captive wild animals such as lions, tigers, elephants, and the like.

The term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies may be prepared by the hybridoma methodology or may be made using recombinant DNA methods in bacterial, eukaryotic animal or plant cells (see, e.g., U.S. Pat. No. 4,816,567). Monoclonal antibodies may also be isolated from phage antibody libraries using the techniques described in Clackson et al., Nature, 352:624-628 (1991) and Marks et al., J. Mol. Biol., 222:581-597 (1991), for example.

The term "prevent" or "preventing," with reference to a certain disease condition in a mammal, refers to preventing or delaying the onset of the disease, or preventing the manifestation of clinical or subclinical symptoms thereof.

The term "recombinant antibody" refers to an antibody that is prepared, expressed, created or isolated by recombinant means, such as antibodies isolated from an animal that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

As used herein, "sequence identity" between two polypeptide sequences indicates the percentage of amino acids that are identical between the sequences. The amino acid sequence identity of polypeptides can be determined conventionally using known computer programs such as Bestfit, FASTA, or BLAST (see, e.g. Pearson, *Methods Enzymol.* 183:63-98 (1990); Pearson, *Methods Mol. Biol.* 132:185-219 (2000); Altschul et al., *J. Mol. Biol.* 215:403-410 (1990); Altschul et al., *Nucelic Acids Res.* 25:3389-3402 (1997)). When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, fragments, or variants thereof disclosed herein.

The term "specifically binds" or "specifically binds to," in reference to the interaction of a binding molecule, as defined herein, (e.g., an antibody) with its binding partner (e.g., an antigen), refers to the ability of the binding molecule to discriminate between an antigen of interest from an animal species and the antigen orthologue from a different animal species under a given set of conditions. A 4-1BB binding molecule is said to specifically bind to human 4-1BB if it binds to human 4-1BB at an EC50 that is below 50 percent of the EC50 at which it binds 4-1BB of rat or mouse as determined in an in vitro assay. Binding specificity of an antibody can be determined using methods known in the art. Examples of such methods include FACS using PHA stimulated primary cells, Western blots, ELISA-, RIA-, ECL-, IRMA-tests and peptide scans.

The term "selectively binds" or "selectively binds to," in reference to the interaction of a binding molecule, as defined herein, (e.g., an antibody) with its binding partner (e.g., an antigen), refers to the ability of the binding molecule to discriminate between an antigen of interest from an animal species (such as human 4-1BB) and a different antigen from the same animal species (such as human CD40) under a given set of conditions. A 4-1BB binding molecule is said to selectively bind to human 4-1BB if it binds to human 4-1BB at an EC50 that is below 10 percent of the EC50 at which it binds to human CD40 or human CD134 as determined in an in vitro assay.

The term "treat", "treating", or "treatment", with reference to a certain disease condition in a mammal, refers causing a desirable or beneficial effect in the mammal having the disease condition. The desirable or beneficial effect may include reduced frequency or severity of one or more symptoms of the disease (i.e., tumor growth and/or metastasis, or other effect mediated by the numbers and/or activity of immune cells, and the like), or arrest or inhibition of further development of the disease, condition, or disorder. In the context of treating cancer in a mammal, the desirable or beneficial effect may include inhibition of further growth or spread of cancer cells, death of cancer cells, inhibition of reoccurrence of cancer, reduction of pain associated with the cancer, or improved survival of the mammal. The effect can be either subjective or objective. For example, if the mammal is human, the human may note improved vigor or vitality or decreased pain as subjective symptoms of improvement or response to therapy. Alternatively, the clinician may notice a decrease in tumor size or tumor burden based on physical exam, laboratory parameters, tumor markers or radiographic findings. Some laboratory signs that the clinician may observe for response to treatment include normalization of tests, such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement, such as sonograms, nuclear magnetic resonance testing and positron emissions testing.

The term "vector" refers to a nucleic acid molecule capable of transporting a foreign nucleic acid molecule. The foreign nucleic acid molecule is linked to the vector nucleic acid molecule by a recombinant technique, such as ligation or recombination. This allows the foreign nucleic acid molecule to be multiplied, selected, further manipulated or expressed in a host cell or organism. A vector can be a plasmid, phage, transposon, cosmid, chromosome, virus, or virion. One type of vectors can be integrated into the genome of a host cell upon introduction into the host cell, and thereby are replicated along with the host genome (e.g., non-episomal mammalian vectors). Another type of vectors are capable of autonomous replication in a host cell into which it is introduced (e.g., bacterial vectors having a bacterial origin of replication and episomal mammalian vectors). Another specific type of vectors capable of directing the expression of expressible foreign nucleic acids to which they are operatively linked are commonly referred to "expression vectors." Expression vectors generally have control sequences that drive expression of the expressible foreign nucleic acids. Simpler vectors, known as "transcription vectors," are only capable of being transcribed but not translated: they can be replicated in a target cell but not expressed. The term "vector" encompasses all types of vectors regardless of their function. Vectors capable of directing the expression of expressible nucleic acids to which they are operatively linked are commonly referred to "expression vectors."

The methods and techniques of the present disclosure are generally performed according to methods well known in the art and as described in various general and more specific references that are cited and discussed throughout the present specification unless otherwise indicated. Such references include, e.g., Sambrook and Russell, *Molecular Cloning, A Laboratory Approach*, Cold Spring Harbor Press, Cold Spring Harbor, N.Y. (2001), Ausubel et al., *Current Protocols in Molecular Biology*, John Wiley & Sons, NY (2002), and Harlow and Lane *Antibodies: A Laboratory Manual*, Cold Spring Harbor Laboratory Press, Cold Spring Harbor, N.Y. (1990). Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)).

B. Binding Molecules that Bind to Human 4-1BB

The present disclosure provides isolated binding molecules that bind to human 4-1BB, including 4-1BB antibodies, antigen-binding fragments of the 4-1BB antibodies, and derivatives of the 4-1BB antibodies.

B-1. 4-1BB Antibodies

In some aspects, the present disclosure provides an isolated antibody that binds to human 4-1BB at an epitope within amino acid residues 115-156 of SEQ ID No: 68. In some embodiments, the isolated antibody comprises the H-CDR1 amino acid sequence of SEQ ID NO: 29, H-CDR2 amino acid sequence of SEQ ID NO: 30, and H-CDR3 amino acid sequence of SEQ ID NO: 31. In some other embodiments, the isolated antibody comprises the L-CDR1 amino acid sequence of SEQ ID NO: 34, L-CDR2 amino acid sequence of SEQ ID NO: 35, and L-CDR3 amino acid sequence of SEQ ID NO: 36. In some other embodiments, the antibodies described herein above have one or more biological properties described herein below.

In other aspects, the disclosure provides an isolated antibody that binds to human 4-1BB, wherein said antibody comprises: (a) an H-CDR1 as set forth in SEQ ID NO:1, SEQ ID NO:15, or SEQ ID NO:29; (b) an H-CDR2 as set forth in SEQ ID NO:2, SEQ ID NO:16, or SEQ ID NO:30; and (c) an H-CDR3 as set forth in SEQ ID NO:3, SEQ ID NO: 17, or SEQ ID NO:31.

In another aspect, the disclosure provides an isolated antibody that binds to human 4-1BB, wherein said antibody comprises: (a) an L-CDR1 as set forth in SEQ ID NO:6, SEQ ID NO: 20, or SEQ ID NO:34; (b) an L-CDR2 as set forth in SEQ ID NO:7, SEQ ID NO:21, or SEQ ID NO:35; and (c) an L-CDR3 as set forth in SEQ ID NO:8, SEQ ID NO:22, SEQ ID NO:36, or SEQ ID NO: 55.

In a further aspect, the disclosure provides an isolated antibody that binds to human 4-1BB, wherein said antibody comprises: (a) an H-CDR1 as set forth in SEQ ID NO:1, SEQ ID NO:15, or SEQ ID NO:29; (b) an H-CDR2 as set forth in SEQ ID NO:2, SEQ ID NO:16, or SEQ ID NO:30; and (c) an H-CDR3 as set forth in SEQ ID NO:3, SEQ ID NO: 17, or SEQ ID NO:31; and further comprises: (d) an L-CDR1 as set forth in SEQ ID NO:6, SEQ ID NO: 20, or SEQ ID NO:34; (e) an L-CDR2 as set forth in SEQ ID NO:7, SEQ ID NO:21, or SEQ ID NO:35; and (f) an L-CDR3 as set forth in SEQ ID NO:8, SEQ ID NO:22, SEQ ID NO:36, or SEQ ID NO: 55.

In some further aspects, the disclosure provides an isolated antibody that binds to human 4-1BB, wherein said antibody is selected from the group consisting of:
(a) an antibody comprising an H-CDR1 as set forth in SEQ ID NO:1, an H-CDR2 as set forth in SEQ ID NO:2, and an H-CDR3 as set forth in SEQ ID NO:3;
(b) an antibody comprising an H-CDR1 as set forth in SEQ ID NO:15, an H-CDR2 as set forth in SEQ ID NO:16, and an H-CDR3 as set forth in SEQ ID NO:17; and
(c) an antibody comprising an H-CDR1 as set forth in SEQ ID NO:29, an H-CDR2 as set forth in SEQ ID NO:30, and an H-CDR3 as set forth in SEQ ID NO:31.

In some further aspects, the disclosure provides an isolated antibody that binds to human 4-1BB, wherein said antibody is selected from the group consisting of:
(a) an antibody comprising an L-CDR1 as set forth in SEQ ID NO:6, an L-CDR2 as set forth in SEQ ID NO:7, and an L-CDR3 as set forth in SEQ ID NO:8;
(b) an antibody comprising an L-CDR1 as set forth in SEQ ID NO:20, an L-CDR2 as set forth in SEQ ID NO:21, and an L-CDR3 as set forth in SEQ ID NO:22;
(c) an antibody comprising an L-CDR1 as set forth in SEQ ID NO:34, an L-CDR2 as set forth in SEQ ID NO:35, and an L-CDR3 as set forth in SEQ ID NO:36; and
(d) an antibody comprising an L-CDR1 as set forth in SEQ ID NO:34, an L-CDR2 as set forth in SEQ ID NO:35, and an L-CDR3 as set forth in SEQ ID NO:55.

In some further aspects, the disclosure provides an isolated antibody that binds to the human 4-1BB, wherein said antibody is selected from the group consisting of:
(a) an antibody comprising an H-CDR1 as set forth in SEQ ID NO:1, an H-CDR2 as set forth in SEQ ID NO:2, an H-CDR3 as set forth in SEQ ID NO:3; an L-CDR1 as set forth in SEQ ID NO:6, an L-CDR2 as set forth in SEQ ID NO:7, and an L-CDR3 as set forth in SEQ ID NO:8;
(b) an antibody comprising an H-CDR1 as set forth in SEQ ID NO:15, an H-CDR2 as set forth in SEQ ID NO:16, an H-CDR3 as set forth in SEQ ID NO:17; an L-CDR1 as set forth in SEQ ID NO:20, an L-CDR2 as set forth in SEQ ID NO:21, and an L-CDR3 as set forth in SEQ ID NO:22;
(c) an antibody comprising an H-CDR1 as set forth in SEQ ID NO:29, an H-CDR2 as set forth in SEQ ID NO:30, an H-CDR3 as set forth in SEQ ID NO:31; an L-CDR1 as set forth in SEQ ID NO:34, an L-CDR2 as set forth in SEQ ID NO:35, and an L-CDR3 as set forth in SEQ ID NO:36; and
(d) an antibody comprising an H-CDR1 as set forth in SEQ ID NO:29, an H-CDR2 as set forth in SEQ ID NO:30, an H-CDR3 as set forth in SEQ ID NO:31; an L-CDR1 as set forth in SEQ ID NO:34, an L-CDR2 as set forth in SEQ ID NO:35, and an L-CDR3 as set forth in SEQ ID NO:55.

In a further aspect, the disclosure provides an isolated antibody that binds to human 4-1BB, wherein said antibody comprises a $V_H$ chain amino acid sequence as set forth in SEQ ID NO:4, SEQ ID NO:18, SEQ ID NO:32, or SEQ ID NO:43.

In a further aspect, the disclosure provides an isolated antibody that binds to human 4-1BB, wherein said antibody comprises a $V_L$ chain amino acid sequence as set forth in SEQ ID NO:9, SEQ ID NO:23, SEQ ID NO:37, SEQ ID NO:45, SEQ ID NO:51, SEQ ID NO:56, SEQ ID NO:60, or SEQ ID NO:64.

In a further aspect, the disclosure provides an isolated antibody that binds to human 4-1BB, wherein said antibody comprises (1) a $V_H$ chain amino acid sequence as set forth in SEQ ID NO:4, SEQ ID NO:18, SEQ ID NO:32, or SEQ ID NO:43, and (2) a $V_L$ chain amino acid sequence as set forth in SEQ ID NO:9, SEQ ID NO:23, SEQ ID NO:37, SEQ ID NO:45, SEQ ID NO:51, SEQ ID NO:56, SEQ ID NO:60, or SEQ ID NO:64.

In a further aspect, the disclosure provides an isolated antibody that binds to human 4-1BB, wherein said antibody is selected from the group consisting of:
(a) an antibody comprising a $V_H$ chain amino acid sequence as set forth in SEQ ID NO:4 and a $V_L$ chain amino acid sequence as set forth in SEQ ID NO:9;
(b) an antibody comprising a $V_H$ chain amino acid sequence as set forth in SEQ ID NO:18 and a $V_L$ chain amino acid sequence as set forth in SEQ ID NO:23;
(c) an antibody comprising a $V_H$ chain amino acid sequence as set forth in SEQ ID NO:32 and a $V_L$ chain amino acid sequence as set forth in SEQ ID NO:37 or SEQ ID NO 56; and
(d) an antibody comprising a $V_H$ chain amino acid sequence as set forth in SEQ ID NO:43 and a $V_L$ chain amino acid sequence as set forth in SEQ ID NO:45, SEQ ID NO:51, SEQ ID NO: 60, or SEQ ID NO: 64.

In some embodiments, the antibodies described herein above, including antibodies described with reference to epitope binding and antibodies described with reference to specific amino acid sequences of CDRs or variable regions, have at least one of the following functional properties: (a) bind to human 4-1BB with a $K_D$ of 500 nM or less; (b) have agonist activity on human 4-1BB; (c) do not bind to human CD40 receptor at concentration up to 1000 nM; (d) do not bind to human CD134 receptor at concentrations up to 1000 nM; (e) do not bind to rat, or mouse 4-1BB at concentrations up to 100 nM; (h) are capable of inhibiting tumor cell growth; and (i) have therapeutic effect on a cancer. In some further embodiments, the antibodies specifically bind to human 4-1BB with a $K_D$ of 500 nM or less, 100 nM or less, 50 nM or less, 10 nM or less, 5 nM or less, or 1 nM or less, for the human 4-1BB extracellular domain as measured with the BIACore assay described in this disclosure. In still further embodiments, the antibody is a human antibody or humanized antibody that specifically binds to human 4-1BB with a $K_D$ of 500 nM or less, 100 nM or less, 50 nM or less, 10 nM or less, 5 nM or less, or 1 nM or less, for the human 4-1BB extracellular domain as measured with the BIACore assay described in this disclosure. In some further embodiments, the antibody is a human antibody that specifically and selectively binds to human 4-1BB.

In other embodiments, the antibodies described herein above comprise a heavy chain variable region from a particular germline heavy chain immunoglobulin gene and/or a light chain variable region from a particular germline light chain immunoglobulin gene, such as an antibody comprising a heavy chain variable region that is the product of, or derived from, a human $V_H$ 1-69 gene, $V_H$ 3-23 gene, or $V_H$ 5 gene. Exemplary antibodies include MOR-7480.1, MOR-7480.2, MOR-7483.1, and MOR-7483.2, each of which contains amino acids that derived from human germline $V_H$5 gene.

In still other embodiments, the antibodies described herein above comprise a light chain variable region that is derived from a human $V_L$ λ3 gene. In yet other embodiment the antibodies described herein above comprise a heavy chain variable region that is the product of, or derived from, a human $V_H$ 1-69 gene, $V_H$ 3-23 gene, or $V_H$ 5 gene, and further comprise a light chain variable region that is the product of, or derived from, a human $V_L$ λ3 gene, wherein the antibody or portion thereof specifically binds to human 4-1BB. Exemplary antibodies include MOR-7480.1, MOR-7480.2, MOR-7483.1, and MOR-7483.2, each of which contains amino acids that derived from human germline $V_H$5 gene and $V_L$ λ3 gene, respectively.

As used herein, a human antibody comprises heavy or light chain variable regions that is "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acid sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. In certain cases, the human antibody is identical in amino acid sequence to the amino acid sequence encoded by the germline Ig gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid differences from the amino acid sequence encoded by the germline immunoglobulin gene. Alignments of the amino acid sequences of variable regions of the illustrative antibodies and the relevant germlines are provided in FIG. 6.

In another aspect, the disclosure provides isolated antibodies that compete or cross-compete for binding to human 4-1BB with any of the illustrative antibodies of the disclosure, such as MOR-6032, MOR-7361, MOR-7480, MOR-7480.1, MOR-7480.2, MOR-7483, MOR-7483.1, or MOR-7483.2. In a particular embodiment, the disclosure provides isolated antibodies that compete or cross-compete for binding to the same epitope on the human 4-1BB with any of the illustrative antibodies of the disclosure. The ability of an antibody to compete cross-compete for binding with another antibody can be determined using standard binding assays known in the art, such as BIAcore analysis, ELISA assays, or flow cytometry. For example, one can allow an illustrative antibody of the disclosure to bind to human 4-1BB under saturating conditions and then measure the ability of the test antibody to bind to the 4-1BB. If the test antibody is able to bind to the 4-1BB at the same time as the illustrative antibody, then the test antibody binds to a different epitope as the illustrative antibody. However, if the test antibody is not able to bind to the 4-1BB at the same time, then the test antibody binds to the same epitope, an overlapping epitope, or an epitope that is in close proximity to the epitope bound by the illustrative antibody. This experiment can be performed using various methods, such as ELISA, RIA, FACS or surface plasmon resonance.

The 4-1BB antibodies described herein can be in any class, such as IgG, IgM, IgE, IgA, or IgD. It is preferred that the 4-1BB antibodies are in the IgG class, such as IgG1, IgG2, IgG3, or IgG4 subclass, more preferably IgG2 subclass. A 4-1BB antibody can be converted from one class or subclass to another class or subclass using methods known in the art. An exemplary method for producing an antibody in a desired class or subclass comprises the steps of isolating a nucleic acid encoding a heavy chain of an 4-1BB antibody and a nucleic acid encoding a light chain of a 4-1BB antibody, isolating the sequence encoding the $V_H$ region, ligating the $V_H$ sequence to a sequence encoding a heavy chain constant region of the desired class or subclass, expressing the light chain gene and the heavy chain construct in a cell, and collecting the 4-1BB antibody.

Further, the antibodies provided by the present disclosure can be monoclonal or polyclonal, but preferably monoclonal.

Examples of specific isolated antibodies provided by the present disclosure include the following illustrative antibodies: MOR-6032, MOR-7361, MOR-7480, MOR-7480.1, MOR-7480.1, MOR-7480.2, MOR-7483, MOR-7483, MOR-7483.1, and MOR-7483.2. The nucleotide and amino acid sequences of the heavy chain variable region, full length heavy chain for the IgG2 subclass, light chain variable region, and full length light chain of these antibodies are provided in this disclosure; an index of the SEQ ID NOs for these sequences is provided in Table 1. The amino acid sequences of the CDRs of these illustrative antibodies are shown in Table 2.

TABLE 1

Index of SEQ ID NOs

| | | Full length | | Variable Region | |
|---|---|---|---|---|---|
| Antibody | Chain | Amino Acid SEQ ID NO | Nucleotide SEQ ID NO | Amino Acid SEQ ID NO | Nucleotide SEQ ID NO |
| MOR-6032 | Heavy | 5 | 13 | 4 | 11 |
| | Light | 10 | 14 | 9 | 12 |
| MOR-7361 | Heavy | 19 | 27 | 18 | 25 |
| | Light | 24 | 28 | 23 | 26 |
| MOR-7480 | Heavy | 33 | 41 | 32 | 39 |
| | Light | 38 | 42 | 37 | 40 |
| MOR-7480.1 | Heavy | 44 | 49 | 43 | 47 |
| | Light | 46 | 50 | 45 | 48 |
| MOR-7480.2 | Heavy | 44 | 49 | 43 | 47 |
| | Light | 52 | 54 | 51 | 53 |
| MOR-7483 | Heavy | 33 | 41 | 32 | 39 |
| | Light | 57 | 59 | 56 | 58 |
| MOR-7483.1 | Heavy | 44 | 49 | 43 | 47 |
| | Light | 61 | 63 | 60 | 62 |
| MOR-7483.2 | Heavy | 44 | 49 | 43 | 47 |
| | Light | 65 | 67 | 64 | 66 |

TABLE 2

Amino Acid Sequence of CDRs

| Antibody | CDR | Sequence | SEQ ID NO |
|---|---|---|---|
| MOR-6032 | H-CDR1 | NSYAIS | 1 |
| | H-CDR2 | GIIPGFGTANYAQKFQG | 2 |
| | H-CDR3 | RKNEEDGGFDH | 3 |
| | L-CDR1 | SGDNLGDYYAS | 6 |
| | L-CDR2 | DDSNRPS | 7 |
| | L-CDR3 | QTWDGTLHFV | 8 |
| MOR-7361 | H-CDR1 | SDYYMH | 15 |
| | H-CDR2 | VISGSGSNTYYADSVKG | 16 |
| | H-CDR3 | RLYAQFEGDF | 17 |
| | L-CDR1 | SGDNIGSKYVS | 20 |
| | L-CDR2 | SDSERPS | 21 |
| | L-CDR3 | QSWDGSISRV | 22 |
| MOR-7480; MOR-7480.1; MOR-7480.2 | H-CDR1 | STYWIS | 29 |
| | H-CDR2 | KIYPGDSYTNYSPSFQG | 30 |
| | H-CDR3 | RGYGIFDY | 31 |
| | L-CDR1 | SGDNIGDQYAH | 34 |
| | L-CDR2 | QDKNRPS | 35 |
| | L-CDR3 | ATYTGFGSLAV | 36 |
| MOR-7483; MOR-7483.1; MOR-7483.2 | H-CDR1 | STYWIS | 29 |
| | H-CDR2 | KIYPGDSYTNYSPSFQG | 30 |
| | H-CDR3 | RGYGIFDY | 31 |
| | L-CDR1 | SGDNIGDQYAH | 34 |
| | L-CDR2 | QDKNRPS | 35 |
| | L-CDR3 | STYTFVGFTTV | 55 |

Antibodies of the present disclosure can be produced by techniques known in the art, including conventional monoclonal antibody methodology e.g., the standard somatic cell hybridization technique (See e.g., Kohler and Milstein, *Nature* 256:495 (1975), viral or oncogenic transformation of B lymphocytes, or recombinant antibody technologies as described in detail herein below.

Hybridoma production is a very well-established procedure. The common animal system for preparing hybridomas is the murine system. Immunization protocols and techniques for isolation of immunized splenocytes for fusion are known in the art. Fusion partners (e.g., murine myeloma cells) and fusion procedures are also known. One well-known method that may be used for making human 4-1BB antibodies provided by the present disclosure involves the use of a XenoMouse™ animal system. XenoMouse™ mice are engineered mouse strains that comprise large fragments of human immunoglobulin heavy chain and light chain loci and are deficient in mouse antibody production. See, e.g., Green et al., Nature Genetics 7:13-21 (1994) and WO2003/040170. The animal is immunized with a 4-1BB antigen. The 4-1BB antigen is isolated and/or purified 4-1BB, preferably 4-1BB. It may be a fragment of 4-1BB, such as the extracellular domain of 4-1BB, particularly a 4-1BB extracellular domain fragment comprising amino acid resides 115-156 of SEQ ID NO: 68. Immunization of animals can be carried out by any method known in the art. See, e.g., Harlow and Lane, Antibodies: A Laboratory Manual, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994,619. The 4-1BB antigen may be administered with an adjuvant to stimulate the immune response. Exemplary adjuvants include complete or incomplete Freund's adjuvant, RIBI (muramyl dipeptides) or ISCOM (immunostimulating complexes). After immunization of an animal with a 4-1BB antigen, antibody-producing immortalized cell lines are prepared from cells isolated from the immunized animal. After immunization, the animal is sacrificed and lymph node and/or splenic B cells are immortalized. Methods of immortalizing cells include, but are not limited to, transferring them with oncogenes, inflecting them with the oncogenic virus cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using 4-1BB, a portion thereof, or a cell expressing 4-1BB. 4-1BB antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

Antibodies of the disclosure can also be prepared using phage display methods. Such phage display methods for isolating human antibodies are established in the art, such as the HuCAL® Libraries as described further in Example 1. See also, for example: Achim Knappik, et al: Fully Synthetic Human Combinatorial Antibody Libraries (HuCAL) Based on Modular Consensus Frameworks and CDRs Randomized with Trinucleotides. J. Mol. Biol. (2000) 296, 57-86.

B-2. Antigen-Binding Fragments

In some other aspects, the present disclosure provides antigen-binding fragments of any of the 4-1BB antibodies provided by the present disclosure.

The antigen-binding fragment may comprise any sequences of the antibody. In some embodiments, the antigen-binding fragment comprises the amino acid sequence of: (1) a light chain of a 4-1BB antibody; (2) a heavy chain of a 4-1BB antibody; (3) a variable region from the light chain of a 4-1BB antibody; (4) a variable region from the heavy chain of a 4-1BB antibody; (5) one or more CDRs (two, three, four, five, or six CDRs) of a 4-1BB antibody; or (6) three CDRs from the light chain and three CDRs from the heavy chain of a 4-1BB antibody.

In some particular embodiments, the disclosure provides an antigen-binding fragment of an antibody selected from: MOR-6032, MOR-7361, MOR-7480, MOR-7480.1, MOR-7480.2, MOR-7483, MOR-7483.1, or MOR-7483.2.

In some other particular embodiments, the antigen-binding fragments of an 4-1BB antibody include: (i) a Fab fragment, which is a monovalent fragment consisting of the $V_L$, $V_H$, $C_L$ and $C_H1$ domains; (ii) a F(ab')$_2$ fragment, which is a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody; (v) a dAb fragment (Ward et al., (1989) Nature 341:544-546), which consists of a $V_H$ domain; (vi) an isolated CDR, and (vii) single chain antibody (scFv), which is a polypeptide comprising a $V_L$ region of an antibody linked to a $V_H$ region of an antibody. Bird et al., (1988) Science 242:423-426 and Huston et al., (1988) Proc. Natl. Acad. Sci. USA 85:5879-5883.

In some particular embodiments, the antigen-binding fragment is a Fab fragment selected from the group consisting of Fab-6032, Fab-7361, Fab-7480, and Fab-7483.

B-3. Antibody Derivatives

In some further aspects, the present disclosure provides derivatives of any of the 4-1BB antibodies provided by the present disclosure.

In one aspect, the antibody derivative is derived from modifications of the amino acid sequences of an illustrative antibody ("parent antibody") of the disclosure while conserving the overall molecular structure of the parent antibody amino acid sequence. Amino acid sequences of any regions of the parent antibody chains may be modified, such as framework regions, CDR regions, or constant regions. Types of modifications include substitutions, insertions, deletions, or combinations thereof, of one or more amino acids of the parent antibody. In some embodiments, the antibody derivative comprises an $V_H$ region that is at least 65%, at least 75%, at least 85%, at least 90%, at least 95%, at least 96%, at least 97%, at least 98%, or at least 99% identical to an amino acid sequence as set forth in any of SEQ ID NOs: 4, 18, 32, or 43. In some other embodiments, the antibody derivative comprises an $V_L$ region that is at least 65%, at least 75%, at least 85%, at least 90%, at least 95%, at least 96%, at least 97%, at least 98%, or at least 99% identical to an amino acid sequence as set forth in any of SEQ ID NOs: 9, 23, 37, 45, 51, 56, 60, or 64. In some particular embodiments, the derivative comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to an amino acid sequence as set forth in any of SEQ ID NOs: 4, 18, 32, 43, 9, 23, 37, 45, 51, 56, 60, or 64.

Amino acid substitutions encompass both conservative substitutions and non-conservative substitutions. The term "conservative amino acid substitution" means a replacement of one amino acid with another amino acid where the two amino acids have similarity in certain physico-chemical properties such as polarity, charge, solubility, hydrophobicity, hydrophilicity, and/or the amphipathic nature of the residues involved. For example, substitutions typically may be made within each of the following groups: (a) nonpolar (hydrophobic) amino acids, such as alanine, leucine, isoleucine, valine, proline, phenylalanine, tryptophan, and methionine; (b) polar neutral amino acids, such as glycine, serine, threonine, cysteine, tyrosine, asparagine, and glutamine; (c) positively charged (basic) amino acids, such as arginine, lysine, and histidine; and (d) negatively charged (acidic) amino acids, such as aspartic acid and glutamic acid.

The modifications may be made in any positions of the amino acid sequences of the antibody, including the CDRs, framework regions, or constant regions. In one embodiment, the present disclosure provides an antibody derivative that contains the $V_H$ and $V_L$ CDR sequences of an illustrative antibody of this disclosure, yet contains framework sequences different from those of the illustrative antibody. Such framework sequences can be obtained from public DNA databases or published references that include germline antibody gene sequences. For example, germline DNA sequences for human heavy and light chain variable region genes can be found in the Genbank database or in the "VBase" human germline sequence database (Kabat, E. A., et al., Sequences of Proteins of Immunological Interest, Fifth Edition, U.S. Department of Health and Human Services, NIH Publication No. 91-3242 (1991); Tomlinson, I. M., et al., *J. Mol. Biol.* 227:776-798 (1992); and Cox, J. P. L. et al., *Eur. J. Immunol.* 24:827-836 (1994)). Framework sequences that may be used in constructing an antibody derivative include those that are structurally similar to the framework sequences used by illustrative antibodies of the disclosure, e.g., similar to the $V_H$3-23 framework sequences and/or the $V_L$ λ3 or λ1-13 framework sequences used by illustrative antibodies of the disclosure. For example, the H-CDR1, H-CDR2, and H-CDR3 sequences, and the L-CDR1, L-CDR2, and L-CDR3 sequences of an illustrative antibody can be grafted onto framework regions that have the identical sequence as that found in the germline immunoglobulin gene from which the framework sequence derive, or the CDR sequences can be grafted onto framework regions that contain one or more mutations as compared to the germline sequences.

In a particular embodiment, the antibody derivative is a chimeric antibody which comprises an amino acid sequence of an illustrative antibody of the disclosure. In one example, one or more CDRs from one or more illustrative human antibodies are combined with CDRs from an antibody from a non-human animal, such as mouse or rat. In another example, all of the CDRs of the chimeric antibody are derived from one or more illustrative antibodies. In some particular embodiments, the chimeric antibody comprises one, two, or three CDRs from the heavy chain variable region or from the light chain variable region of an illustrative antibody. Chimeric antibodies can be generated using conventional methods known in the art.

Another type of modification is to mutate amino acid residues within the CDR1, CDR2 and/or CDR3 regions of the $V_H$ and/or $V_L$ chain. Site-directed mutagenesis or PCR-mediated mutagenesis can be performed to introduce the mutation(s) and the effect on antibody binding, or other functional property of interest, can be evaluated in in vitro or in vivo assays known in the art. Typically, conservative substitutions are introduced. The mutations may be amino acid additions and/or deletions. Moreover, typically no more than one, two, three, four or five residues within a CDR region are altered. In some embodiments, the antibody derivative comprises 1, 2, 3, or 4 amino acid substitutions in the H-CDRs and/or in the light chain CDRs. In another embodiment, the amino acid substitution is to change one or more cysteines in an antibody to another residue, such as, without limitation, alanine or serine. The cysteine may be a canonical or non-canonical cysteine. In one embodiment, the antibody derivative has 1, 2, 3, or 4 conservative amino acid substitutions in the H-CDR regions relative to the amino acid sequences of an illustrative antibody.

Modifications may also be made to the framework residues within the $V_H$ and/or $V_L$ regions. Typically, such framework variants are made to decrease the immunogenicity of the antibody. One approach is to "backmutate" one or more framework residues to the corresponding germline sequence. An antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis or PCR-mediated mutagenesis. Several of the illustrative antibodies of the present disclosure underwent such "back-mutations" to certain germline sequences, as described further in Example 6.

In addition, modifications may also be made within the Fc region of an illustrative antibody, typically to alter one or more functional properties of the antibody, such as serum half-life, complement fixation, Fc receptor binding, and/or antigen-dependent cellular cytotoxicity. In one example, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody. In another case, the Fc hinge region of an antibody is mutated to decrease the biological half life of the antibody.

Furthermore, an antibody of the disclosure may be modified to alter its potential glycosylation site or pattern. Both illustrative antibodies MOR-7480 and MOR-7483, and any germlined variants thereof, and antibodies that comprise the amino acid sequences of the heavy chain variable region of MOR-7480 and MOR-7483, comprise a potential N-linked glycosylation site (NYS) at asparagine 59 in the heavy chain variable domain. IgG versions of these antibodies further comprise a second N-linked glycosylation site in the heavy chain Fc domain. More specifically, for the IgG2 version of these antibodies, the Fc N-linked glycosylation site (NST) occurs at asparagine 292 in the heavy chain CH2 domain. Thus, each heavy chain can comprise 0-, 1- (at either Fab or Fc) or 2-glycan occupancy such that an antibody comprising two heavy and two light chains can comprise any combination ranging from O-glycan occupancy (i.e., no glycosylation at any of four potential glycosylation sites) to 4-glycan occupancy (i.e., glycosylated at both Fab and Fc sites in each chain). In another aspect, the present disclosure provide an derivative of an 4-1BB antibody of the disclosure that contains at least one mutation in an variable region of a light chain or heavy chain that changes the pattern of glycosylation in the variable region. Such an antibody derivative may have an increased affinity and/or a modified specificity for binding an antigen. The mutations may add a novel glycosylation site in the V region, change the location of one or more V region glycosylation site(s), or remove a pre-existing V region glycosylation site. In one embodiment, the present disclosure provides a derivative of an 4-1BB antibody having a potential N-linked glycosylation site at asparagine 59 in the heavy chain variable region, wherein the potential N-linked glycosylation site in one heavy chain variable region is removed. In another embodiment, the present disclosure provides a derivative of a 4-1BB antibody having a potential N-linked glycosylation site at asparagine 59 in the heavy chain variable region, wherein the potential N-linked glycosylation site in both heavy chain variable regions is removed. Method of altering the glycosylation pattern of an antibody is known in the art, such as those described in U.S. Pat. No. 6,933,368, the disclosure of which incorporated herein by reference.

In another aspect, the present disclosure provides an antibody derivative that comprises a 4-1BB antibody, or antigen-binding fragment thereof, as described herein, linked to an additional molecular entity. Examples of additional molecular entities include pharmaceutical agents, peptides or proteins, detection agent or labels, and antibodies.

In some embodiments, the antibody derivative comprises an antibody of the disclosure linked to a pharmaceutical agent. Examples of pharmaceutical agents include cytotoxic agents or other cancer therapeutic agents, and radioactive isotopes. Specific examples of cytotoxic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for linking an antibody to a pharmaceutical agent are known in the art, such as using various linker technologies. Examples of linker types include hydrazones, thioethers, esters, disulfides and peptide-containing linkers. For further discussion of linkers and methods for linking therapeutic agents to antibodies, see also Saito et al., *Adv. Drug Deliv. Rev.* 55:199-215 (2003); Trail, et al., *Cancer Immunol. Immunother.* 52:328-337 (2003); Payne, *Cancer Cell* 3:207-212 (2003); Allen, *Nat. Rev. Cancer* 2:750-763 (2002); Pastan, I. and Kreitman, *Curr. Opin. Investig. Drugs* 3:1089-1091 (2002); Senter, P. D. and Springer, C. J. (2001) *Adv. Drug Deliv. Rev.* 53:247-264.

In a particular embodiment, the antibody derivative is a 4-1BB antibody multimer, which is a multimeric form of a 4-1BB antibody, such as antibody dimers, trimers, or higher-order multimers of monomeric antibodies. Individual monomers within an antibody multimer may be identical or different. In addition, individual antibodies within a multimer may have the same or different binding specificities. Multimerization of antibodies may be accomplished through natural aggregation of antibodies. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art, such as through using crosslinking agents. Suitable crosslinkers include those that are heterobifunctional, having two distinctly reactive groups separated by an appropriate spacer (such as m-maleimidobenzoyl-N-hydroxysuccinimide ester, succinimidyl 4-(maleimidomethyl)cyclohexane-1-carboxylate, and N-succinimidyl S-acethylthio-acetate) or homobifunctional (such as disuccinimidyl suberate). Such linkers are commercially available from, for example, Pierce Chemical Company, Rockford, Ill. Antibodies can also be made to multimerize through recombinant DNA techniques known in the art.

Examples of other antibody derivatives provided by the present disclosure include single chain antibodies, diabodies, domain antibodies, nanobodies, and unibodies. A "single-chain antibody" (scFv) consists of a single polypeptide chain comprising a $V_L$ domain linked to a $V_H$ domain wherein $V_L$ domain and $V_H$ domain are paired to form a monovalent molecule. Single chain antibody can be prepared according to method known in the art (see, for example, Bird et al., (1988) Science 242:423-426 and Huston et al., (1988) Proc. Natl. Acad. Sci. USA 85:5879-5883). A "diabody" consists of two chains, each chain comprising a heavy chain variable region connected to a light chain variable region on the same polypeptide chain connected by a short peptide linker, wherein the two regions on the same chain do not pair with each other but with complementary domains on the other chain to form a bispecific molecule. Methods of preparing diabodies are known in the art (See, e.g., Holliger P. et al., (1993) Proc. Natl. Acad. Sci. USA 90:6444-6448, and Poljak R. J. et al., (1994) Structure 2:1121-1123). Domain antibodies (dAbs) are small functional binding units of antibodies, corresponding to the variable regions of either the heavy or light chains of antibodies. Domain antibodies are well expressed in bacterial, yeast, and mammalian cell systems. Further details of domain antibodies and methods of production thereof are known in the art (see, for example, U.S. Pat. Nos. 6,291,158; 6,582,915; 6,593,081; 6,172,197; 6,696,245; European Patents 0368684 & 0616640; WO05/035572, WO04/101790, WO04/081026, WO04/058821, WO04/003019 and WO03/002609). Nanobodies are derived from the heavy chains of an antibody. A nanobody typically comprises a single variable domain and two constant domains (CH2 and CH3) and retains antigen-binding capacity of the original antibody. Nanobodies can be prepared by methods known in the art (See e.g., U.S. Pat. No. 6,765,087, U.S. Pat. No. 6,838,254, WO 06/079372). Unibodies consist of one light chain and one heavy chain of a IgG4 antibody. Unibodies may be made by the removal of the hinge region of IgG4 antibodies. Further details of unibodies and methods of preparing them may be found in WO2007/059782.

C. Nucleic Acids, Vectors, Host Cells, and Recombinant Methods of Producing 4-1BB Antibodies Another aspect of the disclosure provides an isolated nucleic acid molecule that comprises a nucleotide sequence encoding an amino acid sequence of a binding molecule provided by the present disclosure. The amino acid sequence encoded by the nucleotide sequence may be any portion of an antibody, such as a CDR, a sequence comprising one, two, or three CDRs, a variable region of a heavy chain, variable region of a light chain, or may be a full-length heavy chain or full length light chain. A nucleic acid of the disclosure can be, for example, DNA or RNA, and may or may not contain intronic sequences. Typically, the nucleic acid is a cDNA molecule.

In some embodiments, the disclosure provides an isolated nucleic acid molecule that comprises or consists of a nucleotide sequence encoding an amino acid sequence selected from the group consisting of: (1) amino acid sequence of a H-CDR3 or L-CRD3 of an illustrative antibody; (2) a variable region of a heavy chain or variable region of a light chain of an illustrative antibody; or (3) a full length heavy chain or full length light chain of an illustrative antibody.

In other embodiments, the nucleic acid molecule comprises or consists of a nucleotide sequence that encodes an amino acid sequence as set forth in any one of SEQ ID NOs:1-10, 15-24, 29-38, 43, 44, 45, 46, 51, 52, 55-57, 60, 61, 64, and 65.

In still other embodiments, the nucleic acid molecule comprises or consists of nucleotide sequence selected from the group consisting of SEQ ID NOs: 11-14, 25-28, 39-42, 47-50, 53, 54, 58, 59, 62, 63, 66, and 67.

Nucleic acids of the disclosure can be obtained using any suitable molecular biology techniques. For antibodies expressed by hybridomas, cDNAs encoding the light and heavy chains of the antibody made by the hybridoma can be obtained by PCR amplification or cDNA cloning techniques. For antibodies obtained from an immunoglobulin gene library (e.g., using phage display techniques), the nucleic acid encoding the antibody can be recovered from the library.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. The IgG1 constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the $V_H$- and $V_L$-encoding DNA fragments are operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ regions joined by the flexible linker (see e.g., Bird et al., *Science* 242:423-426 (1988); Huston et al., *Proc. Natl. Acad. Sci. USA* 85:5879-5883 (1988); and McCafferty et al., *Nature* 348:552-554 (1990)).

The present disclosure further provides a vector that comprises a nucleic acid molecule provided by the present disclosure. The nucleic acid molecule may encode a portion of a light chain or heavy chain (such as a CDR or a variable region), a full-length light or heavy chain, polypeptide that comprises a portion or full-length of a heavy or light chain, or an amino acid sequence of an antibody derivative or antigen-binding fragment. In some embodiments, the vector is an expression vector useful for the expression of a binding molecule, such as an antibody or an antigen binding fragment thereof.

To express a binding molecule of the disclosure, DNAs encoding partial or full-length light and heavy chains are inserted into expression vectors such that the DNA molecules are operatively linked to transcriptional and translational control sequences. In this context, the term "operatively linked" means that an antibody gene is ligated into a vector such that transcriptional and translational control sequences within the vector serve their intended function of regulating the transcription and translation of the DNA molecule. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by any suitable methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype and subclass by inserting them into expression vectors already encoding heavy chain constant and light chain constant regions of the desired isotype and subclass such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the expression vectors of the disclosure typically carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Examples of regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by any suitable techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the disclosure in either prokaryotic or eukaryotic host cells, expression of antibodies in eukaryotic cells, and typically mammalian host cells, is most typical.

The present disclosure further provides a host cell containing a nucleic acid molecule provided by the present disclosure. The host cell can be virtually any cell for which expression vectors are available. It may be, for example, a higher eukaryotic host cell, such as a mammalian cell, a lower eukaryotic host cell, such as a yeast cell, and may be a prokaryotic cell, such as a bacterial cell. Introduction of the recombinant nucleic acid construct into the host cell can be effected by calcium phosphate transfection, DEAE, dextran mediated transfection, electroporation or phage infection.

Suitable prokaryotic hosts for transformation include *E. coli, Bacillus subtilis, Salmonella typhimurium* and various species within the genera *Pseudomonas, Streptomyces,* and *Staphylococcus.*

Mammalian host cells for expressing a binding molecule of the disclosure include, for example, Chinese Hamster Ovary (CHO) cells (including dhfr-CHO cells, described in Urlaub and Chasin, *Proc. Natl. Acad. Sci. USA* 77:4216-4220 (1980), used with a DHFR selectable marker, e.g., as described in Kaufman and Sharp, *J. Mol. Biol.* 159:601-621 (1982), NS0 myeloma cells, COS cells and Sp2 cells. In particular, for use with NS0 myeloma or CHO cells, another expression system is the GS (glutamine synthetase) gene expression system disclosed in WO 87/04462, WO 89/01036 and EP 338,841. When expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using any suitable protein purification methods.

D. Compositions

In other aspects, the present disclosure provides a composition containing a binding molecule provided by the disclosure. In one aspect, the composition is a pharmaceutical composition comprising a binding molecule and a pharmaceutically acceptable carrier. The compositions can be prepared by conventional methods known in the art.

In some embodiments, present disclosure provides a composition comprising an antibody, or an antigen-binding portion thereof, provided by the present disclosure and a pharmaceutically acceptable carrier, wherein said antibody comprises a variable domain comprising the CDR amino acid sequence set forth in SEQ ID NO:30, and wherein said composition comprises not more than about 11%, 10%, 8%, 5%, 3%, or 2% of said antibody, or antigen-binding portion, that is glycosylated at the asparagine of said amino acid sequence compared with the total amount of antibody, or antigen-binding portion thereof, present in said composition. In another embodiment, the composition comprises at least about 2% of said antibody, or antigen-binding portion, that is glycosylated at the asparagine of said amino acid sequence of SEQ ID NO:30 compared with the total amount of antibody, or antigen-binding portion thereof, present in said composition.

The term "pharmaceutically acceptable carrier" refers to any inactive substance that is suitable for use in a formulation for the delivery of a binding molecule. A carrier may be an antiadherent, binder, coating, disintegrant, filler or diluent, preservative (such as antioxidant, antibacterial, or antifungal agent), sweetener, absorption delaying agent, wetting agent, emulsifying agent, buffer, and the like. Examples of suitable pharmaceutically acceptable carriers include water, ethanol, polyols (such as glycerol, propylene glycol, polyethylene glycol, and the like) dextrose, vegetable oils (such as olive oil), saline, buffer, buffered saline, and isotonic agents such as sugars, polyalcohols, sorbitol, and sodium chloride.

The compositions may be in any suitable forms, such as liquid, semi-solid, and solid dosage forms. Examples of liquid dosage forms include solution (e.g., injectable and infusible solutions), microemulsion, liposome, dispersion, or suspension. Examples of solid dosage forms include tablet, pill, capsule, microcapsule, and powder. A particular form of the composition suitable for delivering a binding molecule is a sterile liquid, such as a solution, suspension, or dispersion, for injection or infusion. Sterile solutions can be prepared by incorporating the antibody in the required amount in an appropriate carrier, followed by sterilization microfiltration. Generally, dispersions are prepared by incorporating the antibody into a sterile vehicle that contains a basic dispersion medium and other carriers. In the case of sterile powders for the preparation of sterile liquid, methods of preparation include vacuum drying and freeze-drying (lyophilization) to yield a powder of the active ingredient plus any additional desired ingredient from a previously sterile-filtered solution thereof. The various dosage forms of the compositions can be prepared by conventional techniques known in the art.

The relative amount of a binding molecule included in the composition will vary depending upon a number of factors, such as the specific binding molecule and carriers used, dosage form, and desired release and pharmacodynamic characteristics. The amount of a binding molecule in a single dosage form will generally be that amount which produces a therapeutic effect, but may also be a lesser amount. Generally, this amount will range from about 0.01 percent to about 99 percent, from about 0.1 percent to about 70 percent, or from about 1 percent to about 30 percent relative to the total weight of the dosage form.

In addition to the binding molecule, one or more additional therapeutic agents may be included in the composition. Examples of additional therapeutic agents are described herein below. The suitable amount of the additional therapeutic agent to be included in the composition can be readily selected by a person skilled in the art, and will vary depending on a number of factors, such as the particular agent and carriers used, dosage form, and desired release and pharmacodynamic characteristics. The amount of the additional therapeutic agent included in a single dosage form will generally be that amount of the agent which produces a therapeutic effect, but may be a lesser amount as well.

E. Use of the Binding Molecules and Pharmaceutical Compositions

Binding molecules and pharmaceutical compositions provided by the present disclosure are useful for therapeutic, diagnostic, or other purposes, such as enhancing an immune response, treating cancer, enhancing efficacy of other cancer therapy, enhancing vaccine efficacy, or treating autoimmune diseases. Thus, in other aspects, the present disclosure provides methods of using the binding molecules or pharmaceutical compositions. In one aspect, the present disclosure provides a method of treating a disorder in a mammal, which comprises administering to the mammal in need of treatment a therapeutically effective amount of a binding molecule provided by the disclosure. The binding molecule may be a 4-1BB agonist or antagonist. In some embodiments, the binding molecule is a 4-1BB agonist. In some embodiments, the mammal is a human.

In some embodiments, the disorder is a cancer. A variety of cancers where 4-1BB is implicated, whether malignant or benign and whether primary or secondary, may be treated or prevented with a method provided by the disclosure. Examples of such cancers include lung cancers such as bronchogenic carcinoma (e.g., squamous cell carcinoma, small cell carcinoma, large cell carcinoma, and adenocarcinoma), alveolar cell carcinoma, bronchial adenoma, chondromatous hamartoma (noncancerous), and sarcoma (cancerous); heart cancer such as myxoma, fibromas, and rhabdomyomas; bone cancers such as osteochondromas, condromas, chondroblastomas, chondromyxoid fibromas, osteoid osteomas, giant cell tumors, chondrosarcoma, multiple myeloma, osteosarcoma, fibrosarcomas, malignant fibrous histiocytomas, Ewing's tumor (Ewing's sarcoma), and reticulum cell sarcoma; brain cancer such as gliomas (e.g., glioblastoma multiforme), anaplastic astrocytomas, astrocytomas, oligodendrogliomas, medulloblastomas, chordoma, Schwannomas, ependymomas, meningiomas, pituitary adenoma, pinealoma, osteomas, hemangioblastomas, craniopharyngiomas, chordomas, germinomas, teratomas, dermoid cysts, and angiomas; cancers in digestive system such as leiomyoma, epidermoid carcinoma, adenocarcinoma, leiomyosarcoma, stomach adenocarcinomas, intestinal lipomas, intestinal neurofibromas, intestinal fibromas, polyps in large intestine, and colorectal cancers; liver cancers such as hepatocellular adenomas, hemangioma, hepatocellular carcinoma, fibrolamellar carcinoma, cholangiocarcinoma, hepatoblastoma, and angiosarcoma; kidney cancers such as kidney adenocarcinoma, renal cell carcinoma, hypernephroma, and transitional cell carcinoma of the renal pelvis; bladder cancers; hematological cancers such as acute lymphocytic (lymphoblastic) leukemia, acute myeloid (myelocytic, myelogenous, myeloblastic, myelomonocytic) leukemia, chronic lymphocytic leukemia (e.g., Sezary syndrome and hairy cell leukemia), chronic myelocytic (myeloid, myelogenous, granulocytic) leukemia, Hodgkin's lymphoma, non-Hodgkin's lymphoma, B cell lymphoma, mycosis fungoides, and myeloproliferative disorders (including myeloproliferative disorders such as polycythemia vera, myelofibrosis, thrombocythemia, and chronic myelocytic leukemia); skin cancers such as basal cell carcinoma, squamous cell carcinoma, melanoma, Kaposi's sarcoma, and Paget's disease; head and neck cancers; eye-related cancers such as retinoblastoma and intraoccular melanocarcinoma; male reproductive system cancers such as benign prostatic hyperplasia, prostate cancer, and testicular cancers (e.g., seminoma, teratoma, embryonal carcinoma, and choriocarcinoma); breast cancer; female reproductive system cancers such as uterine cancer (endometrial carcinoma), cervical cancer (cervical carcinoma), cancer of the ovaries (ovarian carcinoma), vulvar carcinoma, vaginal carcinoma, fallopian tube cancer, and hydatidiform mole; thyroid cancer (including papillary, follicular, anaplastic, or medullary cancer); pheochromocytomas (adrenal gland); noncancerous growths of the parathyroid glands; pancreatic cancers; and hematological cancers such as leukemias, myelomas, non-Hodgkin's lymphomas, and Hodgkin's lymphomas.

In some other embodiments, the disorder is an autoimmune disease. Examples of autoimmune diseases that may be treated with the binding molecules include autoimmune encephalomyelitis, lupus erythematosus, and rheumatoid arthritis. The binding molecule may also be used to treat inflammation (such as allergic asthma) and chronic graft-versus-host disease, In another aspect, the present disclosure provides a method of enhancing an immune response in a mammal, which comprises administering to the mammal a therapeutically effective amount of a binding molecule provided by the disclosure. In some embodiments, the binding molecule is a 4-1BB antibody or antigen-binding fragment thereof and the mammal is a human. In a further embodiment, the binding molecule is 4-1BB agonist antibody or an antigen-binding fragment thereof. The term "enhancing immune response" or its grammatical variations, means stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated response), and may be a primary or secondary immune response. Examples of enhancement of immune response include increased CD4+ helper T cell activity and generation of cytolytic T cells. The enhancement of immune response can be assessed using a number of in vitro or in vivo measurements known to those skilled in the art, including, but not limited to, cytotoxic T lymphocyte assays, release of cytokines (for example IL-2 production), regression of tumors, survival of tumor bearing animals, antibody production, immune cell proliferation, expression of cell surface markers, and cytotoxicity. Typically, methods of the disclosure enhance the immune response by a mammal when compared to the immune response by an untreated mammal or a mammal not treated using the claimed methods. In one embodiment, the binding molecule is used to enhance the immune response of a human to a microbal pathogen (such as a virus). In another embodiment, the binding molecule is used to enhance the immune response of a human to a vaccine. The binding molecule may be a 4-1BB agonist or antagonist. In some embodiments, the binding molecule is a 4-1BB agonist. In one embodiment, the method enhances a cellular immune response, particularly a cytotoxic T cell response. In another embodiment, the cellular immune response is a T helper cell response. In still another embodiment, the immune response is a cytokine production, particularly IL-2 production. The binding molecule may be used to enhance the immune response of a human to a microbial pathogen (such as a virus) or to a vaccine. The binding molecule may be a 4-1BB agonist or antagonist. In some embodiments, the binding molecule is a 4-1BB agonist.

In practicing the therapeutic methods, the binding molecules may be administered alone as monotherapy, or administered in combination with one or more additional therapeutic agents or therapies. Thus, in another aspect, the present disclosure provides a combination therapy, which comprises a binding molecule in combination with one or more additional therapies or therapeutic agents for separate, sequential or simultaneous administration. The term "additional therapy" refers to a therapy which does not employ a binding molecule provided by the disclosure as a therapeutic agent. The term "additional therapeutic agent" refers to any therapeutic agent other than a binding molecule provided by the disclosure. In one particular aspect, the present disclosure provides a combination therapy for treating cancer in a mammal, which comprises administering to the mammal a therapeutically effective amount of a binding molecule provided by the disclosure in combination with one or more additional therapeutic agents. In a further embodiment, the mammal is a human.

A wide variety of cancer therapeutic agents may be used in combination with a binding molecule provided by the present disclosure. One of ordinary skill in the art will recognize the presence and development of other cancer therapies which can be used in combination with the methods and binding molecules of the present disclosure, and will not be restricted to those forms of therapy set forth herein. Examples of categories of additional therapeutic agents that may be used in the combination therapy for treating cancer include (1) chemotherapeutic agents, (2) immunotherapeutic agents, and (3) hormone therapeutic agents.

The term "chemotherapeutic agent" refers to a chemical or biological substance that can cause death of cancer cells, or interfere with growth, division, repair, and/or function of cancer cells. Examples of chemotherapeutic agents include those that are disclosed in WO 2006/129163, and US 20060153808, the disclosures of which are incorporated herein by reference. Examples of particular chemotherapeutic agents include: (1) alkylating agents, such as chlorambucil (LEUKERAN), mcyclophosphamide (CYTOXAN), ifosfamide (IFEX), mechlorethamine hydrochloride (MUSTARGEN), thiotepa (THIOPLEX), streptozotocin (ZANOSAR), carmustine (BICNU, GLIADEL WAFER), lomustine (CEENU), and dacarbazine (DTIC-DOME); (2) alkaloids or plant vinca alkaloids, including cytotoxic antibiotics, such as doxorubicin (ADRIAMYCIN), epirubicin (ELLENCE, PHARMORUBICIN), daunorubicin (CERUBIDINE, DAUNOXOME), nemorubicin, idarubicin (IDAMYCIN PFS, ZAVEDOS), mitoxantrone (DHAD, NOVANTRONE). dactinomycin (actinomycin D, COSMEGEN), plicamycin (MITHRACIN), mitomycin (MUTAMYCIN), and bleomycin (BLENOXANE), vinorelbine tartrate (NAVELBINE)), vinblastine (VELBAN), vincristine (ONCOVIN), and vindesine (ELDISINE); (3) antimetabolites, such as capecitabine (XELODA), cytarabine (CYTOSAR-U), fludarabine (FLUDARA), gemcitabine (GEMZAR), hydroxyurea (HYDRA), methotrexate (FOLEX, MEXATE, TREXALL), nelarabine (ARRANON), trimetrexate (NEUTREXIN), and pemetrexed (ALIMTA); (4) Pyrimidine antagonists, such as 5-fluorouracil (5-FU); capecitabine (XELODA), raltitrexed (TOMUDEX), tegafur-uracil (UFTORAL), and gemcitabine (GEMZAR); (5) taxanes, such as docetaxel (TAXOTERE), paclitaxel (TAXOL); (6) platinum drugs, such as cisplatin (PLATINOL) and carboplatin (PARAPLATIN), and oxaliplatin (ELOXATIN); (7) topoisomerase inhibitors, such as irinotecan (CAMPTOSAR), topotecan (HYCAMTIN), etoposide (ETOPOPHOS, VEPESSID, TOPOSAR), and teniposide (VUMON); (8) epipodophyllotoxins (podophyllotoxin derivatives), such as etoposide (ETOPOPHOS, VEPESSID, TOPOSAR); (9) folic acid derivatives, such as leucovorin (WELLCOVORIN); (10) nitrosoureas, such as carmustine (BiCNU), lomustine (CeeNU); (11) inhibitors of receptor tyrosine kinase, including epidermal growth factor receptor (EGFR), vascular endothelial growth factor (VEGF), insulin receptor, insulin-like growth factor receptor (IGFR), hepatocyte growth factor receptor (HGFR), and platelet-derived growth factor receptor (PDGFR), such as gefitinib (IRESSA), erlotinib (TARCEVA), bortezomib (VELCADE), imatinib mesylate (GLEEVEC), genefitinib, lapatinib, sorafenib, thalidomide, sunitinib (SUTENT), axitinib, rituximab (RITUXAN, MABTHERA), trastuzumab (HERCEPTIN), cetuximab (ERBITUX), bevacizumab (AVASTIN), and ranibizumab (LUCENTIS), lym-1 (ONCOLYM), antibodies to insulin-like growth factor-1 receptor (IGF-1R) that are disclosed in WO2002/053596); (12) angiogenesis inhibitors, such as bevacizumab (AVASTIN), suramin (GERMANIN), angiostatin, SU5416, thalidomide, and matrix metalloproteinase inhibitors (such as batimastat and marimastat), and those that are disclosed in WO2002055106; and (13) proteasome inhibitors, such as bortezomib (VELCADE).

The term "immunotherapeutic agents" refers to a chemical or biological substance that can enhance an immune response of a mammal. Examples of immunotherapeutic agents include: *bacillus* Calmette-Guerin (BCG); cytokines such as interferons; vaccines such as MyVax personalized immunotherapy, Onyvax-P, Oncophage, GRNVAC1, Favld, Provenge, GVAX, Lovaxin C, BiovaxID, GMXX, and NeuVax; and antibodies such as alemtuzumab (CAMPATH), bevacizumab (AVASTIN), cetuximab (ERBITUX), gemtuzunab ozogamicin (MYLOTARG), ibritumomab tiuxetan (ZEVALIN), panitumumab (VECTIBIX), rituximab (RITUXAN, MABTHERA), trastuzumab (HERCEPTIN), tositumomab (BEXXAR), ipilimumab (YERVOY) tremelimumab, CAT-3888, agonist antibodies to OX40 receptor (such as those disclosed in WO2009/079335), agonist antibodies to CD40 receptor (such as those disclosed in WO2003/040170, and TLR-9 agonists (such as those disclosed in WO2003/015711, WO2004/016805, and WO2009/022215).

The term "hormone therapeutic agent" refers to a chemical or biological substance that inhibits or eliminates the production of a hormone, or inhibits or counteracts the effect of a hormone on the growth and/or survival of cancerous cells. Examples of such agents suitable for the methods herein include those that are disclosed in US20070117809. Examples of particular hormone therapeutic agents include tamoxifen (NOLVADEX), toremifene (Fareston), fulvestrant (FASLODEX), anastrozole (ARIMIDEX), exemestane (AROMASIN), letrozole (FEMARA), megestrol acetate (MEGACE), goserelin (ZOLADEX), and leuprolide (LUPRON). The binding molecules of this disclosure may also be used in combination with non-drug hormone therapies such as (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

The combination therapy for treating cancer also encompasses the combination of a binding molecule with surgery to remove a tumor. The binding molecule may be administered to the mammal before, during, or after the surgery.

The combination therapy for treating cancer also encompasses combination of a binding molecule with radiation therapy, such as ionizing (electromagnetic) radiotherapy (e.g., X-rays or gamma rays) and particle beam radiation therapy (e.g., high linear energy radiation). The source of radiation can be external or internal to the mammal. The binding molecule may be administered to the mammal before, during, or after the radiation therapy.

The binding molecules and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The antibodies and compositions of the disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific antibody being used, the rate of absorption desired, specific formulation or dosage form used, type or severity of the disorder being treated, the specific site of action, and conditions of the patient, and can be readily selected by a person skilled in the art The term "therapeutically effective amount" of a binding molecule refers to an amount that is effective for an intended therapeutic purpose. For example, in the context of enhancing an immune response, a "therapeutically effective amount" is any amount that is effective in stimulating, evoking, increasing, improving, or augmenting any response of a mammal's immune system. In the context of treating a disease, a "therapeutically effective amount" is any amount that is sufficient to cause any desirable or beneficial effect in the mammal being treated. Specifically, in the treatment of cancer, examples of desirable or beneficial effects include inhibition of further growth or spread of cancer cells, death of cancer cells, inhibition of reoccurrence of cancer, reduction of pain associated with the cancer, or improved survival of the mammal. The therapeutically effective amount of a 4-1BB antibody usually ranges from about 0.001 to about 500 mg/kg, and more usually about 0.01 to about 100 mg/kg, of the body weight of the mammal. For example, the amount can be about 0.3 mg/kg, 1 mg/kg, 3 mg/kg, 5 mg/kg, 10 mg/kg, 50 mg/kg, or 100 mg/kg of body weight of the mammal. In some embodiments, the therapeutically effective amount of a 4-1BB antibody is in the range of about 0.01-30 mg/kg of body weight of the mammal. In some other embodiments, the therapeutically effective amount of a 4-1BB antibody is in the range of about 0.05-15 mg/kg of body weight of the mammal. The precise dosage level to be administered can be readily determined by a person skilled in the art and will depend on a number of factors, such as the type, and severity of the disorder to be treated, the particular binding molecule employed, the route of administration, the time of administration, the duration of the treatment, the particular additional therapy employed, the age, sex, weight, condition, general health and prior medical history of the patient being treated, and like factors well known in the medical arts.

A binding molecule or composition is usually administered on multiple occasions. Intervals between single doses can be, for example, weekly, monthly, every three months or yearly. An exemplary treatment regimen entails administration once per week, once every two weeks, once every three weeks, once every four weeks, once a month, once every three months or once every three to six months. Typical dosage regimens for a 4-1BB antibody include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks.

The present disclosure is further illustrated by the following examples which should not be construed as further limiting. The contents of all figures and all references, patents and published patent applications cited throughout this disclosure are expressly incorporated herein by reference in their entirety.

EXAMPLES

Example 1

Generation of Fab Fragments that Bind to 4-1BB

Certain antibodies provided by the present invention were originally generated from Fabs that bind to human 4-1BB. The Fabs were selected from a phage display library, the MorphoSys HuCAL GOLD® phagemid library, following alternating panning on 4-1BB FC and cells expressing human 4-1BB. These Fabs include those that are designated as "Fab-6032," "Fab-7361," "Fab-7480," and "Fab-7483." 4-1BB antibodies MOR-6032, MOR-7361, MOR-7480, and MOR-7483 disclosed in this application were generated from "Fab-6032," "Fab-7361," "Fab-7480," and "Fab-7483, respectively. The amino acid sequence of the light chain variable region and heavy chain variable region of a given Fab are identical to the amino acid sequence of the light chain variable region and heavy chain variable region, respectively, of an illustrative antibody the designation of which shares the same numerical number with the designation of the Fab. For example, Fab-7480 and antibody MOR-7480 have identical amino acid sequences for their light chain variable region and heavy chain variable region, respectively.

The phagemid library is based on the HuCAL® concept (Knappik et al., 2000, J. Mol. Biol. 296(1):57-86) and employs the CysDisplay™ technology for displaying the Fab on the phage surface (Löhning, WO 01/05950). HuCAL GOLD® provides the option of performing selections with six single sub-libraries each comprising one VH (VH1, VH2, VH3, VH4, VH5, VH6) master gene combined with all seven VL master genes or performing selections using combined phage pools. Phage for the 1st round of pannings were prepared by Hyperphage (M13KO7ΔpIII, obtained from Progen, Heidelberg, Germany). HuCAL GOLD® is described in detail in Christine Rothe, et. al, *J. Mol. Biol.* (2008) 376, 1182-1200.

Solid phase panning was performed using recombinant human 4-1BB-Fc (R&D Systems, Cat. No. 838-4B; Minneapolis, Minn.).

Example 2

Characterizations of Fabs

The characterizations of the four Fabs described in example 1 were determined in the assays described below using the monovalent Fab-format comprising a Fab having a Flag/His-Tag.

2A. Affinity Determined with Solution Equilibrium Titration (SET) Method

The affinity (as expressed as $K_D$) of the four Fabs was determined using the SET method using an instrumentation from Meso Scale Discovery ("MSD"). Monomer fractions of antibody protein were used (at least 90% monomer content, analyzed by analytical SEC; Superdex75 (Amersham Pharmacia) for Fab, or Tosoh G3000SWXL (Tosoh Bioscience) for IgG, respectively).

Affinity determination in solution was basically performed as described in the literature (Friguet et al. 1985). In order to improve the sensitivity and accuracy of the SET method, it was transferred from classical ELISA to ECL based technology (Haenel et al. 2005).

1 mg/ml goat-anti-human $(Fab)_2$ fragment specific antibodies (Dianova) were labeled with MSD Sulfo-TAG™ NHS-Ester (Meso Scale Discovery, Gaithersburg, Md., USA) according to manufacturer's instructions.

The experiments were carried out in polypropylene microtiter plates and PBS pH 7.4 with 0.5% BSA and 0.02% Tween 20 as assay buffer. Unlabeled human 4-1BB was diluted in a 2" series, starting with a concentration at least 10 times higher than the expected $K_D$. Wells without antigen were used to determine $B_{max}$ values; wells with assay buffer were used to determine background. After addition of, e.g., 30 pM Fab (final concentration in 60 μL final volume), the mixture was incubated overnight at room temperature. The Fab concentration applied was similar to or below the expected $K_D$.

Standard MSD plates were coated with 0.05 μg/ml human 4-1BB in PBS (30 μL/well), incubated overnight, and blocked with 3% BSA in PBS for 1 hour. After washing the plate with assay buffer, the equilibrated samples were transferred to those plates (30 μL per well) and incubated for 20 minutes. After washing, 30 μL/well of the MSD Sulfo-tag labeled detection antibody (goat anti-human $(Fab)_2$) in a final dilution of 1:1500 was added to the MSD plate and incubated for 30 min on an Eppendorf shaker (700 rpm).

After washing the plate and adding 30 μL/well MSD Read Buffer T with surfactant, electrochemiluminescence signals were detected using a Sector Imager 6000 (Meso Scale Discovery, Gaithersburg, Md., USA).

The data were evaluated with XLfit (IDBS) software applying customized fitting models. For $K_D$ determination of Fab molecules the following fit model was used (Haenel et al., 2005) and modified according to Abraham et al. (1996, J. Molec. Recog. 9(5-6):456-461):

$$y = B_{max} - \left( \frac{B_{max}}{2[Fab]_t} \left( [Fab]_t + x + K_D - \sqrt{([Fab]_t + x + K_D)^2 - 4x[Fab]_t} \right) \right)$$

$[Fab]_t$: Applied total Fab concentration
x: Applied total soluble antigen concentration (binding sites)
$B_{max}$: Maximal signal of Fab without antigen
$K_D$: Affinity
Results are presented in Table 3.

2B. Biacore $K_D$ Determination on Directly Coated Antigen

For $K_D$ determination, monomeric Fab fractions (at least 90% monomer content, analyzed by analytical SEC; Superdex75, Amersham Pharmacia) were used as analyte. Binding to immobilized antigen was analyzed using a BIAcore3000 instrument (Biacore, Sweden).

The kinetic rate constants $k_{on}$ and $k_{off}$ were determined with serial dilutions of the respective Fab binding to covalently immobilized antigen CD137/HUMAN 4-1BB using the Biacore 3000 instrument (Biacore, Uppsala, Sweden). For covalent antigen immobilization standard EDC-NHS amine coupling chemistry was used. Kinetic measurements were done in HBS-EP (10 mM HEPES; pH 7.4; 150 mM NaCl; 3 mM EDTA; Tween20 0.005%) at a flow rate of 20 μl/minute using Fab concentrations ranging from about 16 to 500 nM. The injection time for each concentration was 1 minute, followed by at least 3 minutes dissociation phase. For regeneration, one or more 5 μl injections of Glycine/HCl pH2 were used.

For $K_D$ estimation of whole IgG molecules, IgGs were injected as samples on a F1 sensor chip with a low density of covalently immobilized human 4-1BB (approx. 130 RU) using a 2" serial dilution with concentrations ranging from 16 to 500 nM. Sensorgrams were evaluated using a bivalent fit model a qualitatively compared to rank the corresponding $K_D$ values.

All sensorgrams were fitted using BIA evaluation software 3.1 (Biacore). Results are presented in Table 3.

2C. Binding of Fabs in ELISA Assay

The binding of the four Fabs were determined using standard ELISA techniques on directly coated human 4-1BB/Fc. Results are presented in Table 3.

2D. Binding of Fabs in FACS Assay

The binding of the four Fabs was determined using standard FACS assay techniques on HEK293 cells stably transfected and expressing human 4-1BB as well as 300.19 (murine B-cell line) negative control cells. The results are presented in Table 3.

TABLE 3

Binding Properties of Fabs

| Fab | BIAcore Affinity $K_D$ [nM] | SET Affinity $K_D$ [pM] | ELISA Assay EC50 [nM] | FACS Assay EC50 [nM] |
|---|---|---|---|---|
| Fab-6032 | 66 | Not measured | 1.0 | 270 |
| Fab-7361 | 118 | Not measured | 0.6 | 105 |
| Fab-7480 | 0.5 | 46 | 0.7 | 0.9 |
| Fab-7483 | 0.7 | 43 | 0.6 | 8.9 |

Example 3

Characterization of IgGs

Several Fabs obtained from the panning as described herein, including Fab-6032, Fab-7361, Fab-7480, and Fab-7483, were selected for conversion into full length antibodies in IgG1 and IgG4 formats for further characterizations as described in this example. The four illustrative antibodies identified in this example, ie., MOR-6032, MOR-7361, MOR-7480, and MOR-7483, were converted from Fab-6032, Fab-7361, Fab-7480, and Fab-7483, respectively. The antibodies in IgG format were expressed and purified, and then characterized in ELISA, FACS, and luciferase reporter gene assays.

3A. Conversion to IgG

In order to express full length IgG, variable domain fragments of heavy (VH) and light chains (VL) were subcloned from Fab expression vectors into appropriate pMorph®_hIgG vectors for human IgG1 and human IgG4.

3B. Transient Expression and Purification of Human IgG

Transient expression of full length human IgG was performed in HKB11 cells, which were transfected with IgG heavy and light chain expression vectors at a 1:1 ratio. Cell culture supernatant was harvested after transfection and upscaled to 3-fold transfection volume, respectively. Supernatant was cleared by centrifugation and filtration, and then subjected to standard protein A affinity chromatography (MabSelect SURE, GE Healthcare). Proteins were eluted and neutralized. Further downstream processing involved buffer exchange and sterile filtration. Protein concentrations were determined by UV-spectrophotometry. Purity of IgG was analyzed under denaturing, reducing and denaturing, non-reducing conditions in SDS-PAGE or by using Agilent Bio-Analyzer. HP-SEC was performed to analyze IgG preparations in native state.

3C. Characterization of IgGs in ELISA Assay

IgGs were used for ELISA binding characterization on human 4-1BB/Fc and mouse 4-1BB/Fc in a direct coated setup. Table 4 below sets out the ELISA binding results for antibodies MOR-6032, MOR-7361, MOR-7480, and MOR-7483, all in IgG1 format.

TABLE 4

Binding of IgG1s in ELISA Assay

| Antibody | Human 4-1BB/Fc $EC_{50}$ [nM] | Mouse 4-1BB/Fc |
|---|---|---|
| MOR-6032 | 0.2 | − |
| MOR-7361 | 0.3 | − |
| MOR-7480 | 0.7 | (+) |
| MOR-7483 | 0.9 | − |

3D. Binding Selectivity of Antibodies (FACS Assay)

The selectivity of antibodies for 4-1BB was assessed against extracellular domain protein of 4-1BB and other members of the TNFR superfamily. These receptors included CD40 (TNFRSF5) and OX-40 (CD134, TNFRSF4). IgGs were used for FACS binding characterization on negative control HEK293 cells, as well as HEK293T-h4-1BB cells stably transfected and expressing human 4-1BB, and 300.19 stably transfected cells expressing OX-40, and 300.19 cells stably transfected and expressing CD40. The FACS binding results for antibodies MOR-6032, MOR-7361, MOR-7480, and MOR-7483, all in IgG1 format, are presented in Table 5. No significant binding to OX-40 or CD40 was observed at concentrations up to 1000 nM, demonstrating that the antibodies are at least 100-fold more selective for 4-1BB versus other related family members tested.

TABLE 5

Binding Selectivity of Antibodies (IgG1) in FACS Assay

| Antibody | HEK293T 4-1BB $EC_{50}$ [nM] | parental HEK293 | 300.19 OX-40 | 300.19 CD40 | 300.19 parental |
|---|---|---|---|---|---|
| MOR-6032 | 0.6 | − | − | − | − |
| MOR-7361 | 0.8 | − | − | − | − |
| MOR-7480 | 0.6 | − | − | − | − |
| MOR-7483 | 0.5 | (+) | − | − | − |

3E. Characterization of IgGs in Luciferase Reporter Gene Assay

IgGs were also characterized for binding in a luciferase reporter gene assay using HEK293T-h4-1BB cells in a plate bound assay, a soluble binding assay, and cross-linked binding assay. Table 6 sets out the results of the luciferase reporter gene assay for antibodies MOR-6032, MOR-7361, MOR-7480, and MOR-7483, all in IgG1 format.

TABLE 6

Characterization of IgG1 in Luciferase Reporter Gene Assay
Luciferase reporter gene assay of IgGs

| Antibody | plate-bound | soluble | cross-linked |
|---|---|---|---|
| MOR-6032 | +++ | − | +++ |
| MOR-7361 | + | − | +++ |
| MOR-7480 | + | − | +++ |
| MOR-7483 | + | − | +++ |

Example 4

Structural Characterization of Antibodies MOR-6032, MOR-7361, MOR-7480, and MOR-7483

The procedures described above in Examples 1-3 were used to produce several fully human anti-4-1BB IgG2 antibodies, including antibodies designated as "MOR-6032", "MOR-7361", "MOR-7480", and "MOR-7483." The cDNA sequences encoding the heavy and light chain variable regions of the MOR-6032, MOR-7361, MOR-7480, and MOR-7483 monoclonal antibodies were obtained using standard PCR techniques and were sequenced using standard DNA sequencing techniques.

The nucleotide and amino acid sequences of the heavy chain variable region, full length heavy chain of the IgG2 subclass, light chain variable region, and full length light chain of antibodies MOR-6032, MOR-7361, MOR-7480, MOR-7480.1, MOR-7480.2, MOR-7483, MOR-7483.1, and MOR-7483.2 are provided in this disclosure; an index of the SEQ ID NOs for these sequences is provided in Table 1.

Comparison of the MOR-6032 heavy chain immunoglobulin sequence to the known human germline immunoglobulin heavy chain sequences demonstrated that the MOR-6032 heavy chain utilizes a $V_H$ segment from human germline $V_H$ 1-69, a D segment from the human germline 4-23, and a JH segment from human germline JH 4a.

Further analysis of the MOR-6032 $V_H$ sequence using the Kabat system of CDR region determination led to the delineation of the H-CDR1, H-CDR2 and H-CDR3 regions as shown in SEQ ID NOs: 1, 2 and 3, respectively.

Comparison of the MOR-7361 heavy chain immunoglobulin sequence to the known human germline immunoglobulin heavy chain sequences demonstrated that the 7361 heavy chain utilizes a $V_H$ segment from human germline $V_H$ 3-23, a D segment from the human germline 2-8, and a JH segment from human germline JH 4a.

Further analysis of the MOR-7361 $V_H$ sequence using the Kabat system of CDR region determination led to the delineation of the heavy chain H-CDR1, H-CDR2 and H-CDR3 regions as shown in SEQ ID NOs: 15, 16 and 17, respectively.

Comparison of the MOR-7480 and MOR-7483 heavy chain immunoglobulin sequences to the known human germline immunoglobulin heavy chain sequences demonstrated that the 7480 and 7483 heavy chains utilize a $V_H$ segment from human germline $V_H$ 5, a D segment from the human germline 5-18, and a JH segment from human germline JH 4a.

Further analysis of the 7480 and 7483 $V_H$ sequences using the Kabat system of CDR region determination led to the delineation of the H-CDR1, H-CDR2 and H-CDR3 regions as shown in SEQ ID NOs: 29, 30 and 31, respectively.

Comparison of the MOR-6032, MOR-7361, MOR-7480 and MOR-7483 light chain immunoglobulin sequences to the known human germline immunoglobulin light chain sequences demonstrated that the 6032, 7361, 7480 and 7483 light chains all utilize a $V_L$ segment from human germline λ3-r and a JL segment from human germline JL 3b.

Further analysis of the MOR-6032 $V_L$ sequence using the Kabat system of CDR region determination led to the delineation of the light chain CDR1, CDR2 and CDR3 regions as shown in SEQ ID NOs: 6, 7, and 8, respectively.

Further analysis of the MOR-7361 $V_L$ sequence using the Kabat system of CDR region determination led to the delineation of the L-CDR1, L-CDR2 and L-CDR3 regions as shown in SEQ ID NOs: 20, 21, and 22, respectively.

Further analysis of the MOR-7480 $V_L$ sequence using the Kabat system of CDR region determination led to the delineation of the L-CDR1, L-CDR2 and L-CDR3 regions as shown in SEQ ID NOs: 34, 35, and 36, respectively.

Further analysis of the MOR-7483 $V_L$ sequence using the Kabat system of CDR region determination led to the delineation of the L-CDR1, L-CDR2 and L-CDR3 regions as shown in SEQ ID NOs: 34, 35, and 55, respectively.

Example 5

Germlined Versions of Antibodies MOR-7480 and MOR-7483

In order to minimize immunogenicity of the MOR-7480 and MOR-7483 antibodies, several amino acid residues were mutated back to germline sequence, as follows. A germlined version of MOR-7480, designated MOR-7480.1, was prepared by returning two amino acids in the FR1 region of the heavy variable chain to germline sequence. More specifically, Q at amino acid residue number 1 was returned to the germline E, and K at amino acid residue number 19 was returned to R. The two amino acid residues that were changed in the heavy chain variable region can be seen by comparing the amino acid sequence of MOR-7480 (SEQ ID NO:32) with MOR-7480.1 (SEQ ID NO:43). In the light chain variable region of MOR-7480, five amino acids in the FR1 region (D1S, I2Y, A13S, R19S, S21T), two amino acids in the FR2 region (A42S, V45L), and one in the FR3 region (E80M) were reverted to germline sequence. The eight amino acids that were changed in the light chain variable region can be seen by comparing the amino acid sequence of MOR-7480 (SEQ ID NO:37) with that of MOR-7480.1 (SEQ ID NO:45).

Moreover, a third version of MOR-7480 was prepared by starting with the light chain variable region sequence of MOR-7480.1 (SEQ ID NO:45) and reverting L45 back to V to produce MOR-7480.2 (SEQ ID NO:51).

A "germlined" version of MOR-7483, designated MOR-7483.1, was prepared by backmutating two amino acids in the FR1 region of the heavy variable chain to germline sequence. The germlined versions can be prepared by starting with the germline version of the antibody chain and then changing the desired amino acids in the CDRs, or any combination of mutations starting from any version. To produce MOR-7483.1, Q at amino acid residue number 1 was returned to the germline E, and K at amino acid residue number 19 was returned to R. The two amino acid residues that were changed in the heavy chain variable region can be seen by comparing the sequence of MOR-7483 (SEQ ID NO:32) with MOR-7483.1 (SEQ ID NO:43). In the light chain variable region of MOR-7483, five amino acids in the FR1 region (D1S, I2Y, A13S, R19S, S21T), two amino acids in the FR2 region (A42S, V45L), and one in the FR3 region (E80M) were reverted to germline sequence. The eight amino acids that were changed in the light chain variable region can be seen by comparing the amino acid sequence of MOR-7483 (SEQ ID NO:56) with that of MOR-7483.1 (SEQ ID NO:60).

Moreover, a third version of MOR-7483 was prepared by back mutating L45 of the light chain variable region sequence of MOR-7483.1 (SEQ ID NO:60) to the germline V45 to produce MOR-7483.2 (SEQ ID NO:64).

Example 6

In Vitro Properties of Antibodies, Including Germlined Versions

Binding Affinities of Antibodies (BIAcore Assay)
Binding kinetics of certain antibodies binding human 4-1BB were measured by surface plasmon resonance (SPR) technology using a Biacore 3000 instrument (GE Healthcare). Recombinant human 4-1BB/Fc Chimera protein comprising amino acids 24-186 of SEQ ID NO: 68 was purchased from R&D Systems Inc. (#838-4B). The lyophilized protein was dissolved in a buffer containing 150 mM NaCl, 25 mM HEPES pH 8.0, 6 mM $MgCl_2$, 0.005% polysorbate 20, and 0.5 mM sodium azide to a final concentration of 80 nM based on the predicted molecular weight (44.8 kDa) provided by the R&D Systems. The Fc portion of the molecule was cleaved by treatment with Bovine Factor Xa (Pierce, #32521) in 150 mM NaCl, 25 mM HEPES pH 8.0, 6 mM $MgCl_2$, 0.005% polysorbate 20, 0.5 mM sodium azide, using a 20 hour incubation at 22° C. with a 3% Factor Xa (3 μg Factor Xa per 100 μg 4-1BB chimera). The 4-1BB portion of the molecule comprises amino acid residues 24 though 186 of the human 4-1BB protein. Binding experiments were carried out at 25° C. in a running buffer comprising 150 mM NaCl, 25 mM HEPES pH 8.0, 6 mM $MgCl_2$, 0.005% polysorbate 20, and 0.5 mM sodium azide. Antibodies were immobilized by standard amine coupling to a CM5 sensorchip (GE Healthcare) using a 0.1 mg/mL solution of the antibody in 10 mM sodium acetate at pH 5.0. The 4-1BB was injected at a range of concentrations from 80 nM to 0.16 nM, at a 50 μL/minute flow rate, for 3.6 minutes followed by a 26 minute dissociation period using the Kinject feature of the Biacore 3000 instrument. The bound complex was regenerated by a 1 minute pulse of 10 mM phosphoric acid in water. Data analysis was performed using the Scrubber2 software (BioLogic Software). Sensograms were fit to a simple 1:1 Langmuir binding model. The antibodies were shown to reversibly bind to recombinant human 4-1BB. The results (average values) are presented in Table 7.

Binding to the Extracellular Domain of 4-1BB (ELISA Assay)

Human 4-1BB IgG1Fc chimera (R&D Systems, Minneapolis, Minn.) was resuspended with Dulbecco's Phosphate Buffered Saline (DPBS) containing 0.1% bovine serum albumin (BSA) to 0.2 mg/ml and diluted with DPBS to a final concentration of 0.03 ug/ml. Nunc-Immuno Maxisorp 96 well plates were coated with 0.1 ml per well of the recombinant 4-1BB chimera leaving empty wells for nonspecific binding controls and incubated at 4° C. overnight. The 4-1BB solution was removed and the plates were washed three times with 0.2 ml wash buffer (0.05% Tween-20 in DPBS). 0.2 ml blocking buffer (5% BSA, 0.05% Tween-20 in DPBS) was added to all wells and incubated at 4° C. for 1 hour with mixing. The blocking buffer was removed and plates washed three times with 0.2 ml wash buffer. Serial dilutions of the 4-1BB test antibodies were prepared in DPBS and 0.1 ml diluted Ab was added per well. Plates were incubated 1.5 hour at room temperature. Antibody solution was removed and the plates washed three times with 0.2 ml wash buffer per well. Horseradish peroxidase labeled goat anti-human IgG, F(ab')2 specific F(ab')2 antibody (Jackson Immunoresearch #109-036-097, West Grove, Pa.) was diluted 1:5000 with DPBS and added 0.1 ml per well. The plates were incubated 1 hour at room temperature and washed with 0.2 ml per well wash buffer. 0.1 ml SureBlue TMB microwell peroxidase substrate (Kirkegaard & Perry Labs, Gaithersburg, Md.) was added and incubated for 20 minutes at room temperature. The reaction was stopped by adding an equal volume of 2M $H_2SO_4$ and absorbance was read at 450 nm on a Molecular Devices Spectra Max 340 (Molecular Devices, Sunnyvale, Calif.). The results are presented in Table 8.

Ligand Competition Binding (ELISA Assay)

Antibodies were tested for their ability to block the binding of the human 4-1BB_IgG1Fc chimera to plate bound recombinant 4-1BB ligand (4-1BBL). Recombinant human 4-1BB ligand (Biosource/Invitrogen, Carlsbad, Calif.) was resuspended to 0.2 mg/mL in DPBS+0.1% bovine serum albumin and then diluted to 1 μg/mL in DPBS. Nunc-Immuno MaxiSorp surface 96 well plates were coated with 0.1 mL/well of the 4-1BBL solution overnight at 4° C. The following day the 4-1BBL solution was removed and 0.2 mL Blocking buffer (1% bovine serum albumin, 0.05% Tween-20 in DPBS) added and incubated at room temperature for 2 hours. During the blocking step the antibody stocks were diluted in a range from 8 ng/mL to 6 μg/mL in DPBS. Recombinant human 4-1BB_IgG1Fc (R&D Systems, Minneapolis, Minn.) was resuspended to 0.2 mg/mL in DPBS+0.1% bovine serum albumin and then diluted to 0.02 μg/mL in DPBS. The blocked 4-1 BBL coated plates were washed three times with 0.2 mL wash buffer (0.05% Tween 20 in DPBS). 60 μL antibody dilutions were added along with 60 μL 4-1BB_IgG1 Fc chimera and incubated at room temperature for 1.5 hours. Plates were washed as described previously. Horseradish peroxidase anti-6xHistidine tag antibody (R&D Systems, Minneapolis Minn. #MAB050H) was diluted 1:1000 in DPBS, 50 μL of the resulting solution added to the wells of the washed plates, and incubated at room temperature for 1 hour. Plates were washed as previously described, 50 μL TMB substrate solution was added to each well and incubated at room temperature for 20 minutes. The reaction was stopped with 50 μL 0.2N $H_2SO_4$ and absorbance at 450 nm read using a Molecular Devices plate reader. The results are presented in Table 8.

Species Cross-Reactivity of Antibodies

The species-cross reactivity of the exemplary antibodies was measured using phytohemagglutinin (PHA) stimulated primary peripheral blood mononuclear cells (PBMC) of human, cynomolgus monkey (cyno), dog, and rat. Cells were isolated according to the procedure described below. Cells (~$5.0 \times 10^5$ cells/tube) were washed once in cold wash buffer (PBS, 2% FBS and 0.02% sodium azide) and 100 μl/tube of Alexa Fluor 647 conjugated control or 4-1BB reactive antibodies at 15.5 μg/mL (100 nM) was added to each sample along with labeled species specific T cell marker antibodies. The T cell marker antibodies utilized are as follows, FITC anti-human CD3e (BD Pharmingen, #555332), FITC anti-rat CD3e (BD Pharmingen, #559975), FITC anti-rabbit CD4+ FITC anti-rabbit CD8 (AbD Serotec, #MCA799F and #MCA1576F), FITC anti-dog CD3e (AbD Serotec, #MCA1774F), and PerCP anti-human/cyno CD3e (BD Pharmingen, #552851). The cells were incubated in the dark with fluorochrome antibodies on ice for 30 minutes, washed three times and resuspended in 0.3 ml wash buffer for analysis. Antibody staining was measured and analyzed using a Becton Dickinson FACS Calibur and FlowJo 8.8.2 software.

Isolation of Human T Lymphocytes.

Human whole blood was collected into syringes containing 1 mL 0.5M EDTA and then transferred to Sigma Accuspin tubes (Sigma, St. Louis, Mo.) for the isolation of peripheral blood mononuclear cells (PBMC) as described by the manufacturer. The PBMCs were washed twice with DPBS containing 5 mM EDTA and T lymphocytes were isolated using a T cell purification column as described by the manufacturer (R&D Systems, Minneapolis, Minn.). Briefly, PBMCs were resuspended in 2 mL of column buffer and loaded into a pre-washed T cell isolation column. PBMCs were incubated for 10 minutes at room temperature and T cells were eluted with column buffer, washed one time and resuspended TCM at $2 \times 10^6$ cells/mL consisting of RPMI 1640 (Sigma, St Louis, Mo.) supplemented with 10% fetal bovine serum (Sigma, St. Louis, Mo.) and L-glutamine (2 mM), Hepes (10 mM), penicillin (100 U/ml), streptomycin (50 ug/ml) (Gibco, Grand Island, N.Y.).

Isolation of Cynomolgus PBMCs.

Cynomolgus whole blood (Bioreclamation; Hicksville, N.Y.) was collected in sodium citrate CPT vacutainer tubes (BD; Franklin Lakes, N.J.) and then spun at 1500×g for 20 minutes at room temperature. Tubes were shipped overnight at 4° C. The PBMC fraction was collected from the CPT tubes and washed 2× with PBS containing 5 mM EDTA. Following the wash step, PBMCs were counted and readjusted to $2\times10^6$ cells/mL in tissue culture medium (TCM). TCM consisted of RPMI 1640 (Sigma, St Louis, Mo.) supplemented with 10% fetal bovine serum (Sigma, St Louis, Mo.) and L-glutamine (2 mM), HEPES (10 mM), penicillin (100 U/mL), streptomycin (50 μg/mL) purchased from Gibco (Grand Island, N.Y.). Cells were stimulated with 10 μg/mL PHA 2-3 days to induce expression of 4-1BB.

Isolation of Canine PBMCs.

Canine whole blood was drawn into heparinized vacutainer tubes (BD; Franklin Lakes, N.J.) and diluted 1:2 with PBS containing 5 mM EDTA. After mixing, 4 mL of the diluted blood was carefully layered over 3 mL Lympholyte-Mammal (Cedarlane Laboratories, Westbury, N.Y.) and centrifuged 800×g for 20 minutes at 25° C. The PBMC interface was collected, washed twice with PBS and resuspended to $2\times10^6$ cells/mL in TCM containing PHA at 10 μg/mL (Remel, Lenexa, Kans.). The cells were cultured for 48-72 hours prior to testing for antibody binding by flow cytometry.

Isolation of Rat PBMCs.

Rat whole blood was drawn into heparinized vacutainer tubes (BD; Franklin Lakes, N.J.) and diluted 1:3 with PBS containing 5 mM EDTA. After mixing, 6 mL of the diluted blood was carefully layered over 4.5 ml Lympholyte-Mammal (Cedarlane Laboratories, Westbury, N.Y.) and centrifuged 800×g for 20 minutes at 25° C. The PBMC interface was collected, washed twice with PBS and resuspended to $2\times10^6$ cells/mL in TCM containing PHA at 10 μg/mL (Remel, Lenexa, Kans.). The cells were cultured for 48-72 hours prior to testing for antibody binding by flow cytometry.

The binding results are provided in FIG. 1. The antibodies were found to bind to the human and cyno 4-1BB with high affinity, while binding to dog and rat 4-1BB was not observed at concentrations of 100 nM, the highest concentration tested.

TABLE 7

Binding Affinities of IgG Antibodies (Biacore)

| Antibody | $k_a$ (M$^{-1}$ s$^{-1}$) | $k_d$ (s$^{-1}$) | $K_D$ (nM) | $t_{1/2}$ |
|---|---|---|---|---|
| MOR7480 (IgG1) | $3.6 \times 10^5$ | $1.5 \times 10^{-4}$ | 0.42 | 82 min |
| MOR7480 (IgG2) | $4.5 \times 10^5$ | $2.3 \times 10^{-4}$ | 0.57 | 50 min |
| MOR-7480.1 (IgG1) | $1.2 \pm 0.3 \times 10^6$ | $9.8 \pm 0.15 \times 10^{-3}$ | $8.4 \pm 1.4$ | 1.2 min |
| MOR-7480.1 (IgG2) | $1.4 \pm 0.06 \times 10^6$ | $1.2 \pm 0.1 \times 10^{-2}$ | $8.7 \pm 1.0$ | 1.0 min |
| MOR-7480.2 (IgG1) | $9.3 \times 10^5$ | $4.1 \times 10^{-4}$ | 0.4 | 28 min |
| MOR-7483 (IgG1) | $6.0 \times 10^5$ | $4.4 \times 10^{-4}$ | 0.73 | 26 min |
| MOR-7483 (IgG2) | $3.0 \times 10^5$ | $3.8 \times 10^{-4}$ | 1.3 | 1.3 min |
| MOR-7483.1 (IgG1) | $8.0 \times 10^5$ | 0.022 | 28 | 32 min |

TABLE 8

ELISA Binding and Ligand Competition Values

| | | Binding ELISA | Ligand Competition ELISA | |
|---|---|---|---|---|
| Antibody | Isotype | EC50 ± STD (nM) | % max inhibition | IC50 ± STD (nM) |
| MOR-6032 | IgG1 | 0.071 ± 0.029 | 100 ± 2 | 0.153 ± 0.067 |
| MOR-6032 | IgG4 | 0.226 ± 0.161 | 100 ± 2 | 0.112 ± 0.023 |
| MOR-7361 | IgG1 | 0.091 ± 0.010 | 100 ± 2 | 0.172 ± 0.006 |
| MOR-7480 | IgG1 | 0.076 ± 0.008 | 96 ± 2 | 0.122 ± 0.019 |
| MOR-7480 | IgG2 | 0.122 ± 0.009 | 98 ± 2 | 0.125 ± 0.003 |
| MOR-7483 | IgG1 | 0.073 ± 0.024 | 98 ± 2 | 0.109 ± 0.028 |
| MOR-7483 | IgG2 | 0.165 ± 0.035 | 97 ± 2 | 0.138 ± 0.015 |

Epitope Mapping

In order to determine the epitope binding region of the 4-1BB agonist antibodies, a series of mutations (Table 9) were made to the human 4-1BB extracellular domain to the published dog 4-1BB sequence (Ref. Seq. XM_845243).

TABLE 9

Mutant of Human 4-1BB Extracellular Domain

| Mutant of human 4-1BB extracellular domain | Amino Acid Changes |
|---|---|
| Hu41BB N&E | N30K, A56T, G57S, R60K, T61A |
| Hu41BB N&E.1 | N30K, D38G, N39K, R41K, S46I, A56T, G57S, R60K, T61A |
| Hu41BB N&E.2 | N30K, A56T, G57S, R60K, T61A, K69E, R75K, E77V |
| Hu41BB N&E.3 | L24I, P27S, N42S, T89I, P90S, S100T |
| Hu41BB N&E.4 | L24I, P27S, N30K, D38G, N39K, R41K, N42S, S46I, A56T, G57S, R60K, T61A, K69E, R75K, E77V, T89I, P90S, S100T |
| Hu41BB N&E.5 | K115Q, C121R, R134Q, R154S, V156A |
| Hu41BB N&E.6 | S161A, P162S, D164G, L165F, A169T |

All human-to-dog mutations were prepared by Gene Dynamics LLC, (Portland, Oreg.) in the retroviral expression vector pMSCVpuro (Clontech Laboratories Mountain View, Calif.). Additionally the full canine cDNA sequence was prepared via gene synthesis corresponding to Ref. Seq. XM_845243.

Viral preparations were established by transient transfection of roughly 40-50% confluent 293T cells in T-75 flasks. Following culture, the viral supernatant was then sterile filtered, and subjected to concentration. The concentrated virus was collected and stored at −80° C.

Logarithmically growing 300-19 cells were transduced with retrovirus using 1:250 dilution concentrated virus plus 8 ug/ml polybrene in complete DMEM. Following a 24-hour incubation, 2 ug/ml puromycin was added to the cultures and maintained during the course of the study.

Positive expression of the 4-1BB receptors by the puromycin selected pools was confirmed by staining with 1 ug/ml polyclonal goat anti-human 4-1BB antibody (R&D Systems Inc.) plus 1:200 dilution PE labeled donkey anti-goat IgG (H+L) F(ab')$_2$ (Jackson Immunoresearch Inc.). In order to determine recognition of the mutant 4-1BB receptors by the test antibodies the puromycin selected pools were stained with 100 nM dilution of the unlabeled primary antibody on ice for 30 min, followed by two washes with FACS buffer, and 1:200 dilution species specific PE labeled donkey anti-IgG (H+L) F(ab')₂. Cells were analyzed by FACS using a BD FACS Calibur and FlowJo 8.8.6 software.

Relative staining of each cell pool is summarized in Table 10.

TABLE 10

Relative Staining of Each Cell Pool

| Ab | h41BB | N&E | N&E.1 | N&E.2 | N&E.3 | N&E.4 | N&E.5 | N&E.6 | Dog 41BB |
|---|---|---|---|---|---|---|---|---|---|
| Goat pAb | + | + | + | + | + | + | + | + | + |
| BBK-2 | + | + | − | + | + | − | + | + | − |
| JG1.6A | + | + | − | + | + | − | + | + | − |
| 4B4-1 | + | + | − | + | + | − | + | + | − |
| 6032_G1 | + | + | + | − | + | − | + | + | − |
| 7361_G1 | + | + | + | − | +/− | − | + | + | − |
| 7480_G1 | + | + | + | + | + | + | + | + | + |
| 7480.1_G1 | + | + | + | + | + | + | − | + | − |
| 7480.1_G2 | + | + | + | + | + | + | +/− | + | − |
| 7480.2_G1 | + | + | + | + | + | + | + | + | + |
| 7483_G1 | + | + | + | + | + | + | +/− | + | +/− |
| 7483_G2 | + | + | + | + | + | + | − | + | − |

Differentiation of binding between antibodies having similar sequences (MOR-7480, MOR-7480.1, MOR-7480.2, MOR-7483, and MOR-7483.1) was discovered within the mutations of clone N&E.5, suggesting that the determinants for antibody recognition lie within the mutated region.

In order to determine the relative affinity of these antibodies for human 4-1BB extracellular domain and the mutant of human 4-1BB extracellular domain, mutant N&E.5, a dose response FACS curve was determined for each antibody. Alexa Fluor 647 labeled MOR_7480, MOR_7480.1, and MOR_7480.2 were diluted in FACS buffer from 1 uM in an 8 point 1:5 dilution series and used to stain parental 300-19, hu4-1BB, hu4-1BB N&E.5, and dog 4-1BB cell pools. The cells were analyzed by FACS using a BD FACS Calibur and FlowJo 8.8.6 software. The geometric mean fluorescence of each receptor expressing pool was normalized to staining of parental cells and expressed as fold staining and an EC50 for dose response was determined. The EC50 summary is shown in Table 11. Greater than 5 fold decrease in binding for both MOR_7480.2 and MOR_7480 for the human 4-1BB mutant N&E.5 was noted.

TABLE 11

Binding EC₅₀ (nM) of Antibodies

| Antibody (IgG1) | Human 4-1BB | 4-1BB Mutant N&E.5 |
|---|---|---|
| MOR_7480.1 | 7.916 | n/a |
| MOR_7480.2 | 0.510 | 2.730 |
| MOR_7480 | 1.68 | 12.29 |

Agonist Activity of Antibodies (Luciferase Activity Assay)

293T cells expressing human 4-1BB along with a stably integrated NFkB luciferase reporter were prepared. Cells were harvested, washed and resuspended into phenol red free complete medium (DMEM containing 10% fetal bovine serum, HEPES buffer, nonessential amino acids and L-glutamine) at density of $0.6 \times 10^6$ cells/mL. 50 μl of cells were plated into each assay well of a white 96 well plate (PerkinElmer, Waltham, Mass.). Test antibodies were added to each well in the presence 2.5:1 ratio of a cross linking antibody Fab' goat anti-human IgG Fc (Jackson ImmunoResearch, West Grove, Pa.). The plate was incubated 5 hours at 37° C. 75 μl of Bright-Glo Luciferase reagent (Promega, Madison Wis.) was added and the amount of luciferase activity was measured using a Packard TopCount NXT scintillation counter.

Figure 2:
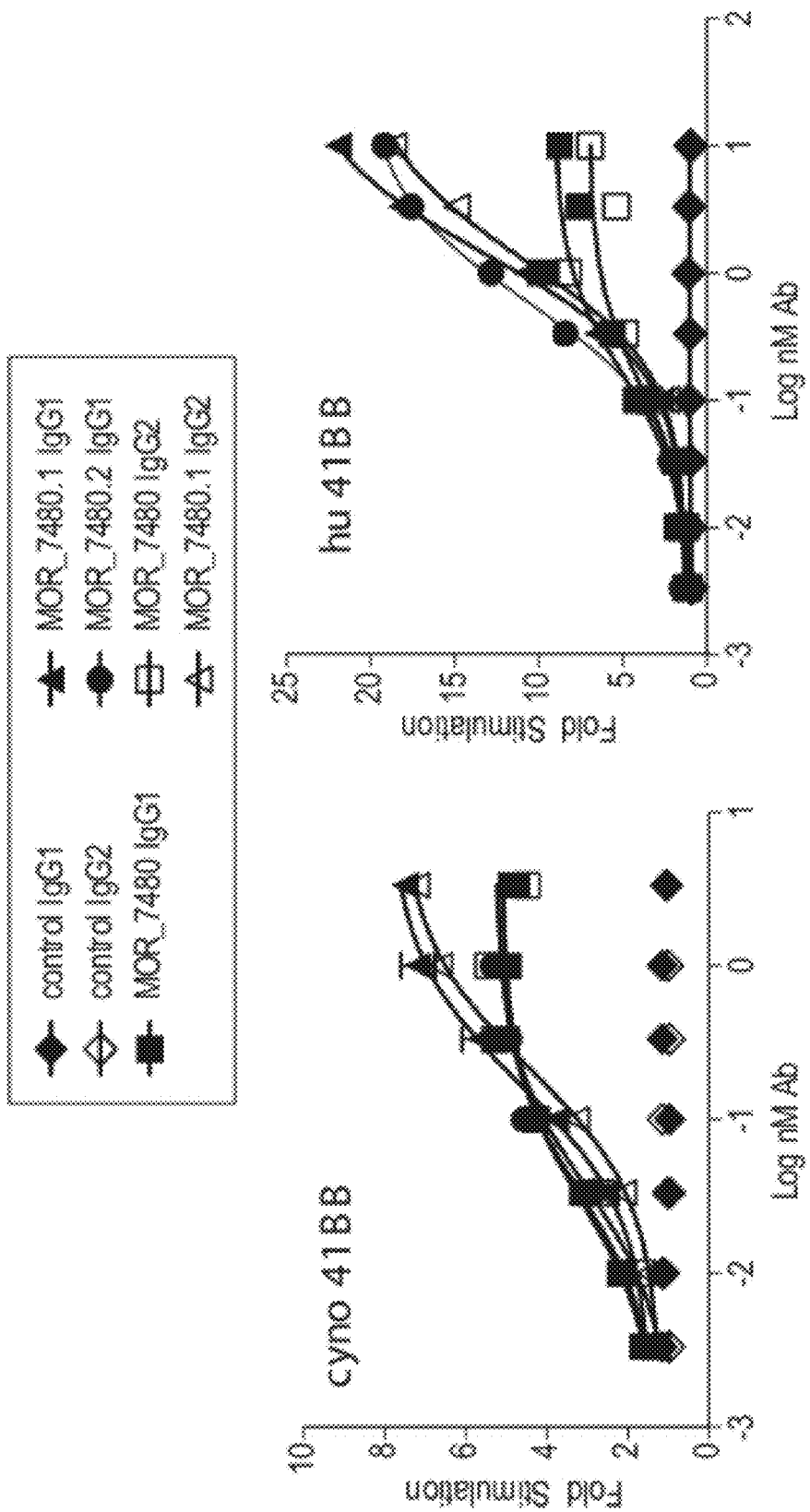
FIG. 2 is two line graphs showing luciferase reporter activity in 4-1BB expressing 293T cells that have been stimulated with several concentrations of 4-1BB specific mAb or isotype control mAb. The left panel demonstrates reporter activity in cells that express cynomolgus 4-1BB. The right panel demonstrates activity in cells that express human 4-1BB. The data is expressed as fold stimulation above isotype control.

293T cells expressing cynomologous monkey 4-1BB were prepared by viral transduction and selection of a stable pool with 2 μg/ml puromycin. Cyno 4-1BB expressing 293T cells were plated in a T-75 flask to roughly 60-70% confluency then transfected with 10 μg pLuc_6xNFkB plus 0.1 μg pRL-CMV as a transfection control. Transfections were performed using Fugene 6 transfection reagent (Roche Indianapolis, Ind.) at a 6 μl Fugene to 1 μg plasmid DNA ratio according to manufacturer instructions. Cells were harvested the following day washed and resuspended into phenol red free complete medium (DMEM containing 10% fetal bovine serum, nonessential amino acids and L-glutamine) at density of $0.6 \times 10^6$ cells/mL. 50 μl of cells were plated into each assay well of a white 96 well plate (PerkinElmer, Waltham, Mass.). Test antibodies were added to each well in the presence 2.5:1 ratio of a cross linking Fab' goat anti-human IgG Fc antibody (Jackson ImmunoResearch, West Grove, Pa.). The plate was incubated hours at 37° C. 75 μl of luciferase assay reagent was added and the amount of firefly luciferase activity was measured using a Packard TopCount NXT scintillation counter. Additionally, 75 μl of Stop & Glo reagent was added to assess the renilla luciferase activity. The amount of renilla luciferase activity was measured using a Pakcard TopCount NXT scintillation counter. Results are presented in FIG. 2.

Agonist Activity of Antibodies (Primary T Cell IL-2 Release Assay)

Figure 3A:
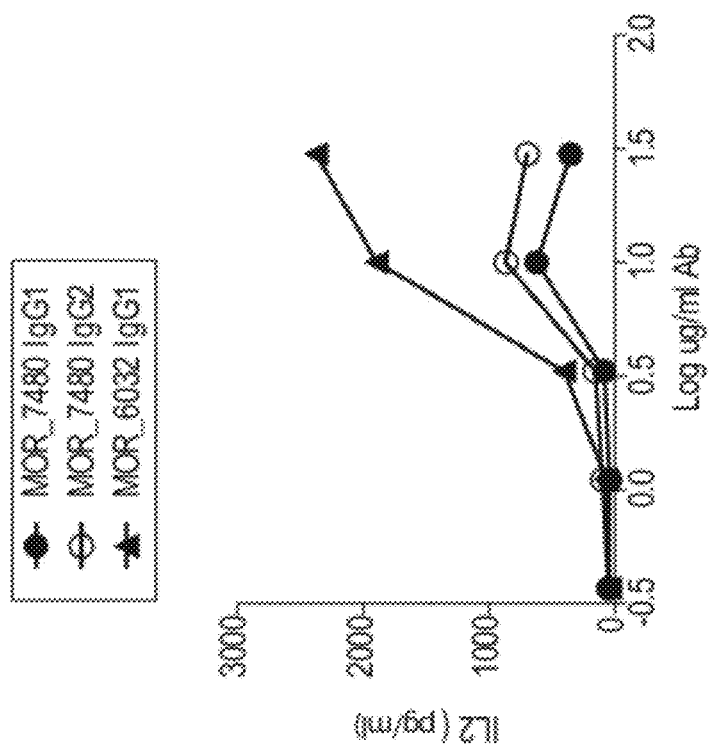
FIG. 3 (3A and 3B) are line graphs showing the concentration of human IL-2 present in cell culture media following 72 hours of stimulation of human T cells with anti-CD3 and several concentrations of 4-1BB antibodies. Each panel (A and B) represents an individual donor.
Figure 3B:
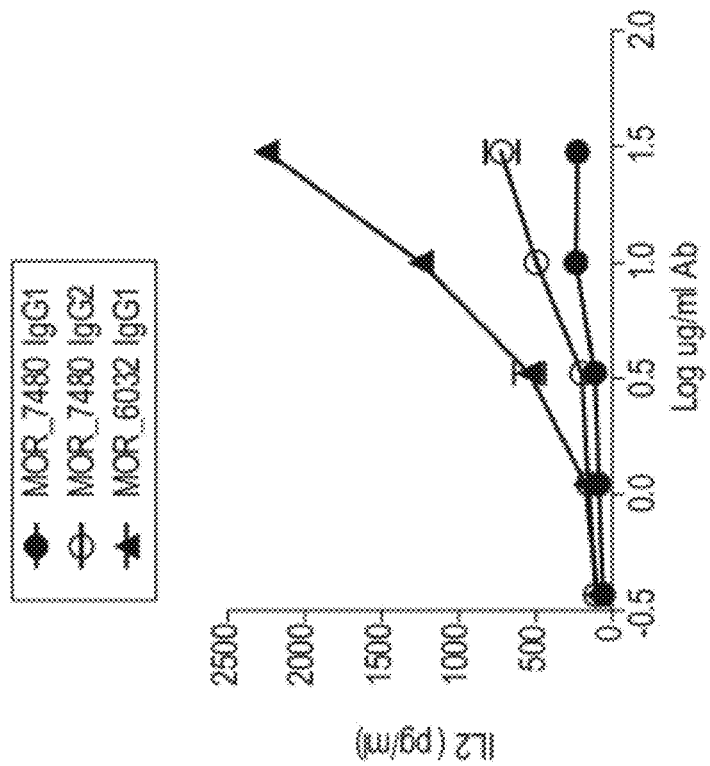

Nunc Maxisorp 96 well plates were UV sterilized prior to plate coating. Test antibodies were diluted in PBS to 60 μg/ml. 0.2 ml of the diluted Ab was divided to 2 wells of a polypropylene 96 well plate and serially diluted 1:3. 50 μl of the diluted Ab were added to the sterile Maxisorp 96 well assay plate and immediately 50 μl of 20 μg/ml anti-human CD3ε clone UCHT1 was added (Biolegend San Diego, Calif.). All plates were then incubated overnight at 4° C. The following day, Ab coated plates were washed 1× with PBS and 0.15 ml RPMI complete media was added to the wells of the Nunc Maxisorp plates. Human T cells were isolated as described previously elsewhere herein and 50 μl purified T cells at $2 \times 10^6$ cells/ml (100,000 cells/well) were added to each well. Cells were incubated at 37° C., 5% $CO_2$ for 3 days. Supernatant from each well was collected and either assayed immediately or stored at −20° C. prior to assay. Supernatants were diluted with complete media prior to IL-2 ELISA assay (R&D Systems, Minneapolis, Minn.). Results are presented in FIG. 3.

Example 7

Human Leukocyte Expansion Induced by 4-1BB Antibodies In Vivo

Figure 4:
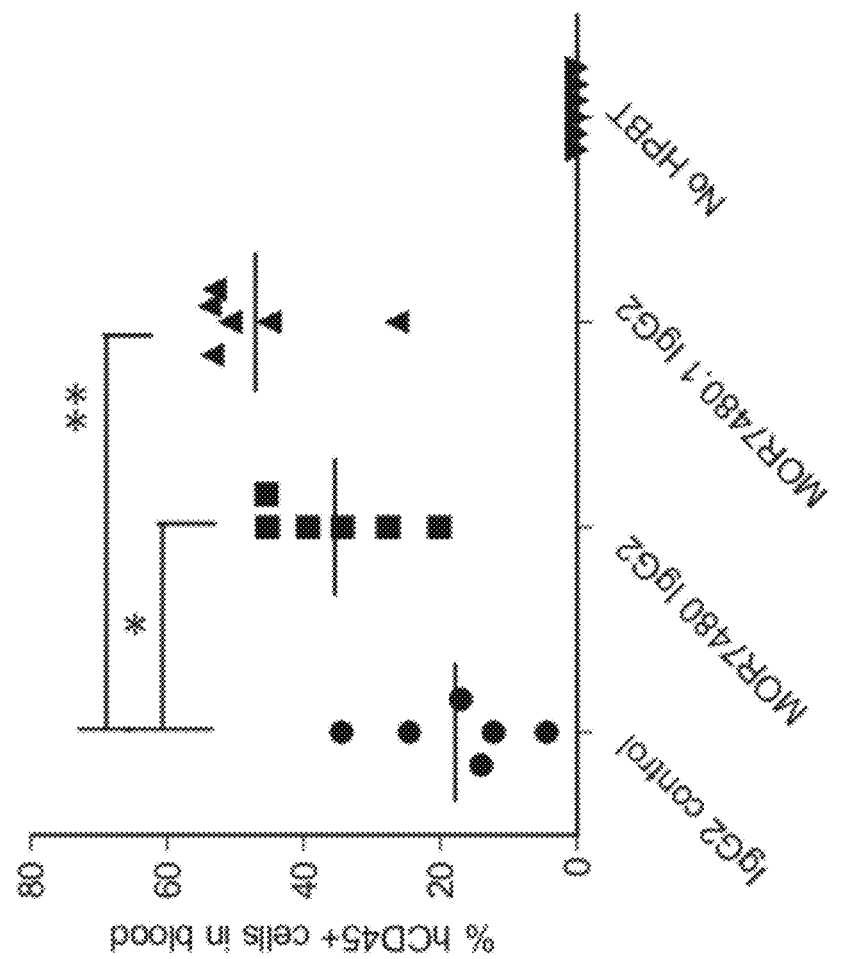
FIG. 4 is a scattergram showing the expansion of human peripheral blood mononuclear cells in mice that have been treated with 4-1BB mAb or isotype control mAb. Data is expressed as the percentage of cells expressing human CD45 in the peripheral blood of individual NSG mice on study days 24-28 that had been injected with six million human peripheral blood mononuclear cells on day 0 and injected with 1 mg/kg 4-1BB mAb or isotype control mAb on day 9. Statistical significance was determined using a two tailed Mann-Whitney test *p<0.05, **p<0.005. No HBPT refers to animals that were not injected with human cells.

The lack of detectable cross-reactivity of the 4-1BB antibodies with the murine 4-1BB and the requirement for the presence of human immune cells required the development of models for the in vivo functional assessment of the 4-1BB antibodies. Mice with the NOD genetic background carrying the severe combined immunodeficient (SCID) mutation and deficiency in the IL-2 receptor common gamma chain (commonly termed NSG) are able to support the engraftment of large number of human peripheral blood leukocytes (huPBL) and maintain engraftment for at least 30 days (King, 2008, Clin. Immunol. 126:303-314). This mouse model, also known as huPBL-NSG model, was used to assess the functional effect of in vivo systemic administration of the antibodies on human immune cells. Specifically, 6 million freshly isolated human PBMCs were adoptively transferred via intraveinous injection into NOD.Cg-Prkdc$^{scid}$ Il2rg$^{tmIwjI}$/SzJ (NSG) host mice. Nine days post PBMC injections, the animals were administered a single 1 mg/kg dose of MOR7480, MOR7480.1 or IgG2 isotype control antibody via intraperitoneal injection. At day 24 to 28 post PBMC engraftment, PBMC were stained with antibodies to human and murine CD45 assessed via flow cytometry. Forward and side scatter profiles were used to determine a lymphocyte gate. As shown in FIG. 4, MOR7480 and MOR7480.1 were able to enhance expansion of human leukocytes as evidenced by increased proportion of human CD45+ cells in the peripheral blood of engrafted mice. For each group, n≧6 mice.

Figure 5:
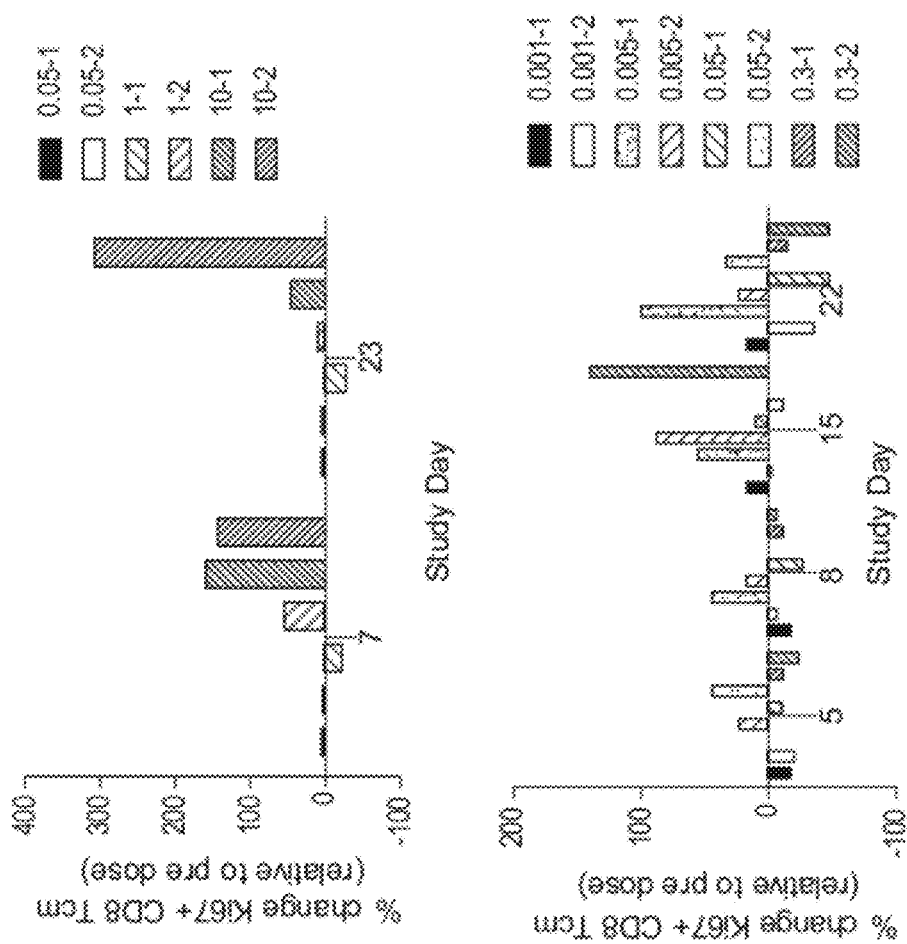
FIG. 5 is two column graphs showing the change in proliferating CD8 central memory T cells at several time points following administration of 4-1BB mAb in cynomolgus monkeys. Data is shown as columns representing individual animals designated as (dose level-animal number) and is represented as intra-animal change in the number of Ki-67+ cells relative to pre study number {[(#Ki-67+ cells on indicated study day–#Ki-67+ cells at pre dose)/#Ki-67+ cells at pre dose]*100}. CD8 central memory cells were identified as CD3+, CD8+, CD28+ and CD95+.

In addition, MOR7480.1 treatment of cynomolgus monkeys increased proliferation among cytotoxic central memory T cells (CD8 T$_{CM}$) in PBMC samples. Cynomolgus monkeys (2 animals per dose level) were given a single intravenous injection of MOR7480.1 at the indicated dose. PBMC were harvested 7 days prior to the antibody dose (pre dose) and on the indicated study days relative to administration of MOR7480.1 (on Study Day 1). PBMC were stained with antibodies for CD3, CD4, CD8, CD28, CD95, and Ki-67 and analyzed via flow cytometry. Data was collected on a Canto II (Beckton Dickinson) and analyzed using DIVA software (Becton Dickinson). CD8 central memory cells were identified as CD3+, CD8+, CD28+ and CD95+. Data is shown for individual animals designated as (dose level-animal number) and is represented as intra-animal change in the number of Ki-67+ cells relative to pre study number {[(#Ki-67+ cells on indicated study day—#Ki-67+ cells at pre dose)/#Ki-67+ cells at pre dose]*100}. As shown in FIG. 5, A 1.5 fold or greater increase in proliferating central memory T cells during the first 7-13 days of study was noted in at least one animal of all groups treated with 0.3 mg/kg or greater.

Example 8

Anti-Tumor Activity of 4-1BB Antibodies (In Vivo Model)

PC3 Human Prostate Cancer Model.

The lack of rodent cross reactivity of the 4-1BB antibodies prevented the use of standard murine syngeneic or human xenograft tumor models for the assessment of anti-human tumor efficacy of the antibodies. Accordingly, a novel huPBL-SCID-Bg xenogenic tumor mouse model was generated using a SCID-Bg mouse (CB.17/Icr.Cg Pkrdc$^{scid}$Lyst$^{bg}$/CrI), which harbors the beige (Bg) mutation lack murine T and B lymphocytes and functional NK cells. The anti-human tumor efficacy of the 4-1BB antibodies was assessed using this model as described below.

The PC3 human prostate or LOVO human colon cell line was obtained from American Type Culture Collection and was cultured in RPMI-1640 (Invitrogen) enriched with the following Invitrogen supplements: L-Glutamine, Sodium pyruvate, non-essential amino acids, penicillin/streptomycin, Hepes, and 10% heat inactivated fetal bovine serum (FBS; Cat. No. F2442, Sigma Aldrich). Cells were grown to confluency in T-225 Falcon flasks. Subsequently, cells were trypsinized (Trypsin 0.25%-EDTA; Cat. No. 2500-056, Invitrogen) and growth was scaled up in Hyperflasks (Cat. No. 3319 Corning Life Sciences) for three days. Trypsin was used to harvest the cell line which was washed 3 times in ice cold PRMI supplemented with 10% FBS. No greater than 300 ml of peripheral blood was collected from healthy volunteers. Peripheral blood lymphocytes (PBMCs) were isolated from heparinized blood using Accuspin tubes in accordance with the manufactures' protocol (Cat. No. A0561-100x 15 ml, Aldrich). Counted cell suspensions were combined such that each mouse received an injection of 1.5×10$^6$ PBMCs and 3×10$^6$ tumor cells in a single bolus injection of 0.2 mL in PBS. The combined cell suspension was washed twice with cold PBS, placed on ice and immediately injected into prepared mice.

Figure 6:
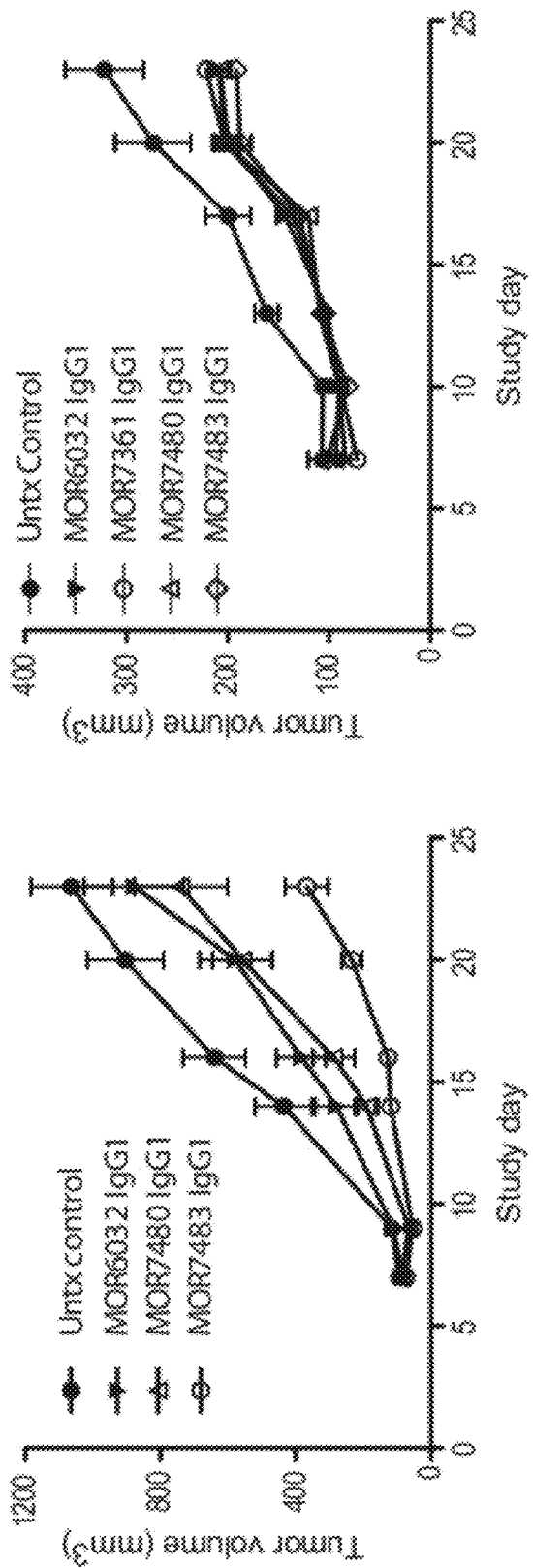
FIG. 6 are line graphs showing the growth of tumors injected subcutaneously with tumor cells (PC3, left panel; LOVO, right panel) and human peripheral blood mononuclear cells on study day 0. Mice were injected with 10 mg/kg of the indicated 4-1BB mAbs on day 0.

For each mouse, a 0.2 mL volume of the combined cell suspension was injected subcutaneously into the right flank of the animal and given a single dose (0.2 mL) of the 4-1BB antibody or control antibody by subcutaneous injection into the left flank. Tumor measurements were made via Pressier caliper twice per week for the duration of the experiments and body weights were also recorded. Tumor volume was calculated using the following calculation: length×width$^2$×0.44=volume (mm$^3$) Mice were removed from the study in the event that the tumor volume reached 2000 mm$^3$ or an animal lost 20% of body weight before termination of the experiment. On day 23 mice from all groups were euthanized in accordance with procedures outlined by the IACUC (FIG. 6). Percent tumor growth inhibition was measured on the final day of the study and is calculated as 100−{1−(Treated$_{final\ day}$/Control$_{final\ day}$)}. Similar results were observed when tumors were measured on day 6 post injection, and the animals were randomized according to tumor volume, and given a single 4-1BB mAb dose on day 7 post implantation. For most studies, each group contained 8 mice.

Example 9

In Vivo Assessment of Activity of 4-1BB Antibodies in Human 4-1BB Knock in Mice Generation of Human 4-1BB Knock-in Mice To better address the immune modulating activities of anti-human 4-1BB monoclonal antibodies that do not cross react with murine 4-1BB, a mouse model in which the mouse 4-1BB gene was replaced by the human 4-1BB gene was generated. Bacterial artificial chromosome (BAC) clones carrying the human or murine 4-1BB genomic fragment were ordered from Invitrogen (Carlsbad, Calif.) and used to construct the 4-1BB targeting vector based on the Red/ET recombination technology (Zhang, 1998, Nat Genet. 20:123-128). First, a retrieval vector was assembled on the pBR322 backbone such that, when opened by Xba1 digestion, the two murine/human chimeric homology arms (400 bps each) will retrieve from the human 4-1BB BAC clone the 19,994 bps of human 4-1BB genomic sequence beginning with the translation start codon ATG located in exon 2 and ending with the stop codon TGA in exon 8. Second, a neomycin expression cassette under the control of the PGK/EM7 promoters was assembled and flanked by 100 base pairs (bps) of sequences homologous to intron 2 sequences of the human 4-1BB gene. This neomycin expression cassette was then targeted into the retrieved human 4-1BB genomic fragment obtained in step 1. Lastly, the retrieved human 4-1BB genomic fragment carrying the neomycin expression cassette was targeted into a murine BAC clone to replace the murine 4-1BB gene with the modified human 4-1BB genomic fragment from ATG start codon to TGA stop codon.

This BAC targeting vector was electroporated into a mouse embryonic stem cell line on the C57BL/6NTAC background (PRX-BL6N #1, Primogenix, Laurie, Mo.) following a standard protocol and clones surviving G418 (also known as geneticin) selection were screened by two Taqman assays against intron 2 and exon 8 of the murine 4-1BB gene to identify clones that had been modified at the murine 4-1BB locus by a homologous recombination mechanism Of the 116 ES clones screened, 7 clones were found to have lost one allele of the murine 4-1BB locus (targeting efficiency 6%). Karyotype analysis and in situ hybridization (FISH) were performed by Coriell Institute for Medical Research (Camden, N.J.). For clone LH15, 19 out of 20 cells were 40 XY, and for LH80, 20 out of 20 cells 40XY. In both clones, FISH using a murine BAC clone carrying the 4-1BB gene as a probe showed one signal of 4-1BB hybridization on each of the chromosome 4 pair in the region of band E2. No signal was seen at any other locations.

Both clones LH15 and LH80 were injected into blastocysts of the BALB/c strain and embryos implanted into the CD1 pseudopregnant female mice to carry to term. Male chimeras were mated to the Ella-cre mice on C57BL/6 background to remove the neomycin resistance cassette and mice homozygous for the human 4-1BB gene were used in study.

4-1BB Agonist mAb Mediated Lymphocyte Proliferation.

Figure 7:
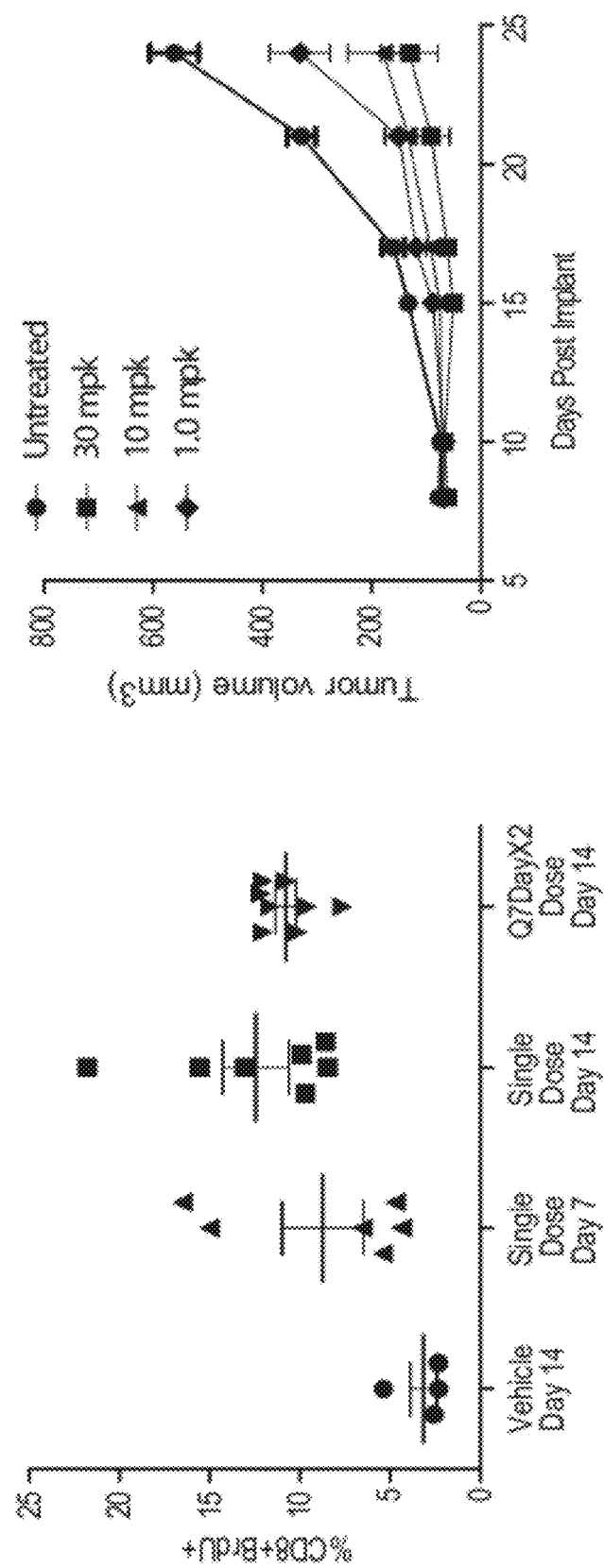
FIG. 7 Left panel is a scattergram showing the percentage of PBMC that are positive for both the T cell surface marker CD8+ and have incorporated the BrdU nucleoside analog following treatment of 4-1BB knock in mice with 4-1BB mAb or vehicle control. The right panel is a line graph showing the growth of murine melanoma tumors injected subcutaneously into 4-1BB knock in mice and treated with the indicated concentration of 4-1BB mAb.

The ability of 4-1BB agonist mAbs to induce lymphocyte proliferation was assessed in 4-1BB Knock-in mice. 4-1BB Knock-in mice were dosed via intraperitoneal injection with 30 mg/kg of MOR7480.1 on study Day 0 (for weekly dosing animals received 4-1BB mAb injections on Day 0 and Day 7). 24 hours prior to sample collection, animals were injected intraperitoneally with 2 mg BrdU. At the indicated day post dose, peripheral blood samples were collected via intracardiac puncture. PBMC were stained with antibodies against CD3, CD4, CD8, and BrdU and assessed via flow cytometry. Results are presented in FIG. 7 panel A.

4-1BB Agonist mAb Mediated Anti-Tumor Efficacy

Anti-tumor efficacy of MOR7480.1 was assessed in 4-1BB knock in mice using B16-OVA/luc, a melanoma line that has been engineered to express the ovalbumin (OVA) model antigen and luciferase (luc). One million tumor cells were implanted on the flank of 4-1BB knock in mice. Animals were randomized based on tumor size on when tumors reached approximately 50-100 mm$^3$ (generally 7-10 days post tumor inoculation) and given a single injection of the indicated dose of 4-1BB mAb. Tumor size was assessed using caliper measurement two to three times per week until study termination. Results are presented in FIG. 7 panel B.

The invention claimed is:

1. An isolated antibody, or antigen-binding portion thereof, wherein said antibody, or antigen-binding portion comprises:
   (a) the H-CDR1 as set forth in SEQ ID NO:29;
   (b) the H-CDR2 as set forth in SEQ ID NO:30;
   (c) the H-CDR3 as set forth in SEQ ID NO:31;
   (d) the L-CDR1 as set forth in SEQ ID NO:34;
   (e) the L-CDR2 as set forth in SEQ ID NO:35; and
   (f) the L-CDR3 as set forth in SEQ ID NO:36.

2. The antibody, or antigen-binding portion according to claim 1 wherein said antibody, or antigen-binding portion comprises the $V_H$ region amino acid sequence as set forth in SEQ ID NO:43.

3. The antibody, or antigen-binding portion according to claim 1 wherein said antibody, or antigen-binding portion comprises the $V_L$ region amino acid sequence as set forth in SEQ ID NO:45.

4. The antibody, or antigen-binding portion according to claim 1, comprising the $V_H$ region amino acid sequence as set forth in SEQ ID NO:43 and the $V_L$ region amino acid sequence as set forth in SEQ ID NO:45.

5. The isolated antibody according to claim 1, which is an IgG2.

6. A pharmaceutical composition comprising an antibody, or antigen-binding portion thereof, according to claim 1 and a pharmaceutically acceptable carrier.

7. An isolated antibody, wherein said antibody comprises the heavy chain amino acid sequence as set forth in SEQ ID NO:44 and further comprises the light chain amino acid sequence as set forth in SEQ ID NO:46, with the proviso that the C-terminal lysine residue of SEQ ID NO:44 is optionally absent.

* * * * *

UNITED STATES PATENT AND TRADEMARK OFFICE
CERTIFICATE OF CORRECTION

PATENT NO. : 8,337,850 B2  
APPLICATION NO. : 13/228532  
DATED : December 25, 2012  
INVENTOR(S) : Bianca Ahrens et al.

Page 1 of 1

It is certified that error appears in the above-identified patent and that said Letters Patent is hereby corrected as shown below:

In the Title Page item (73) Assignee:

Replace "Pfizer Inc., San Diego, CA (US)" with --Pfizer Inc., New York, NY (US)--

Signed and Sealed this
Twenty-fourth Day of September, 2013

Teresa Stanek Rea
*Deputy Director of the United States Patent and Trademark Office*